(12) United States Patent
Manoharan et al.

(10) Patent No.: US 9,701,623 B2
(45) Date of Patent: Jul. 11, 2017

(54) DI-ALIPHATIC SUBSTITUTED PEGYLATED LIPIDS

(71) Applicants: ALNYLAM PHARMACEUTICALS, INC., Cambridge, MA (US); TAKEDA PHARMACEUTICAL COMPANY LIMITED, Osaka-Shi (JP)

(72) Inventors: Muthiah Manoharan, Cambridge, MA (US); Kallanthottathil G. Rajeev, Cambridge, MA (US); Jayaprakash K. Nair, Cambridge, MA (US); Muthusamy Jayaraman, Cambridge, MA (US); Satoru Matsumoto, Kanagawa (JP)

(73) Assignees: ALNYLAM PHARMACEUTICALS, INC., Cambridge, MA (US); TAKEDA PHARMACEUTICAL CO. LTD, Osaka-Shi (JP)

( * ) Notice: Subject to any disclaimer, the term of this patent is extended or adjusted under 35 U.S.C. 154(b) by 0 days.

(21) Appl. No.: 14/346,924

(22) PCT Filed: Sep. 27, 2012

(86) PCT No.: PCT/US2012/057527
§ 371 (c)(1),
(2) Date: Jun. 24, 2014

(87) PCT Pub. No.: WO2013/049328
PCT Pub. Date: Apr. 4, 2013

(65) Prior Publication Data
US 2015/0203446 A1    Jul. 23, 2015

Related U.S. Application Data

(60) Provisional application No. 61/539,797, filed on Sep. 27, 2011.

(51) Int. Cl.
| | | |
|---|---|---|
| C07C 271/16 | (2006.01) |
| C07C 43/04 | (2006.01) |
| C07C 235/74 | (2006.01) |
| C12N 15/113 | (2010.01) |
| C07C 237/06 | (2006.01) |
| A61K 9/127 | (2006.01) |
| A61K 47/48 | (2006.01) |

(52) U.S. Cl.
CPC .......... *C07C 271/16* (2013.01); *A61K 9/1271* (2013.01); *A61K 47/48215* (2013.01); *C07C 43/04* (2013.01); *C07C 235/74* (2013.01); *C07C 237/06* (2013.01); *C12N 15/1137* (2013.01); *C12N 2310/14* (2013.01); *C12N 2320/32* (2013.01)

(58) Field of Classification Search
None
See application file for complete search history.

(56) References Cited

U.S. PATENT DOCUMENTS

2010/0317048 A1    12/2010  Fujimoto et al.
2011/0200582 A1    8/2011   Baryza et al.

FOREIGN PATENT DOCUMENTS

EP     2261662 A1       12/2010
WO     WO-2011076807 A2  6/2011

OTHER PUBLICATIONS

Database CAPLUS, Acc. No. 1997:111198, Schwartz et al., WO 9640726 A1 (Dec. 19, 1996) (abstract).*
Database CAPLUS in STN, Acc. No. 2000:301103, Honma et al., JP 2000129587 A (May 9, 2000) (abstract).*
Hodoshima, et al., Lipid Nanoparticles for Delivering Antitumor Drugs, International Journal of Pharmaceutics, 1997, 146(1):81-92.
Metselaar, et al., A Novel Family of L-Amino Acid-Based Biodegradable Polymer-Lipid Conjugates for the Development of Long-Circulating Liposomes with Effective Drug-Targeting Capacity, Bioconjugate Chem. 2003, 14(6):1156-1164.
International Search Report issued in PCT/US2012/057527 on Apr. 2, 2013.

* cited by examiner

*Primary Examiner* — Brian J Davis
(74) *Attorney, Agent, or Firm* — Blank Rome LLP

(57) ABSTRACT

The disclosure relates to di-aliphatic substituted PEGylated lipids and to methods of their preparation. The disclosure also relates to lipid conjugates containing di-aliphatic substituted PEGylated lipids, and to the use of di-aliphatic substituted PEGylated-lipid conjugates in drug delivery.

40 Claims, 1 Drawing Sheet

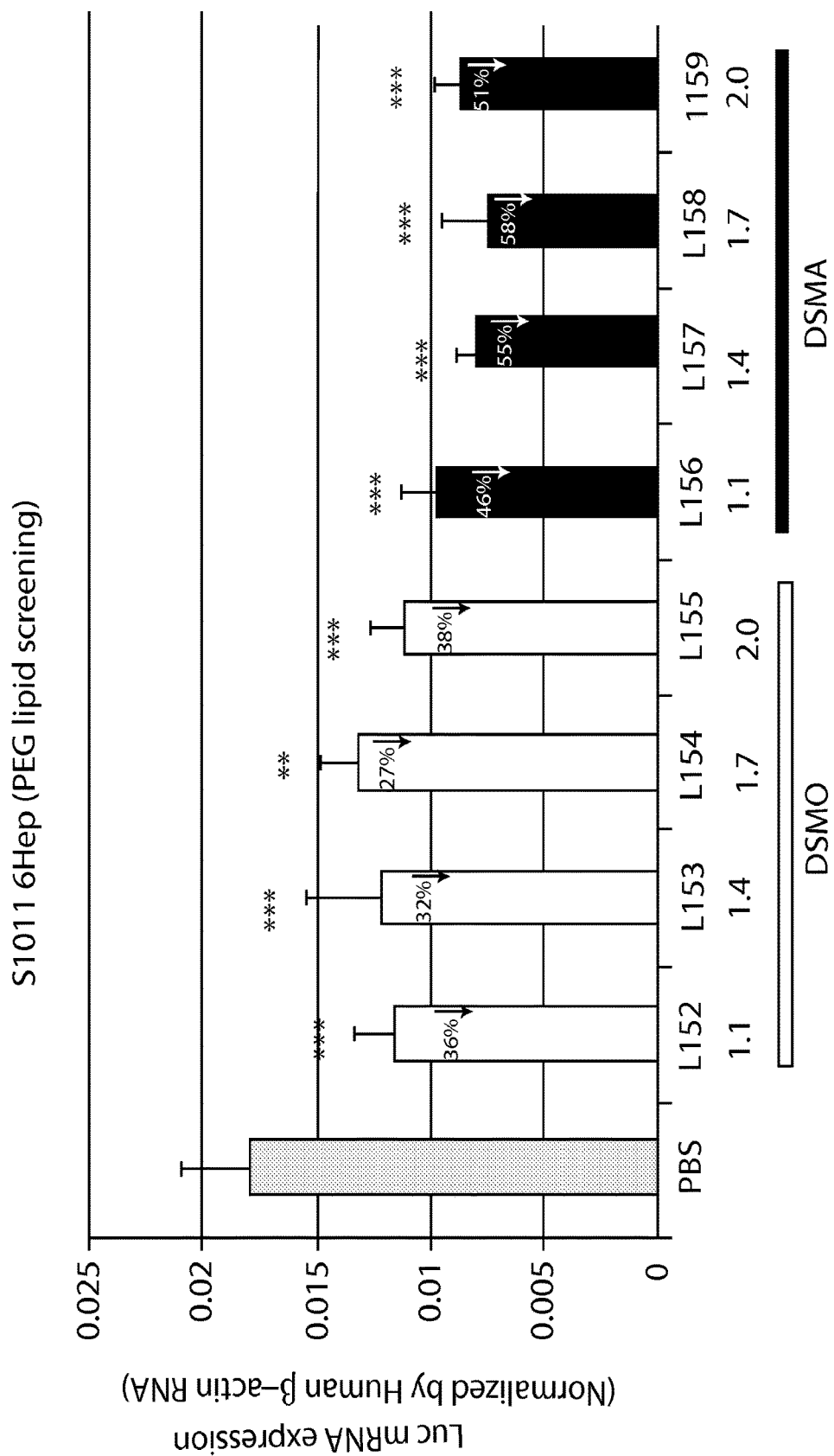

DI-ALIPHATIC SUBSTITUTED PEGYLATED LIPIDS

This application is the U.S. national phase of International Patent Application No. PCT/US2012/057527, filed Sep. 27, 2012, which claims the benefit of U.S. Provisional Application No. 61/539,797, filed Sep. 27, 2011, which is incorporated by reference in its entirety.

FIELD OF THE INVENTION

The present invention relates to di-aliphatic substituted lipids, methods of preparing them, and their use as aggregation-reducing agents. The present invention also relates to lipid particles containing di-aliphatic substituted lipids, and to the use of such lipid particles in drug delivery.

BACKGROUND OF THE INVENTION

Therapeutic nucleic acids include, e.g., small interfering RNA (siRNA), micro RNA (miRNA), antisense oligonucleotides, ribozymes, plasmids, immune stimulating nucleic acids, antisense, antagomirs, antimirs, microRNA mimics, supermirs, U1 adaptors, and aptamers. These nucleic acids act via a variety of mechanisms. In the case of siRNA or miRNA, these nucleic acids can down-regulate intracellular levels of specific proteins through a process termed RNA interference (RNAi). Following introduction of siRNA or miRNA into the cell cytoplasm, these double-stranded RNA constructs can bind to a protein termed RISC. The sense strand of the siRNA or miRNA is displaced from the RISC complex providing a template within RISC that can recognize and bind mRNA with a complementary sequence to that of the bound siRNA or miRNA. Having bound the complementary mRNA the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA or miRNA constructs are, first, their susceptibility to nuclease digestion in plasma and, second, their limited ability to gain access to the intracellular compartment where they can bind RISC when administered systemically as the free siRNA or miRNA. These double-stranded constructs can be stabilized by incorporation of chemically modified nucleotide linkers within the molecule, for example, phosphothioate groups. However, these chemical modifications provide only limited protection from nuclease digestion and may decrease the activity of the construct. Intracellular delivery of siRNA or miRNA can be facilitated by use of carrier systems such as polymers, cationic liposomes or by chemical modification of the construct, for example by the covalent attachment of cholesterol molecules. However, improved delivery systems are required to increase the potency of siRNA and miRNA molecules and reduce or eliminate the requirement for chemical modification.

Antisense oligonucleotides and ribozymes can also inhibit mRNA translation into protein. In the case of antisense constructs, these single stranded deoxynucleic acids have a complementary sequence to that of the target protein mRNA and can bind to the mRNA by Watson-Crick base pairing. This binding either prevents translation of the target mRNA and/or triggers RNase H degradation of the mRNA transcripts. Consequently, antisense oligonucleotides have tremendous potential for specificity of action (i.e., down-regulation of a specific disease-related protein). To date, these compounds have shown promise in several in vitro and in vivo models, including models of inflammatory disease, cancer, and HIV (reviewed in Agrawal, Trends in Biotech. 14:376-387 (1996)). Antisense can also affect cellular activity by hybridizing specifically with chromosomal DNA. Advanced human clinical assessments of several antisense drugs are currently underway. Targets for these drugs include the bcl2 and apolipoprotein B genes and mRNA products.

Immune-stimulating nucleic acids include deoxyribonucleic acids and ribonucleic acids. In the case of deoxyribonucleic acids, certain sequences or motifs have been shown to illicit immune stimulation in mammals. These sequences or motifs include the CpG motif, pyrimidine-rich sequences and palindromic sequences. It is believed that the CpG motif in deoxyribonucleic acids is specifically recognized by an endosomal receptor, toll-like receptor 9 (TLR-9), which then triggers both the innate and acquired immune stimulation pathway. Certain immune stimulating ribonucleic acid sequences have also been reported. It is believed that these RNA sequences trigger immune activation by binding to toll-like receptors 6 and 7 (TLR-6 and TLR-7). In addition, double-stranded RNA is also reported to be immune stimulating and is believed to activate via binding to TLR-3.

One well known problem with the use of therapeutic nucleic acids relates to the stability of the phosphodiester internucleotide linkage and the susceptibility of this linker to nucleases. The presence of exonucleases and endonucleases in serum results in the rapid digestion of nucleic acids possessing phosphodiester linkers and, hence, therapeutic nucleic acids can have very short half-lives in the presence of serum or within cells. (Zelphati, O., et al., Antisense. Res. Dev. 3:323-338 (1993); and Thierry, A. R., et al., pp 147-161 in Gene Regulation: Biology of Antisense RNA and DNA (Eds. Erickson, R P and Izant, J G; Raven Press, NY (1992)). Therapeutic nucleic acids being currently being developed do not employ the basic phosphodiester chemistry found in natural nucleic acids, because of these and other known problems.

This problem has been partially overcome by chemical modifications that reduce serum or intracellular degradation. Modifications have been tested at the internucleotide phosphodiester bridge (e.g., using phosphorothioate, methyl-phosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. (1997)). Others have attempted to improve stability using 2'-5' sugar linkages (see, e.g., U.S. Pat. No. 5,532,130). Other changes have been attempted. However, none of these solutions have proven entirely satisfactory, and in vivo free therapeutic nucleic acids still have only limited efficacy.

In addition, as noted above relating to siRNA and miRNA, problems remain with the limited ability of therapeutic nucleic acids to cross cellular membranes (see, Vlassov, et al., Biochim. Biophys. Acta 1197:95-1082 (1994)) and in the problems associated with systemic toxicity, such as complement-mediated anaphylaxis, altered coagulatory properties, and cytopenia (Galbraith, et al., *Antisense Nucl. Acid Drug Des.* 4:201-206 (1994)).

In an attempt to improve efficacy, investigators have also employed lipid-based carrier systems to deliver chemically modified or unmodified therapeutic nucleic acids. In Zelphati et al., *J. Contr. Rel.* 41:99-119 (1996), the authors refer to the use of anionic (conventional) liposomes, pH sensitive liposomes, immunoliposomes, fusogenic liposomes, and cationic lipid/antisense aggregates. In Heyes, et. al., *J. Contr. Rel.* 112:280-290 (2006), the authors refer to the use of more stable poly(ethylene glycol)-lipid conjugates. Similarly siRNA has been administered systemically in cationic liposomes, and these nucleic acid-lipid particles have been reported to provide improved down-regulation of target proteins in mammals including non-human primates (Zimmermann et al., *Nature* 441: 111-114 (2006)).

In spite of this progress, there remains a need in the art for improved lipid-therapeutic nucleic acid compositions that are suitable for general therapeutic use. Preferably, these compositions would encapsulate nucleic acids with high-efficiency, have high drug:lipid ratios, protect the encapsulated nucleic acid from degradation and clearance in serum, be suitable for systemic delivery, and provide intracellular delivery of the encapsulated nucleic acid. In addition, these lipid-nucleic acid particles should be well-tolerated and provide an adequate therapeutic index, such that patient treatment at an effective dose of the nucleic acid is not associated with significant toxicity and/or risk to the patient. Compositions, methods of making the compositions, and methods of using the compositions to introduce nucleic acids into cells, including for the treatment of diseases, are provided.

SUMMARY OF THE INVENTION

The present invention relates to di-aliphatic substituted compounds which are useful as aggregation-reducing agents.

In one aspect, the present invention relates to a compound of formula (I):

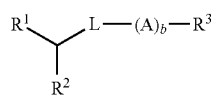

(I)

or a pharmaceutically acceptable salt thereof, wherein $R^1$ and $R^2$ are each, independently, a $C_{10}$ to $C_{30}$ aliphatic group, wherein each aliphatic group is optionally substituted by one or more groups each independently selected from $R^a$;

L is -$L^1$-$Z^1$-($L^2$-$Z^2$)$_c$-$L^3$-;

$L^1$ is a bond, —(CR$^5$R$^{5'}$)$_i$—, or —(CR$^5$R$^{5'}$)$_i$—(C(R$^a$)=C(R$^b$))$_k$—(C≡C)$_k$—(CR$^a$R$^b$)$_j$—;

$Z^1$ is —O—, —S—, —N(R$^c$)—, —OC(O)—, —C(O)O—, —OC(O)O—, —OC(O)N(R$^c$)—, —N(R$^c$)C(O)O—, —N(R$^c$)C(O)N(R$^c$)—, —N(R$^c$)C(O)—, —C(O)N(R$^c$)—, —N=C(R$^a$)—, —C(R$^a$)=N—, —O—N=C(R$^a$)—, —O—N(R$^c$)—; heteroaryl, or heterocyclyl;

$L^2$ is —(CR$^a$R$^b$)$_p$— or —(CR$^a$R$^b$)$_j$—(C(R$^a$)=C(R$^b$))$_k$—(C≡C)$_k$—(CR$^a$R$^b$)$_j$—;

$Z^2$ is —O—, —S—, —N(R$^c$)—, —OC(O)—, —C(O)O—, —OC(O)O—, —OC(O)N(R$^c$)—, —N(R$^c$)C(O)O—, —N(R$^c$)C(O)—, —C(O)N(R$^c$)—, —N=C(R$^a$)—, —C(R$^a$)=N—, —O—N=C(R$^a$)—, or —O—N(R$^c$)—, heteroaryl, or heterocyclyl;

$L^3$ is —(CR$^a$R$^b$)$_i$—;

each A, independently, is -$L^4$-, —NH-($L^4$)$_q$-(CR$^a$R$^b$)$_r$—C(O)—, or —C(O)—(CR$^a$R$^b$)$_r$-($L^4$)$_q$-NH—; wherein each q, independently, is 0, 1, 2, 3, or 4; and each r, independently, is 0, 1, 2, 3, or 4;

each $L^4$, independently, is —(CR$^a$R$^b$)$_s$O— or —O(CR$^a$R$^b$)$_s$—; wherein each s, independently, is 0, 1, 2, 3, or 4;

$R^3$ is —H, —R$^c$, or —OR$^c$;

each occurrence of $R^5$ and $R^{5'}$ is, independently, —H, halo, cyano, hydroxy, nitro, alkyl, alkenyl, alkynyl, or cycloalkyl;

each occurrence of $R^a$ and $R^b$ is, independently, —H, halo, cyano, hydroxy, nitro, amino, alkylamino, dialkylamino, alkyl, alkenyl, alkynyl, cycloalkyl, alkoxy, aryl, heteroaryl, or heterocyclyl;

each $R^c$ is, independently, —H, alkyl, acyl, cycloalkyl, alkenyl, alkynyl, aryl, heteroaryl, or heterocyclyl;

b is an integer from 1 to 1,000;

c is 0 or 1;

each occurrence of i is, independently, 1, 2, 3, 4, 5, 6, 7, 8 or 9;

each occurrence of j, independently, is 0, 1, 2, or 3;

each occurrence of k is, independently, is 0, 1, 2, or 3; and p is 1 to 10.

In certain embodiments, $R^1$ and $R^2$ are each, independently, aliphatic groups; for example, groups composed primarily of carbon and hydrogen, either saturated or unsaturated, but without aromatic rings. In additional embodiments, $R^1$ and $R^2$ are each, independently $C_{10}$ to $C_{20}$ alkyl or $C_{10}$ to $C_{20}$ alkenyl. For example, $R^1$ and $R^2$ are each, independently $C_{12}$ to $C_{20}$ alkyl or $C_{12}$ to $C_{20}$ alkenyl. For further example, $R^1$ and $R^2$ are each, independently, $C_{12}$-alkyl, $C_{13}$-alkyl, $C_{14}$-alkyl, $C_{15}$-alkyl, $C_{16}$-alkyl, $C_{17}$-alkyl, $C_{18}$-alkyl, $C_{19}$-alkyl, or $C_{20}$-alkyl.

In one embodiment, $R^1$ and $R^2$ are each, individually, $C_8$ to $C_{20}$ alkyl or $C_8$ to $C_{20}$ alkenyl. In another embodiment, $R^1$ and $R^2$ are each, individually, $C_{10}$ to $C_{20}$ alkyl or $C_{10}$ to $C_{20}$ alkenyl. For instance, $R^1$ and $R^2$ can each, individually, be selected from octanyl, nonanyl, decyl, lauryl, myristyl, palmityl, stearyl, α-linoleyl, stearidonyl, linoleyl, γ-linolenyl, arachidonyl, or oleyl.

In one embodiment, $R^1$ and $R^2$ are each unsubstituted. In another embodiment, $R^1$ and $R^2$ are each substituted. In one embodiment, one of $R^1$ and $R^2$ is substituted and the other of $R^1$ and $R^2$ is unsubstituted.

In a further embodiment, L is -$L^1$-$Z^1$-$L^3$-. In another embodiment, L is $L^1$-$Z^1$-$L^2$-$Z^2$-$L^3$-.

In yet another embodiment, $L^1$ is a bond or —(CR$^5$R$^{5'}$)$_i$—. For example, $L^1$ can be a bond, —CH$_2$— or —CH$_2$—CH$_2$—. In one embodiment, $L^1$ is a bond. In another embodiment, $L^1$ is —(CR$^5$R$^{5'}$)$_i$—, e.g., —CH$_2$—. In yet another embodiment, $L^1$ is —(CR$^5$R$^{5'}$)$_2$, such as —CH$_2$—CH$_2$—.

In yet another embodiment, $Z^1$ is —O—, —N(R$^c$)—, —OC(O)—, —C(O)O—, —OC(O)N(R$^c$)—, —N(R$^c$)C(O)O—, —N(R$^c$)C(O)N(R$^c$)—, —N(R$^c$)C(O)—, —C(O)N(R$^c$)—, —O—N=C(R$^a$)—, —O—N(R$^c$)—; heteroaryl, or heterocyclyl.

For example, in certain embodiments, $Z^1$ is —O—, —N(H)—, —N(CH$_3$)—, —OC(O)—, —C(O)O—, —OC(O)N(H)—, —OC(O)N(CH$_3$)—, —N(H)C(O)O—, —N(CH$_3$)C(O)O—, —N(H)C(O)N(H)—, —N(H)C(O)N(CH$_3$)—, —N(CH$_3$)C(O)N(CH$_3$)—, —N(CH$_3$)C(O)N(H)—, —N(H)C(O)—, —N(CH$_3$)C(O)—, —C(O)N(H)—, —C(O)N(CH$_3$)—, —O—N=C(H)—, —O—N=C(CH$_3$)—, —O—N(H)—, —O—N(CH$_3$)— or heteroaryl (such as triazolyl, e.g., 1,2,3-triazolyl).

In another embodiment, $Z^1$ is —N(R$^c$)—, —N(R$^c$)C(O)O—, —N(R$^c$)C(O)N(R$^c$)—, —N(R$^c$)C(O)—, or —N=C(R$^a$)—, wherein the leftmost nitrogen atom in $Z^1$ is attached to the tertiary carbon atom of formula (I), or $Z^1$ is a nitrogen-containing heteroaryl or heterocyclyl, wherein the nitrogen atom of the heteroaryl or heterocyclyl is bound to $L^1$ (or if $L^1$ is a bond, then to the central tertiary carbon atom).

In yet another embodiment, $L^2$ is —(CR$^a$R$^b$)$_p$— and c is 1. For example, $L^2$ can be —(CR$^a$R$^b$)$_1$ (such as —CH$_2$—) or —(CR$^a$R$^b$)$_2$ (such as —CH$_2$—CH$_2$—).

In yet another embodiment, $Z^2$ is —O—, —C(O)O—, —C(O)N(R$^c$)—, or heteroaryl and c is 1. For example, $Z^2$ is —O—, —C(O)N(H)—, —C(O)N(CH$_3$)—, or heteroaryl (such as triazolyl, e.g., 1,2,3-triazolyl).

In additional embodiments, $L^3$ is —(CR$^a$R$^b$)$_i$— in which each occurrence of R$^a$ and R$^b$ are, independently, H, alkyl, alkenyl, alkynyl, or cycloalkyl. For example, each occurrence of R$^a$ and R$^b$ can be, independently, H or alkyl. In another embodiment, each occurrence of R$^a$ and R$^b$ can be, independently, H or alkyl, and the variable i is 2, 3, 4, or 5. Suitable $L^3$ groups include, but are not limited to, —CH$_2$—, —CH$_2$—CH$_2$—, —CH(CH$_3$)—CH$_2$—, —CH(CH$_3$)—CH$_2$—CH$_2$—, —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and —CH$_2$—CH$_2$—CH$_2$—CH$_2$—CH$_2$—CH$_2$—.

In one embodiment, $L^3$ is —CH$_2$—. In another embodiment, $L^3$ is —CH$_2$—CH$_2$—. In yet another embodiment, $L^3$ is —CH$_2$—CH$_2$—CH$_2$—. In yet another embodiment, $L^3$ is —CH$_2$—CH$_2$—CH$_2$—CH$_2$—. In yet another embodiment, $L^3$ is —CH$_2$—CH$_2$—CH$_2$—CH$_2$—CH$_2$—. In yet another embodiment, $L^3$ is —CH$_2$—CH$_2$—CH$_2$—CH$_2$—CH$_2$—CH$_2$—. In yet another embodiment, $L^3$ is —CH$_2$—CH$_2$—CH$_2$—CH$_2$—CH$_2$—CH$_2$—CH$_2$—. In yet another embodiment, $L^3$ is —CH$_2$—CH$_2$—CH$_2$—CH$_2$—CH$_2$—CH$_2$—CH$_2$—CH$_2$— In one embodiment, L$_3$ is —CH(CH$_3$)—CH$_2$—CH$_2$—.

In certain embodiments, -(A)$_b$- is a polymeric group, i.e., a group made up of repeating units of -A-. In one embodiment, each A is, independently, $L^4$.

In further embodiments, each $L^4$ is, independently, —(CR$^a$R$^b$)$_s$O— or —O(CR$^a$R$^b$)$_s$— in which each s is, independently, for example, 1, 2, 3 or 4. In one embodiment, each occurrence of R$^a$ and R$^b$ in $L^4$ is, independently, H or alkyl. Thus in some embodiments the group -(A)$_b$- is a polyoxyalkylene, such as a poly(ethylene glycol) or a poly(propylene glycol). For example, $L^4$ can be —OCH$_2$CH$_2$—, —CH$_2$CH$_2$O—, —OCH$_2$CH$_2$CH$_2$—, —OCH(CH$_3$)CH$_2$CH$_2$—, —OCH$_2$CH$_2$—CH(CH$_3$)—, —OCH(CH$_3$)CH$_2$— or —OCH$_2$CH(CH$_3$)—. In a preferred embodiment, each $L^4$ is —OCH$_2$CH$_2$—.

In additional embodiments, each A group is, independently —NH-(L$^4$)$_q$-(CR$^a$R$^b$)$_r$—C(O)—, or —C(O)—(CR$^a$R$^b$)$_r$-(L$^4$)$_q$-NH—. In these situations, the group -(A)$_b$- is a polyamide. Suitable polyamides are described in, for example, U.S. Pat. No. 6,320,017. For example, the group -(A)$_b$- can have the structure —[NH(CH$_2$CH$_2$O)$_4$CH$_2$C(O)]$_b$—.

In additional embodiments, the group -(A)$_b$- is a copolymer, i.e., a polymer of more than one different kind of monomer. Copolymers can have random, block, graft, or other copolymer structures. For example, the group -(A)$_b$- can be a random copolymer of, for example, —(CH$_2$CH$_2$O)— units and —(CH$_2$CH(CH$_3$)O)— units. As another example, the group -(A)$_b$- can be a block copolymer of —(CH$_2$CH$_2$O)— units and —NH-(L$_4$)$_q$-(CR$^a$R$^b$)$_r$—C(O)—.

In certain embodiments, R$_3$ is selected such that the compound terminates in an alkoxy group, e.g., C$_1$-C$_4$ alkoxy such as a methoxy group. In some cases, -(A)$_b$-R$^3$ is selected so as to be a methoxyPEG (mPEG) moiety. The value of b can be selected on the basis of a molecular weight of the mPEG moiety. For example, a molecular weight of 2,000 corresponds to a value of b of approximately 45. In a given preparation, the number of repeating units (referred to as the variable n in the exemplified compounds) can be a distribution of values of b, since polymers may be found as a distribution of different polymer chain lengths.

In certain embodiments, R$^3$ is H, alkyl or OR$^c$. For example, R$^3$ can be H, methyl, or —OH.

In additional embodiments, b ranges from about 1 to about 500, such as from about 5 to about 500, from about 10 to about 500, from about 10 to about 250, from about 25 to about 100, from about 30 to about 60 or from about 40 to about 50.

In one embodiment, c is 0. In another embodiment c is 1.

In one embodiment, i is 1, 2, 3, 4, 5 or 6. In another embodiment, i is 2, 3, 4, 5 or 6. In yet another embodiment, i is 2, 3, 4, or 5.

In a further embodiment, the molecular weight of the compound of Formula (I) is from about 500 g/mol to about 5,000 g/mol.

In yet another embodiment,

R$^1$ and R$^2$ are each, independently C$_{12}$ to C$_{20}$ alkyl or C$_{12}$ to C$_{20}$ alkenyl;

L is -L$^1$-Z$^1$-L$^3$- or -L$^1$-Z$^1$-L$^2$-Z$^2$-L$^3$-;

L$^1$ is a bond or —(CR$^5$R$^{5'}$)$_i$—;

Z$^1$ is —O—, —N(R$^c$)—, —OC(O)—, —C(O)O—, —OC(O)N(R$^c$)—, —N(R$^c$)C(O)O—, —N(R$^c$)C(O)N(R$^c$)—, —N(R$^c$)C(O)—, —C(O)N(R$^c$)—, —O—N=C(R$^a$)—, —O—N(R$^c$)—, heteroaryl, or heterocyclyl;

L$^2$ is —(CR$^a$R$^b$)$_p$—;

Z$^2$ is —O—, —C(O)O—, —C(O)N(R$^c$)—, or heteroaryl;

L$^3$ is —(CR$^a$R$^b$)$_i$—;

each A is, independently, -L$^4$-;

each L$^4$, independently, is —OCH$_2$CH$_2$—, —CH$_2$CH$_2$O—, —OCH(CH$_3$)CH$_2$— or —OCH$_2$CH(CH$_3$)—;

R$^3$ is —OR$^c$;

each occurrence of R$^a$ and R$^b$ is, independently, H or alkyl; and

R$^c$ is H or alkyl.

In yet another embodiment,

R$^1$ and R$^2$ are each, independently C$_{12}$ to C$_{20}$ alkyl or C$_{12}$ to C$_{20}$ alkenyl; and Z$^1$ is —N(R$^c$)—, —N(R$^c$)C(O)O—, —N(R$^c$)C(O)N(R$^c$)—, —N(R$^c$)C(O)—, or —N=C(R$^a$)—, wherein the leftmost nitrogen atom in Z$^1$ is bound to L$^1$ (or if L$^1$ is a bond, then to the central tertiary carbon atom of formula (I)), or Z$^1$ is a nitrogen-containing heteroaryl or heterocyclyl, wherein the nitrogen atom of the heteroaryl or heterocyclyl is bound to L$^1$ (or if L$^1$ is a bond, then to the central tertiary carbon atom of formula (I)). In one preferred embodiment, R$^1$ and R$^2$ are each, independently C$_{12}$ to C$_{20}$ alkyl.

In yet another embodiment, the present invention relates to a compound of the formula

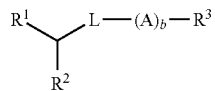
(II)

or a pharmaceutically acceptable salt thereof, wherein
$R^1$ and $R^2$ are each, independently $C_{10}$ to $C_{30}$ aliphatic group (e.g., $C_{12}$ to $C_{20}$ alkyl or $C_{12}$ to $C_{20}$ alkenyl);
L is -$L^1$-$Z^1$-$L^3$-;
$L^1$ is a bond or —$(CR^5R^{5'})_i$—;
$Z^1$ is —N($R^c$)—, —N($R^c$)C(O)O—, —N($R^c$)C(O)N($R^c$)—, —N($R^c$)C(O)—, or —N=C($R^a$)—, wherein the leftmost nitrogen atom in $Z^1$ is bound to $L^1$ (or if $L^1$ is a bond, then to the central tertiary carbon atom of formula (II)), or $Z^1$ is a nitrogen-containing heteroaryl or heterocyclyl, wherein the nitrogen atom of the heteroaryl or heterocyclyl is bound to $L^1$ (or if $L^1$ is a bond, then to the central tertiary carbon atom of formula (II)); $L^3$ is —$(CR^aR^b)_i$—;
each A is, independently, -$L^4$-;
b is an integer from 1 to 1,000;
each $L^4$, independently, is —OCH$_2$CH$_2$—, —CH$_2$CH$_2$O—, —OCH(CH$_3$)CH$_2$— or —OCH$_2$CH(CH$_3$)—; $R^3$ is —O$R^c$;
each occurrence of $R^a$, $R^c$, $R^5$ and $R^{5'}$ is, independently, H or alkyl (e.g., $C_1$-$C_4$ alkyl); and
i is 2, 3, 4 or 5. In one preferred embodiment of the compound of formula (II), $R^1$ and $R^2$ are each, independently $C_{10}$ to $C_{30}$ alkyl, such as $C_{12}$ to $C_{20}$ alkyl. In a preferred embodiment, $R^1$ and $R^2$ are the same.

In one embodiment of the compound of formula (II), $L^1$ is a bond. In another embodiment, $L^1$ is —CH$_2$—.

In one embodiment of the compound of formula (II), $Z^1$ is —N($R^c$)C(O)O—, such as —NHC(O)O—. In another embodiment, $Z^1$ is —N($R^c$)C(O)N($R^c$)—, such as —NHC(O)NH—. In yet another embodiment, $Z^1$ is —N($R^c$)C(O)—, such as —NHC(O)— or —NC(CH$_3$)C(O)—.

In yet another embodiment of the compound of formula (II), $L^1$ is a bond and the variable i is 2.

In yet another embodiment, the present invention relates to a compound of formula (III),

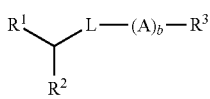
(III)

or a pharmaceutically acceptable salt thereof, wherein
$R^1$ and $R^2$ are each, independently $C_{12}$ to $C_{20}$ alkyl or $C_{12}$ to $C_{20}$ alkenyl;
L is -$L^1$-$Z^1$-$L^2$-$Z^2$-$L^3$;
$L^1$ is a bond or —$(CR^5R^{5'})_i$—;
$Z^1$ is —N($R^c$)—, —N($R^c$)C(O)O—, —N($R^c$)C(O)N($R^c$)—, —N($R^c$)C(O)—, or —N=C($R^a$)—, wherein the leftmost nitrogen atom in $Z^1$ is bound to $L^1$ (or if $L^1$ is a bond, then to the central tertiary carbon atom of formula (II)), or $Z^1$ is a nitrogen-containing heteroaryl or heterocyclyl, wherein the nitrogen atom of the heteroaryl or heterocyclyl is bound to $L^1$ (or if $L^1$ is a bond, then to the central tertiary carbon atom of formula (II));

$L^2$ is —$(CR^aR^b)_p$;
$Z^2$ is —O—, —C(O)O—, —C(O)N($R^c$)—, or heteroaryl;
$L^3$ is —$(CR^aR^b)_i$—;
each A is, independently, -$L^4$-;
b is an integer from 1 to 1,000;
each $L^4$, independently, is —OCH$_2$CH$_2$—, —CH$_2$CH$_2$O—, —OCH(CH$_3$)CH$_2$— or —OCH$_2$CH(CH$_3$)—; $R^3$ is —O$R^c$;
each occurrence of $R^a$, $R^b$, $R^c$, $R^5$ and $R^{5'}$ is, independently, H or alkyl (e.g., $C_1$-$C_4$ alkyl);
i is 2, 3, 4 or 5; and
p is 1 to 10.

In one preferred embodiment of the compound of formula (III), $R^1$ and $R^2$ are each, independently $C_{10}$ to $C_{30}$ alkyl, such as $C_{12}$ to $C_{20}$ alkyl. In a preferred embodiment, $R^1$ and $R^2$ are the same.

In one embodiment of the compound of formula (III), $L^1$ is a bond. In another embodiment, $L^1$ is —CH$_2$—.

In one embodiment of the compound of formula (III), $Z^1$ is —N($R^c$)—, —N($R^c$)C(O)O—, —N($R^c$)C(O)N($R^c$)—, or —N($R^c$)C(O)—. In another embodiment, $Z^1$ is —N($R^c$)C(O)O—, such as —NHC(O)O—. In another embodiment, $Z^1$ is —N($R^c$)C(O)N($R^c$)—, such as —NHC(O)NH—.

In other embodiments of the compounds of formulas (II) and (III), the variables have the definitions which are described above with respect to formula (I) but are encompassed by formula (II) or (III).

In another aspect, the present invention relates to a lipid particle that includes a compound of formula (I) as described herein. For instance, the lipid particle can contain from about 0.5 to about 15% (e.g., from about 0.5 to about 2.5% or from about 0.5 to about 2%) mole percentage of the compound of formula (I). The lipid particle can further include one or more of a cationic lipid, a neutral lipid, and a sterol. In one embodiment, the lipid particle includes a cationic lipid. In another embodiment, the lipid particle includes a cationic lipid, a neutral lipid and a sterol. The neutral lipid can be selected from DSPC, DPPC, POPC, DOPE, and SM. For instance, the lipid particle can contain a cationic lipid present at a mole percentage of about 20% and about 60%; a neutral lipid present at a mole percentage of about 5% to about 25%; a sterol present at a mole percentage of about 25% to about 55%; and the compound of formula (I) present at a mole percentage of about 0.5% to about 15%.

In another embodiment, the lipid particle can further include an active agent (e.g., a biologically active agent). In another embodiment, the active agent can be a nucleic acid selected from a plasmid, an immunostimulatory oligonucleotide, an siRNA, an antisense oligonucleotide, a microRNA, an antagomir, an aptamer, and a ribozyme.

In another aspect, the present invention relates to a pharmaceutical composition that includes (a) a lipid particle that includes a compound of formula (I) as described herein and (b) a pharmaceutically acceptable carrier.

In another aspect, the present invention relates to a method of modulating the expression of a target gene in a cell by providing a lipid particle of the present invention to the cell. In one embodiment, the active agent in the lipid particle is a nucleic acid selected from a plasmid, an immunostimulatory oligonucleotide, an siRNA, an antisense oligonucleotide, a microRNA, an antagomir, an aptamer, and a ribozyme.

In further embodiments, the target gene can be selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, SORT1 gene, XBP1 gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, tumor suppressor genes, and p53 tumor suppressor gene. In one embodiment, the target gene can contain one or more mutations.

In another aspect, the present invention relates to a method of treating a disease or disorder characterized by the overexpression of a polypeptide in a subject that includes providing to the subject a pharmaceutical composition as described herein. In one embodiment, the active agent is a nucleic acid selected from an siRNA, a microRNA, and an antisense oligonucleotide. In certain embodiments, the siRNA, microRNA, or antisense oligonucleotide includes a polynucleotide that specifically binds to a polynucleotide that encodes the polypeptide, or a complement thereof.

In another aspect, the present invention relates to a method of treating a disease or disorder characterized by underexpression of a polypeptide in a subject that includes providing to the subject a pharmaceutical composition as described herein. In one embodiment, the active agent is a plasmid that encodes the polypeptide or a functional variant or fragment thereof.

In another aspect, the present invention relates to a method of inducing an immune response in a subject that includes providing to the subject a pharmaceutical composition as described herein. In one embodiment, the active agent is an immunostimulatory oligonucleotide.

BRIEF DESCRIPTION OF THE DRAWINGS

The FIGURE is a bar graph showing the expression level of luciferase normalized to human beta-actin (measured by TaqMan RT-PCR) in subcutaneous Hep-3B-luc tumors following intravenous administration of siRNA lipid nanoparticles containing either 1.1, 1.4, 1.7 or 2.0 mol % PEG-C-DMSO or 1.1, 1.4, 1.7 or 2.0 mol % PEG-C-DMSA.

DETAILED DESCRIPTION OF THE INVENTION

In general, a compound of formula (I) as described herein is considered a lipid, more particularly an aggregation-reducing lipid. These lipids can be used, for example, in nucleic acid-lipid particle compositions. In some embodiments, a composition described herein provides increased activity of the nucleic acid and/or improved tolerability of the compositions in vivo, which can result in a significant increase in therapeutic index as compared to lipid-nucleic acid particle compositions previously described.

In certain embodiments, compositions for the delivery of siRNA molecules are described. These compositions are effective in down-regulating the protein levels and/or mRNA levels of target proteins. The activity of these compositions can be influenced by the presence of cationic lipids and the molar ratio of cationic lipid in the formulation.

The lipid particles and compositions may be used for a variety of purposes, including the delivery of associated or encapsulated therapeutic agents to cells, both in vitro and in vivo. Accordingly, methods of treating diseases or disorders in a subject in need thereof can include contacting the subject with a lipid particle associated with a suitable therapeutic agent.

As described herein, the lipid particles are particularly useful for the delivery of nucleic acids, including, e.g., siRNA molecules and plasmids. Therefore, the lipid particles and compositions may be used to modulate the expression of target genes and proteins both in vitro and in vivo by contacting cells with a lipid particle associated with a nucleic acid that reduces target gene expression (e.g., an siRNA) or a nucleic acid that may be used to increase expression of a desired protein (e.g., a plasmid encoding the desired protein).

Various exemplary embodiments of lipids, lipid particles and compositions comprising the same, and their use to deliver therapeutic agents and modulate gene and protein expression are described in further detail below.

Under some conditions, lipid particles can undergo charge-induced aggregation, a condition which can be undesirable. Therefore, it can be desirable to include in a lipid particle a compound which can reduce aggregation, for example by sterically stabilizing the particles during formation. Steric stabilization can occur when a compound having a sterically bulky but uncharged moiety shields or screens the charged portions of a lipid particle from close approach to other lipid particles. Such components do not merely prevent aggregation. Rather, they can also increase circulation lifetime and improve delivery of a lipid-nucleic acid composition to target tissues.

One way to provide steric stabilization to particles is to include lipids which include a lipid bearing a sterically bulky group on the exterior of the particle. Suitable sterically bulky groups include hydrophilic polymers, such as poly (oxyalkylenes), e.g., a poly(ethylene glycol) or poly(propylene glycol). Lipids having such bulky groups can be referred to as aggregation-reducing lipids. Where the bulky group is a poly(ethylene glycol), the lipids can be referred to as poly(ethylene glycol)-lipid conjugates, PEGylated lipids, or simply PEG lipids.

The compounds of formula (I) can include one or more asymmetric carbon atoms, giving rise to the possibility of stereoisomeric forms. The compound can take any of several different stereoisomeric forms, including a racemic mixture, a mixture having an enantiomeric excess of one enantiomer, and a substantially stereopure isomer (e.g., having an enantiomeric excess of 95% or more, 98% or more, or 99% or more). When more than one asymmetric carbon atom is present, diastereomeric forms are possible, as are meso compounds. Any of these can be found in varying degrees of purity. Thus, a compound of formula (I) can be in the form of a mixture of different diastereomers, or a substantially pure form of a single diastereomer. All of these compounds, including cis isomers, trans isomers, diastereomic mixtures, racemates, nonracemic mixtures of enantiomers, substantially pure, and pure enantiomers, are within the scope of the present invention.

Optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formula (I) can likewise be obtained by utilizing optically active starting materials in chiral synthesis processes under reaction conditions which do not cause racemization.

Where applicable, the present invention also relates to useful forms of the compounds formula (I), such as base free forms, and pharmaceutically acceptable salts of the compounds of formula (I) for which salts can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Examplary compounds of Formula I include:

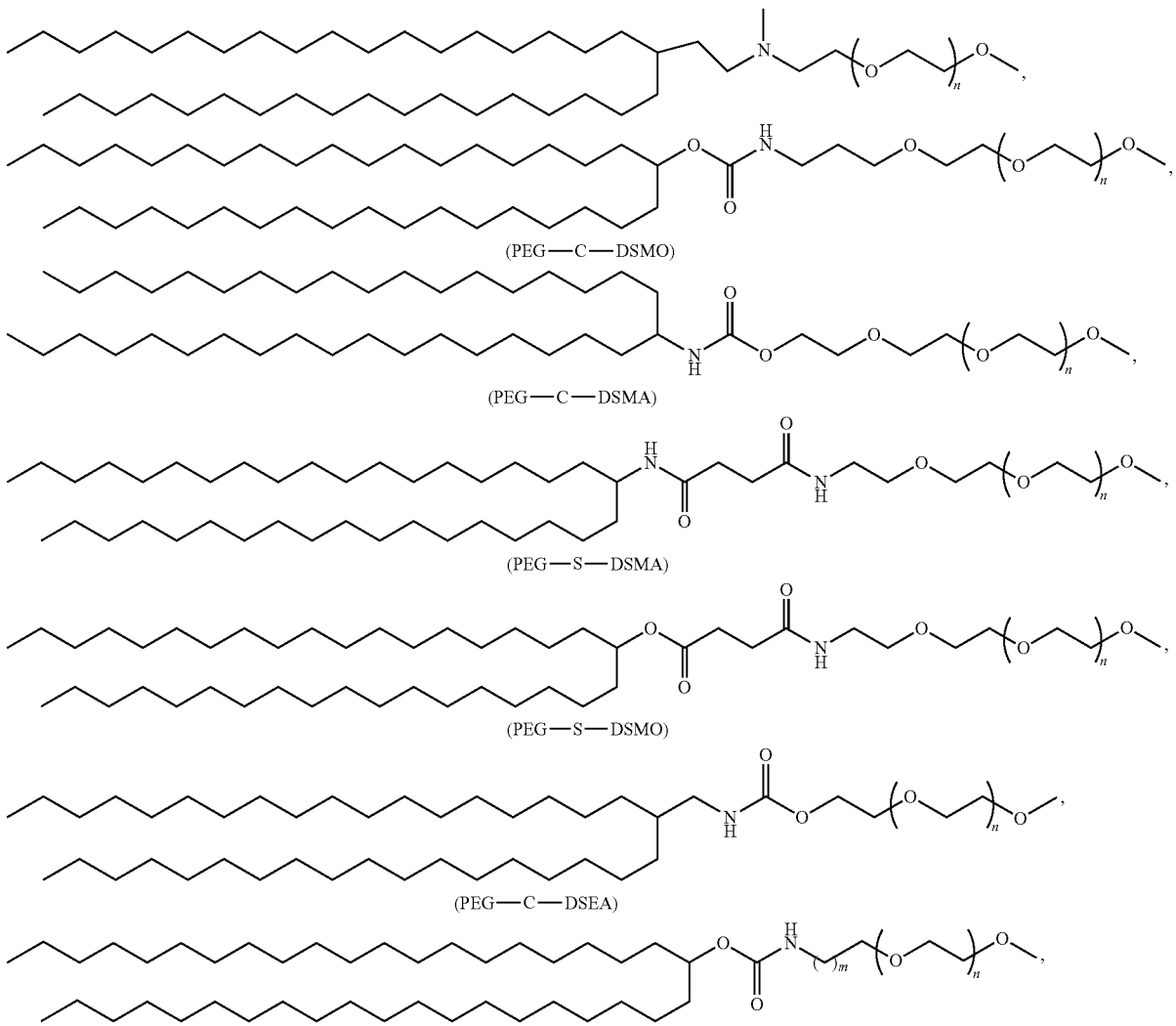

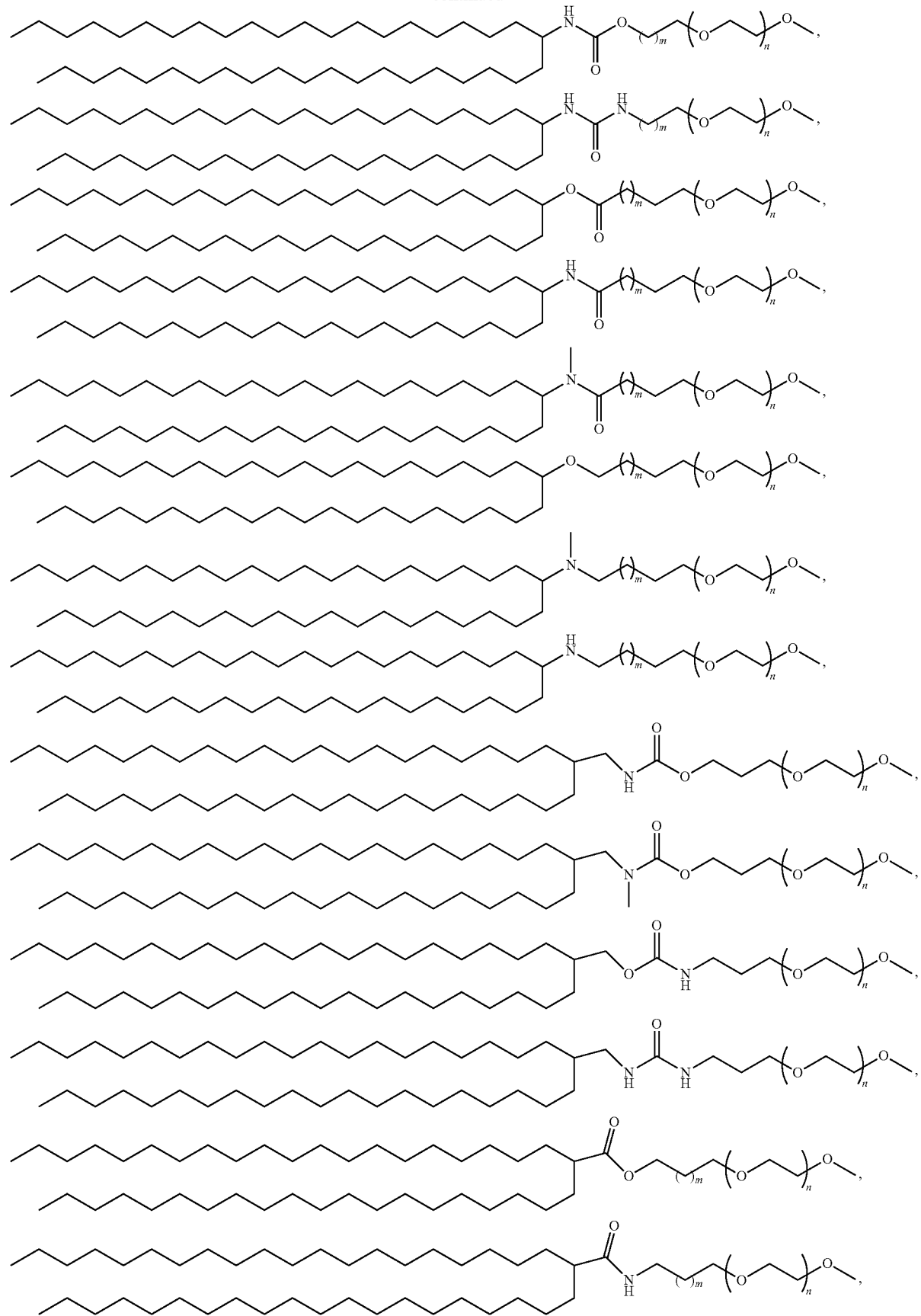

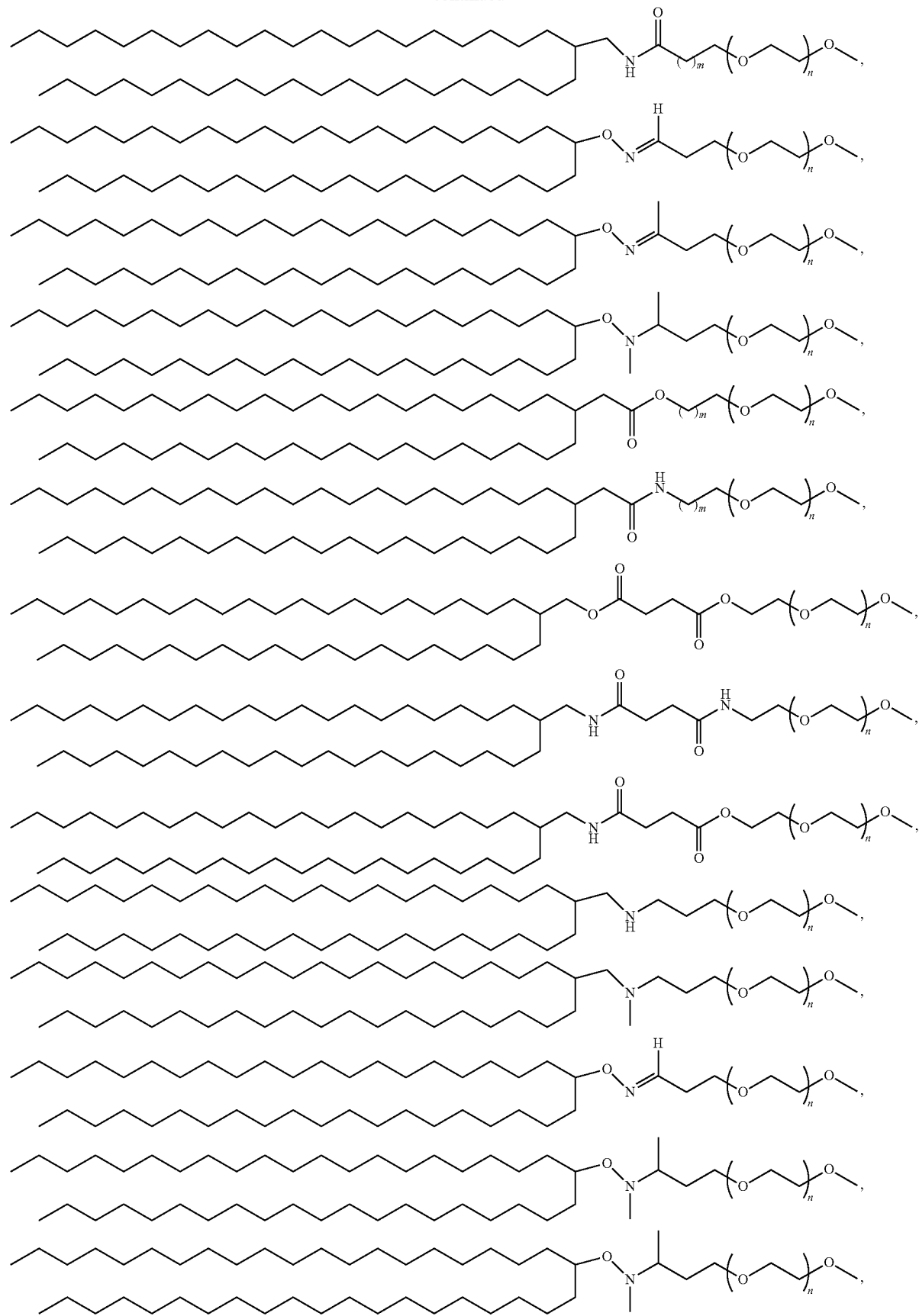

-continued
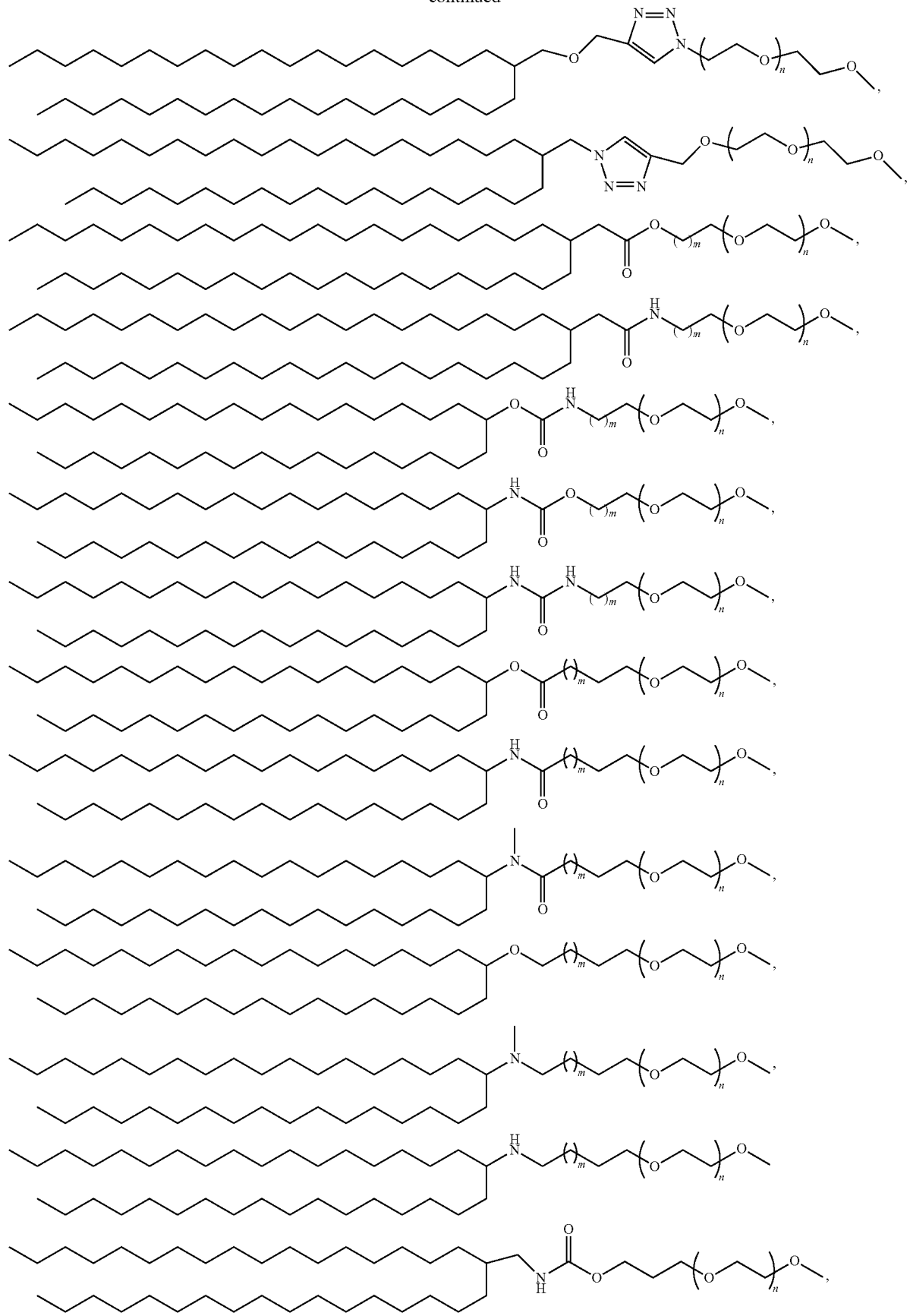

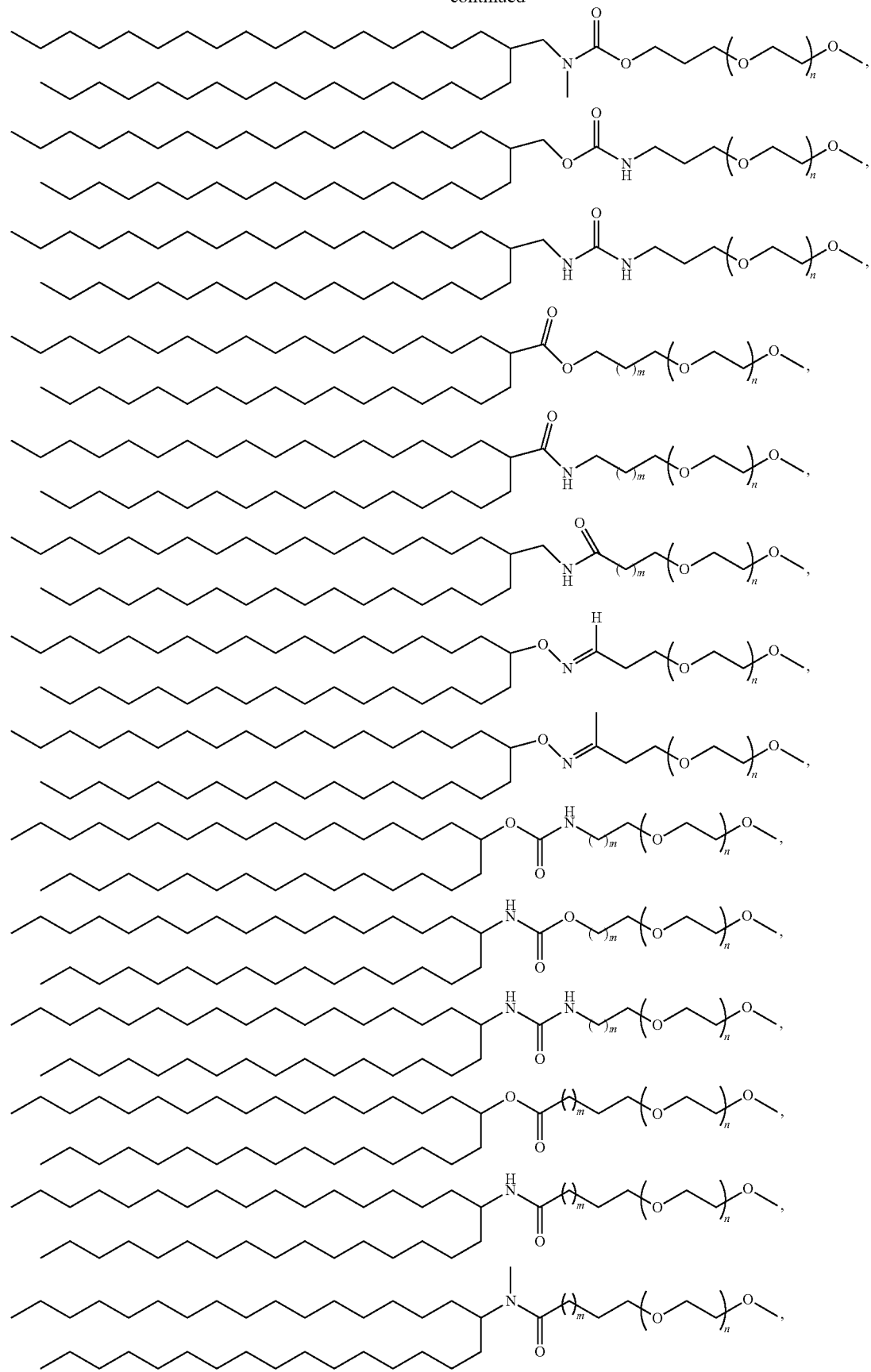

-continued
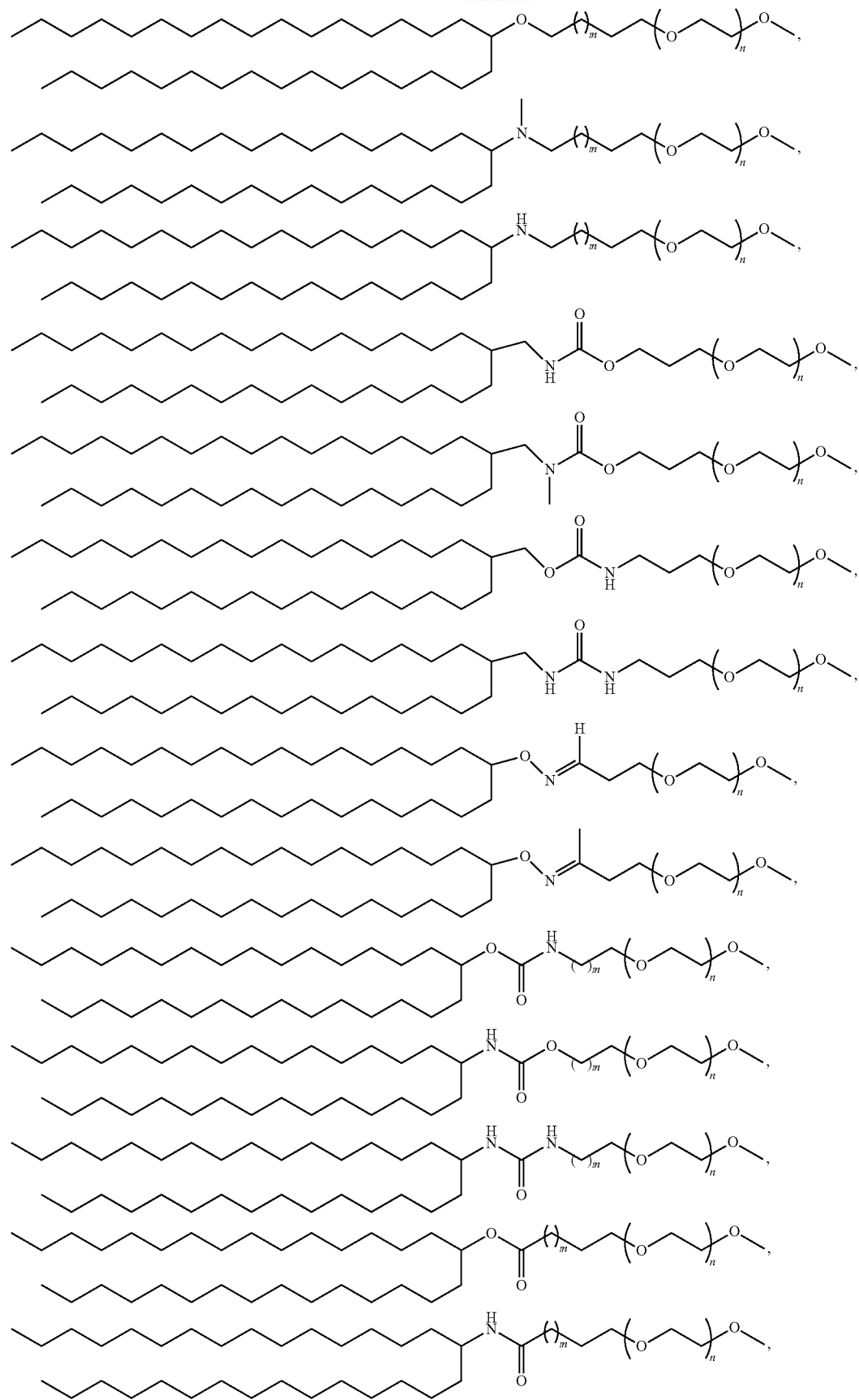

-continued
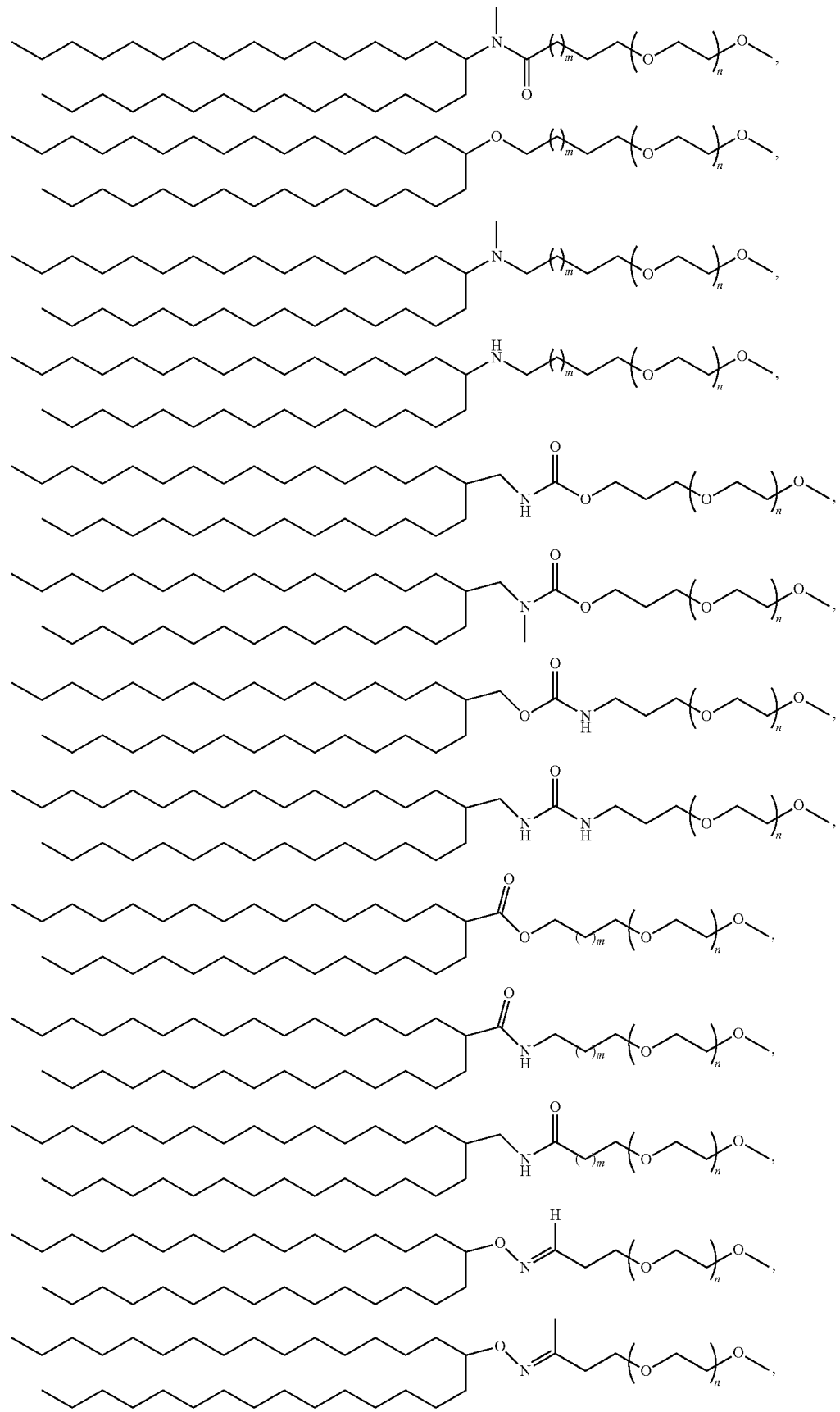

-continued
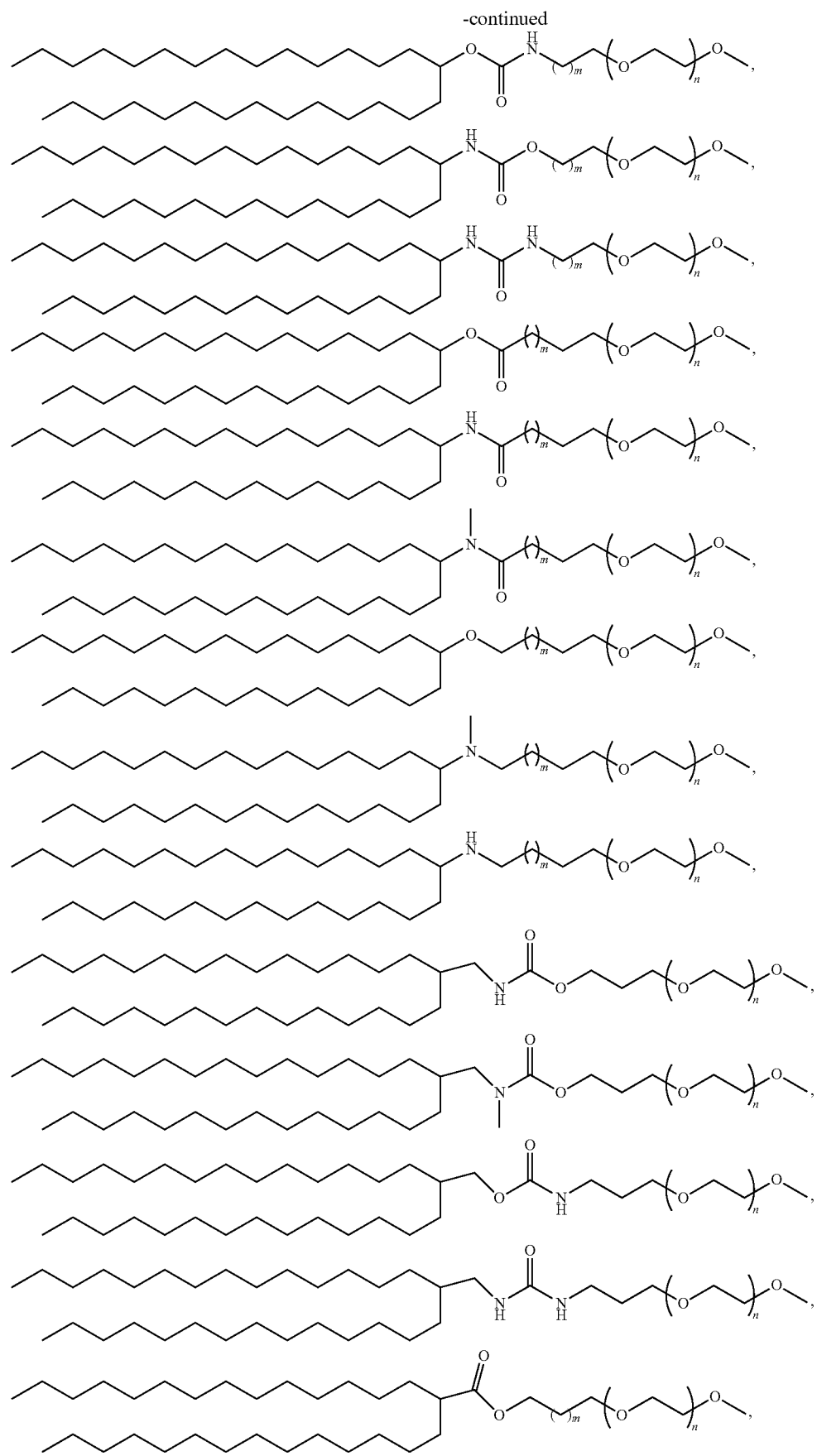

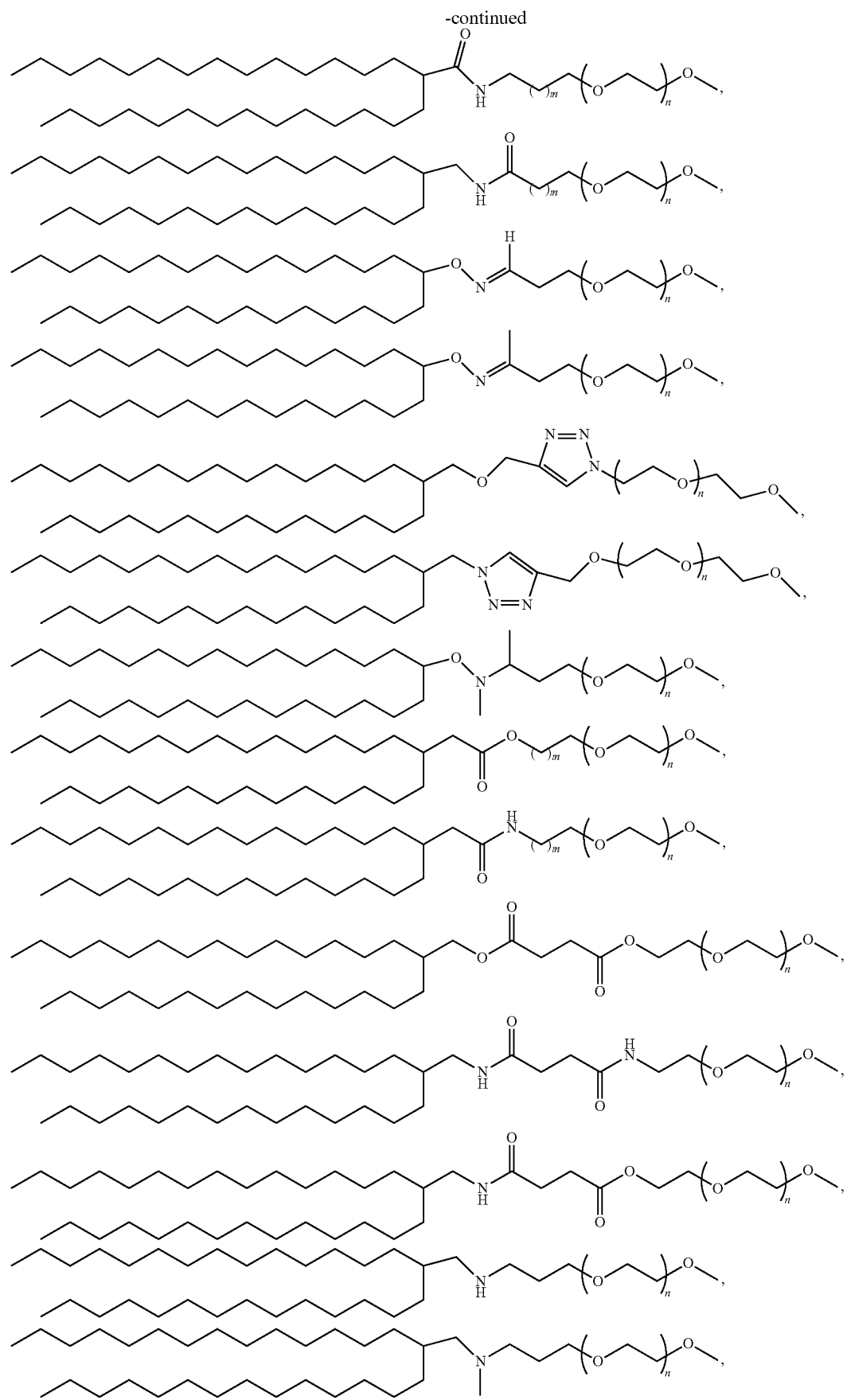

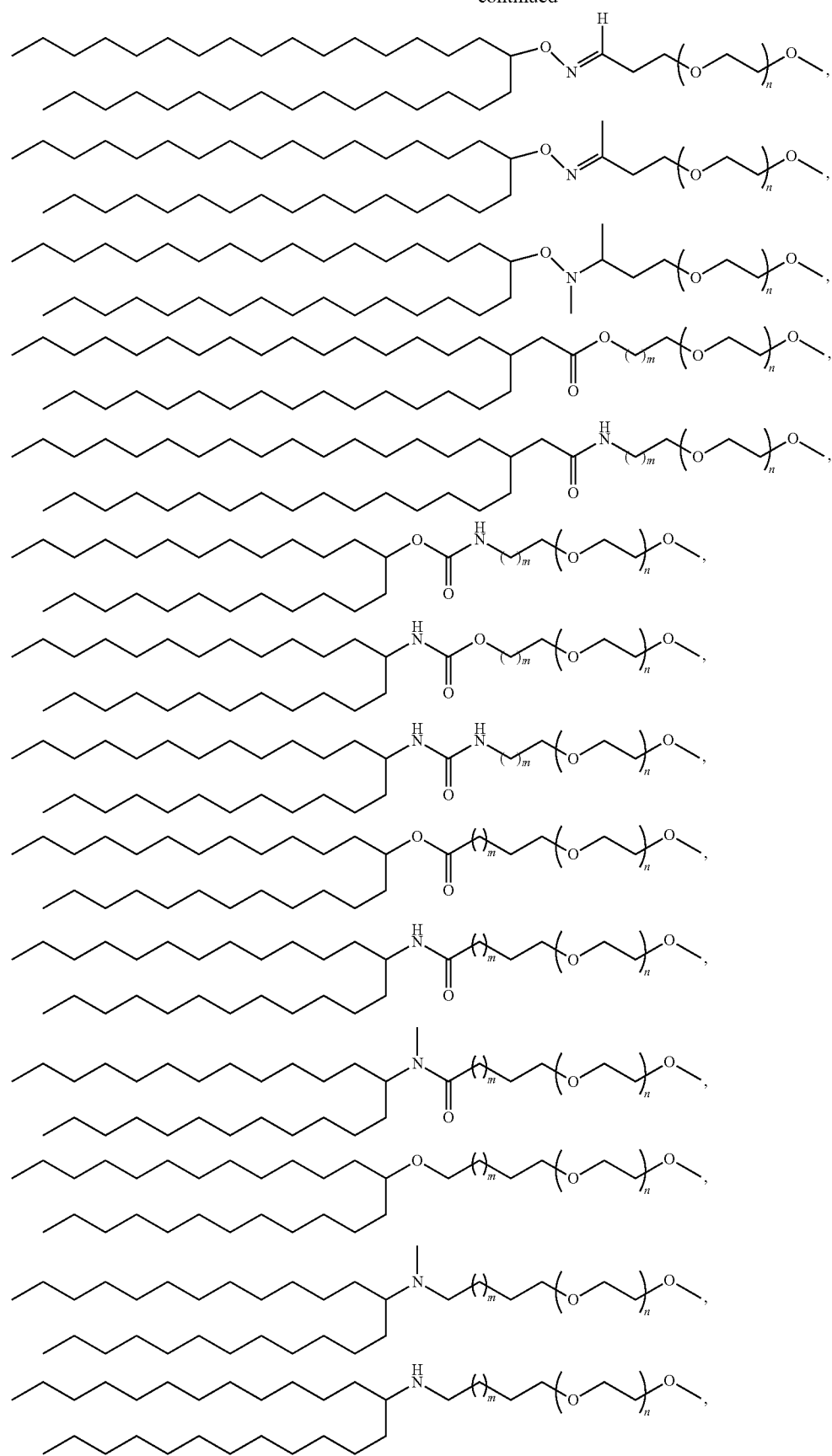

-continued
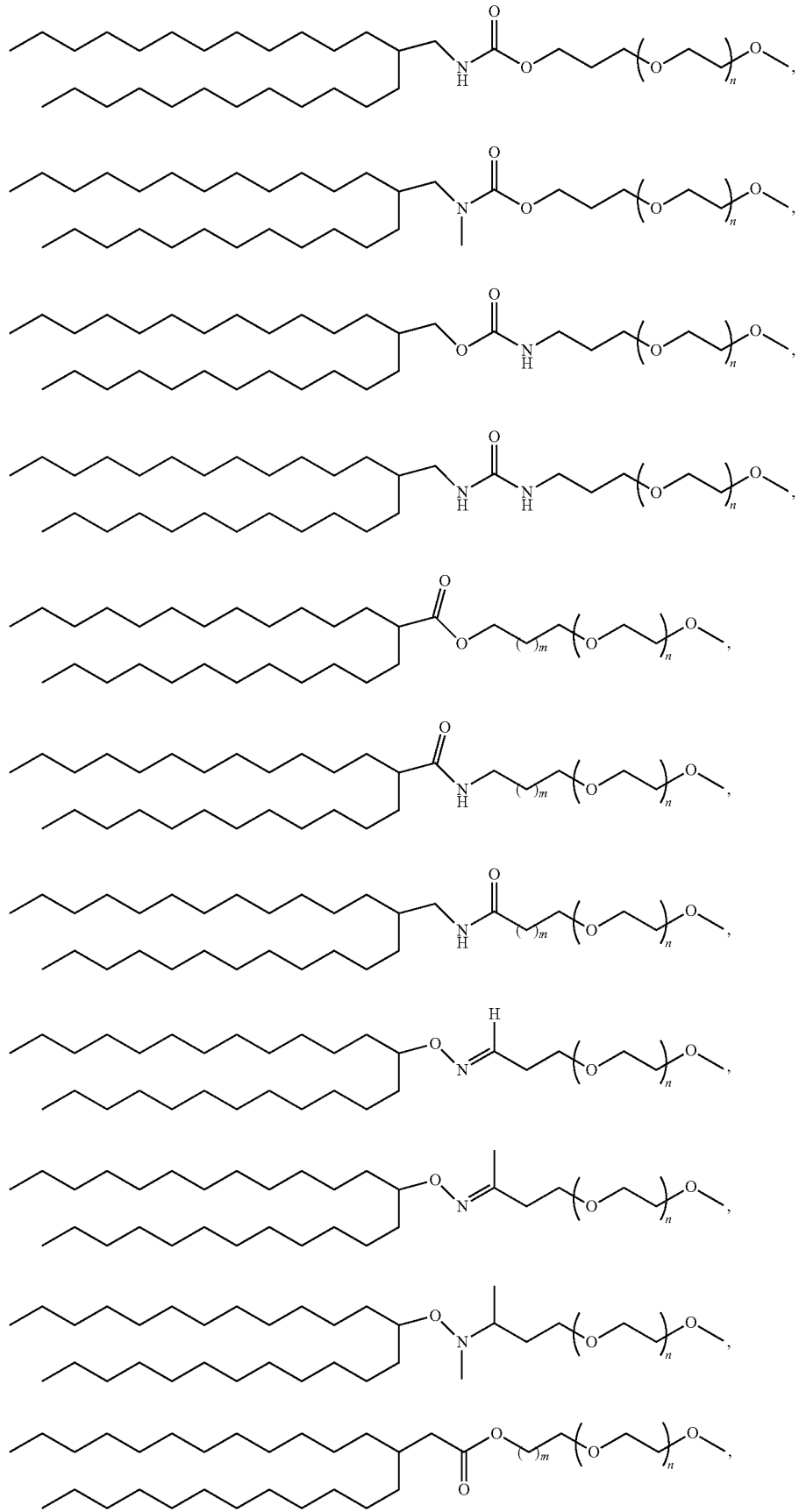

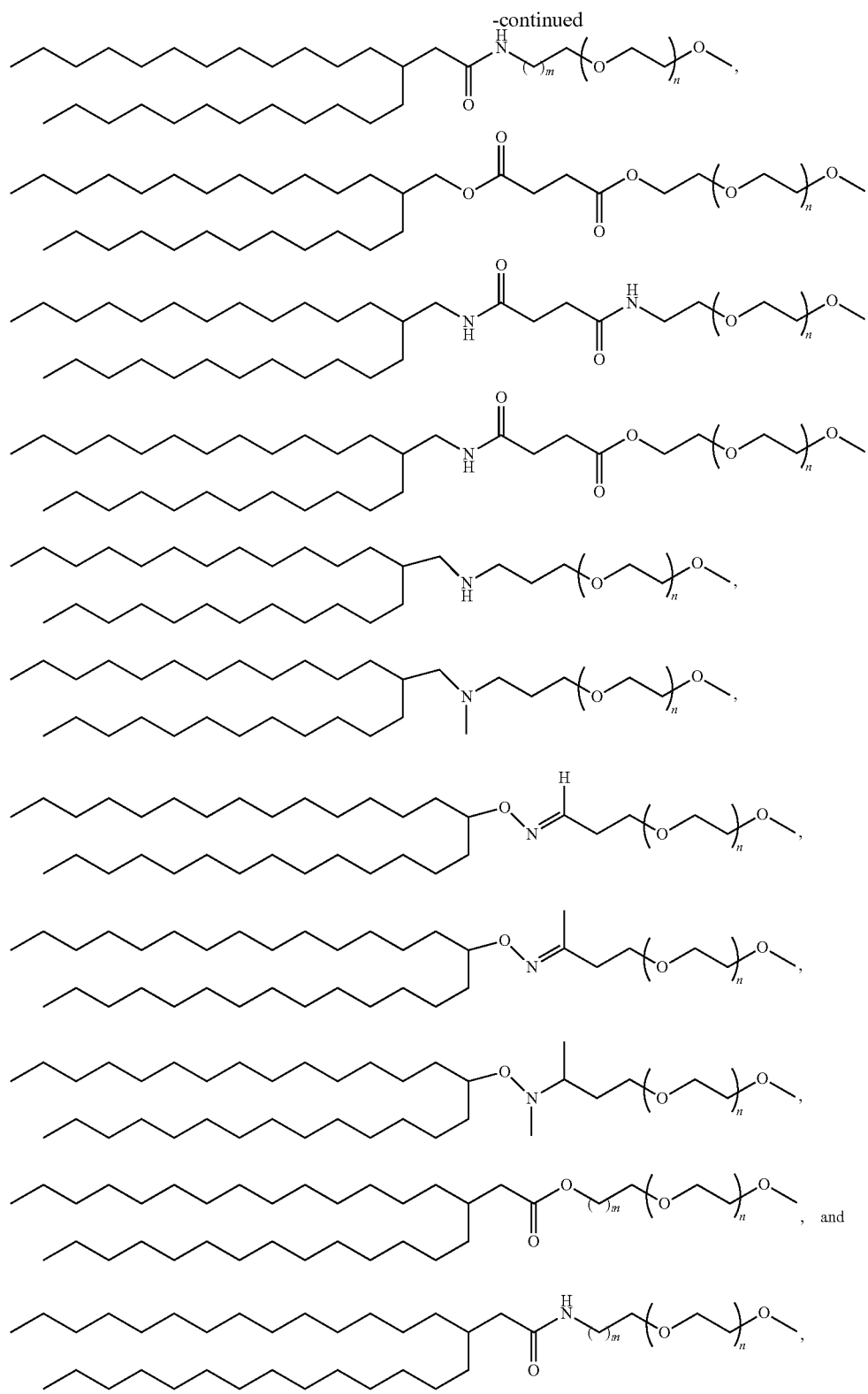

wherein
n is an integer from 1 to 1,000;
m is 0, 1, 2, 3, 4, 5, or 6;
and pharmaceutically acceptable salts thereof.

In one embodiment, n is from about 10 to about 500. In another embodiment, n is from about 30 to about 60.

Schemes 1-4 shown below describe synthetic methods for the preparation of Compounds A and B. Other compounds of formula (I) may be prepared by the methods shown in Schemes 1-4, using appropriately starting materials.

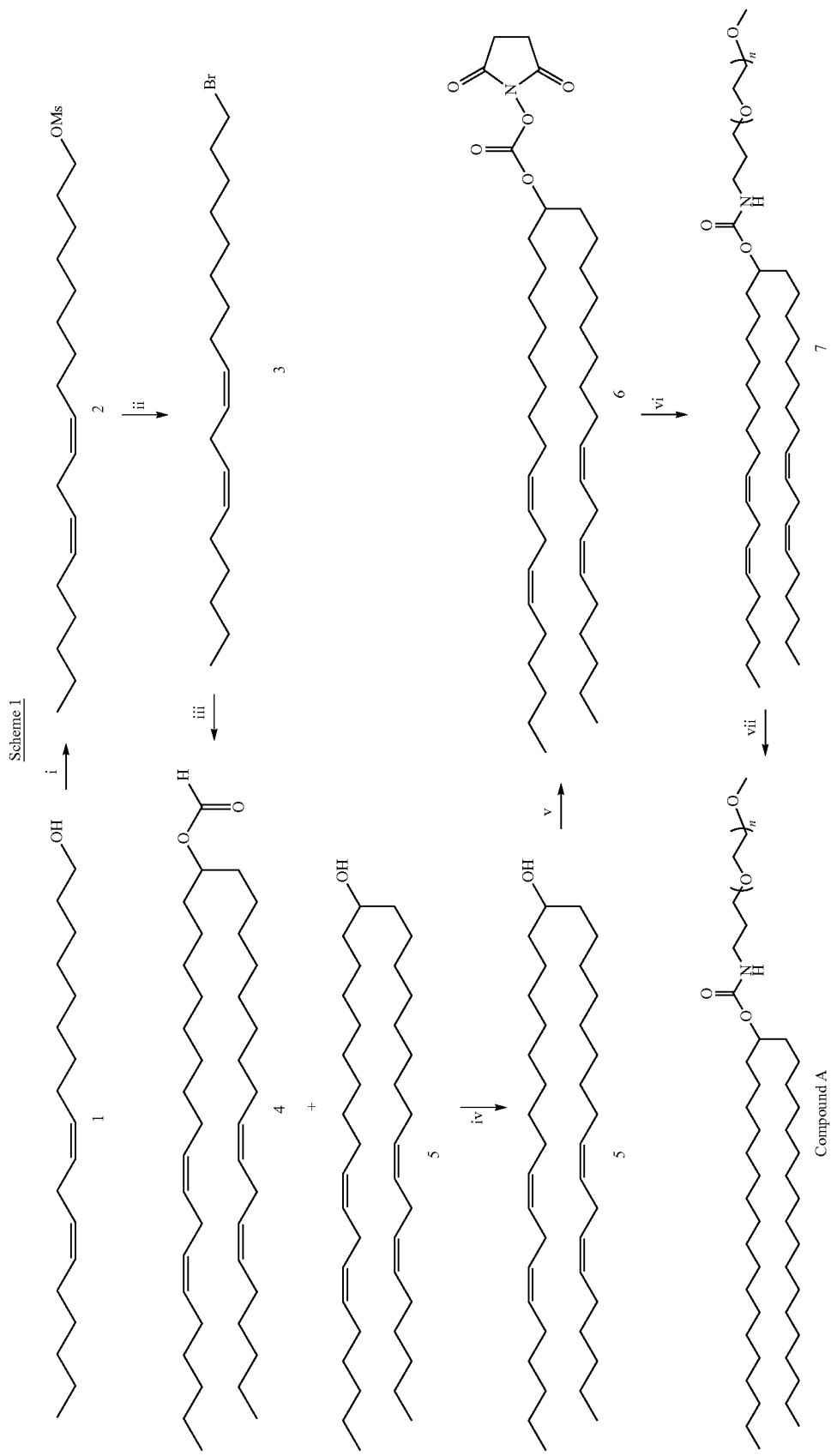

In Scheme I, the alcohol group of an aliphatic alcohol 1 is converted to a methoxy group to form compound 2. The methoxy group in compound 2 is converted to a leaving group (e.g., bromine) to form compound 3. Compound 3 is than reacted to form a compound with two aliphatic groups and a hydroxy group off a central atom (compound 5). The hydroxy group in compound 5 is then converted into the desired functional group (i.e., -L-$(A)_b$-$R^3$). The aliphatic group may subsequently be saturated (for example, to convert compound 7 to compound A).

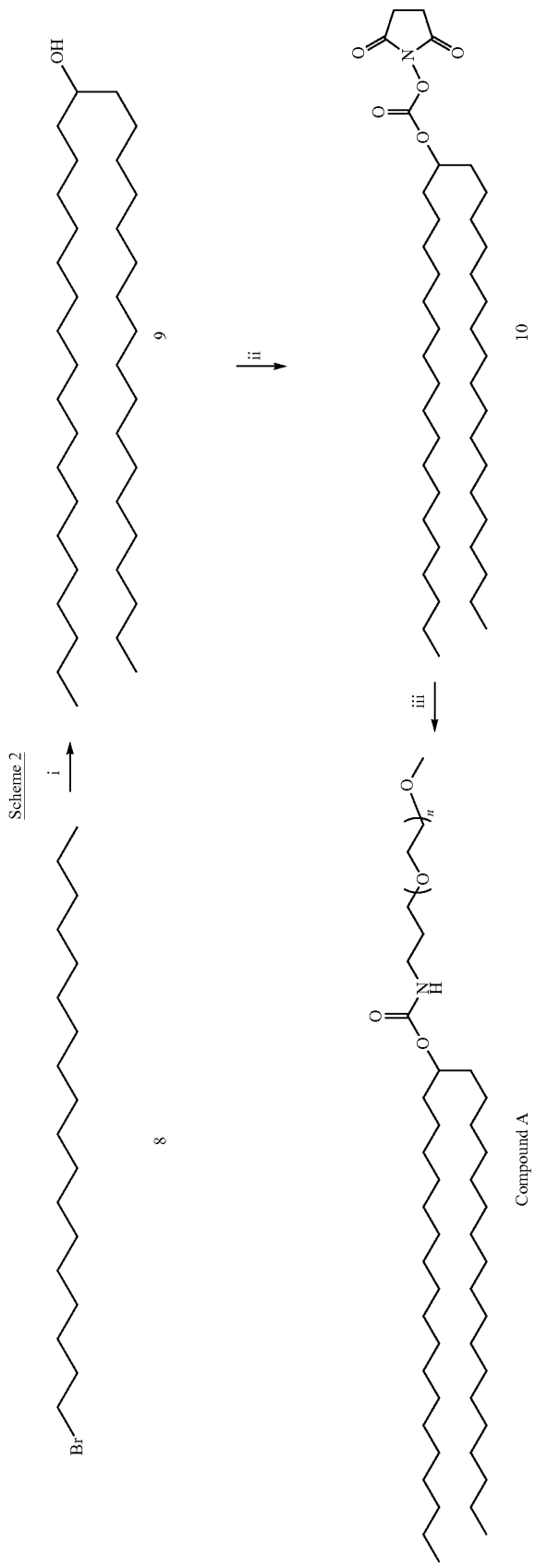

In Scheme 2, compound 9, an aliphatic compound with a terminal bromine, is reacted to form a compound with two aliphatic groups and a hydroxy group off a central atom (compound 5). The hydroxy group in compound 9 is then converted into the desired functional group (i.e., -L-$(A)_b$-$R^3$).

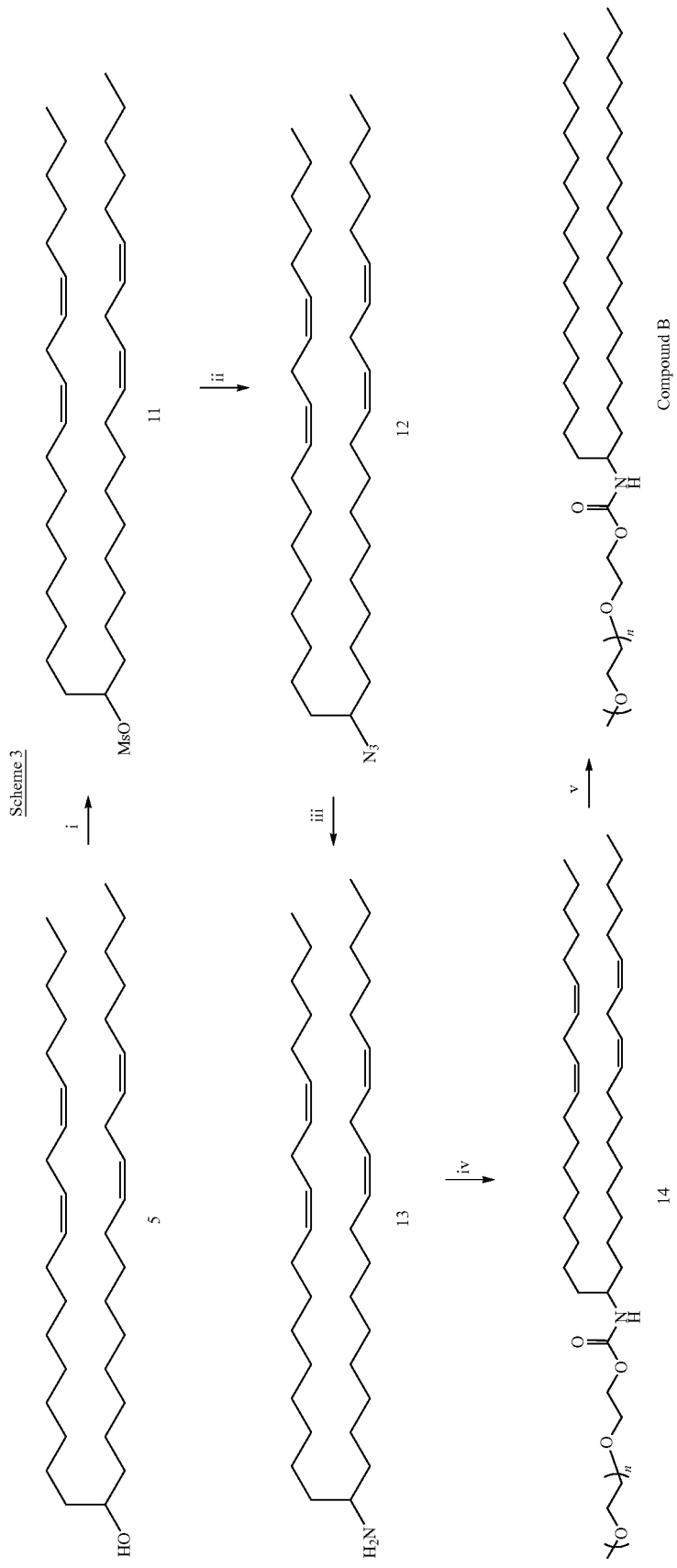
Scheme 3
i) MsCl, TEA, DCM; ii) NaN₃, DMF; iii) LAH, THF iv) Py, PEG—DSC; v) Pd—C, MeOH In Scheme 3, the alcohol group of a compound having two aliphatic groups and an alcohol on a central atom (compound 5) is converted to a methoxy group. The methoxy group is then converted to an azide ($N_3$) (compound 12) which is subsequently hydrolyzed to form an amino group (compound 13). The amino group may then be converted to the desired functional group (i.e., -L-(A)$_b$-R$^3$).

Lipid particles can include two or more cationic lipids. The lipids can be selected to contribute different advantageous properties. For example, cationic lipids that differ in properties such as amine $pK_a$, chemical stability, half-life in circulation, half-life in tissue, net accumulation in tissue, or toxicity can be used in a lipid particle. In particular, the cationic lipids can be chosen so that the properties of the

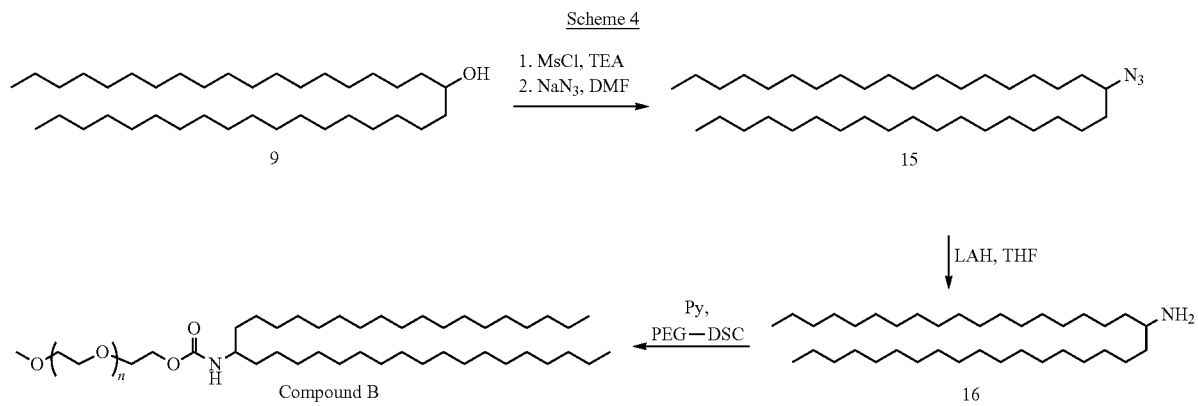

In Scheme 4, the alcohol group of a compound having two aliphatic groups and an alcohol on a central atom (compound 9) is converted to an azide group (compound 15). The azide group is hydrolyzed to form an amino group (compound 16). The amino group may then be converted to the desired functional group (i.e., -L-(A)$_b$-R$^3$).

Lipid Particles

In another aspect, the present invention relates to a lipid particle that includes a compound of formula (I). Lipid particles can also include one or more of the cationic lipids which are described in greater detail below. The lipid particles can further include one or more of: a second amino lipid or cationic lipid, a neutral lipid, a sterol, and a lipid selected to reduce aggregation of lipid particles, i.e., an aggregation-reducing lipid. Lipid particles include, but are not limited to, liposomes. As used herein, a liposome is a structure having lipid-containing membranes enclosing an aqueous interior. Liposomes may have one or more lipid membranes. Liposomes can be single-layered, referred to as unilamellar, or multi-layered, referred to as multilamellar. When complexed with nucleic acids, lipid particles may also be lipoplexes, which are composed of cationic lipid bilayers sandwiched between DNA layers, as described.

The lipid particles can also include one or more additional lipids and/or other components, such as cholesterol. Other lipids may be included in the liposome compositions for a variety of purposes, such as to prevent lipid oxidation or to attach ligands onto the liposome surface. Any of a number of lipids may be present in liposomes, including amphipathic, neutral, cationic, and anionic lipids. Such lipids can be used alone or in combination. Specific examples of additional lipid components that may be present are described below.

Additional components that may be present in a lipid particle include bilayer stabilizing components such as polyamide oligomers (see, e.g., U.S. Pat. No. 6,320,017), peptides, proteins, detergents, lipid-derivatives, such as PEG coupled to phosphatidylethanolamine and PEG conjugated to ceramides (see, for example, U.S. Pat. No. 5,885,613).

mixed-lipid particle are more desirable than the properties of a single-lipid particle of individual lipids.

Cationic Lipids

In certain embodiments, the lipids are cationic lipids. As used herein, the term "cationic lipid" is meant to include those lipids having one or two fatty acid or fatty aliphatic chains and an amino head group (including an alkylamino or dialkylamino group) that may be protonated to form a cationic lipid at physiological pH. In some embodiments, a cationic lipid is referred to as an "amino lipid."

Cationic lipids can have certain design features including a head group, one or more hydrophobic tails, and a linker between the head group and the one or more tails. The head group can include an amine. Under certain conditions, the amine nitrogen can be a site of positive charge. For example, when the amine is a primary, secondary, or tertiary amine, the amine will have a characteristic $pK_a$; in other words, it will undergo reversible protonation in aqueous media. The extent of positive charge is a function of the $pK_a$ and the pH of the aqueous media. The amine can also be a quaternary amine, in which case it will bear a positive charge regardless of whether it is in pure form, in aqueous media, or the pH of the aqueous media.

The $pK_a$ can be influenced by the structure of the lipid, particularly the nature of head group; e.g., the presence, absence, and location of functional groups such as anionic functional groups, hydrogen bond donor functional groups, hydrogen bond acceptor groups, hydrophobic groups (e.g., aliphatic groups), hydrophilic groups (e.g., hydroxyl or methoxy), or aryl groups. The head group amine can be a cationic amine; a primary, secondary, tertiary, or quaternary amine; the head group can include one amine group (monoamine), two amine groups (diamine), three amine groups (triamine), or a larger number of amine groups, as in an oligoamine or polyamine. The head group can include a functional group that is less strongly basic than an amine, such as, for example, an imidazole, a pyridine, or a guanidinium group. The head group can be zwitterionic.

The one or more hydrophobic tails can include two hydrophobic chains, which may be the same or different.

The tails can be aliphatic; for example, they can be composed of carbon and hydrogen, either saturated or unsaturated but without aromatic rings (e.g., $C_{10}$ to $C_{30}$ alkyl or $C_{10}$ to $C_{30}$ alkenyl). The tails can be fatty acid tails; some such groups include, but are not limited to, octanyl, nonanyl, decyl, lauryl, myristyl, palmityl, stearyl, α-linoleyl, stearidonyl, linoleyl, γ-linolenyl, arachadonyl, oleyl, and others.

The linker can include, for example, a glyceride linker, an acyclic glyceride analog linker, or a cyclic linker (including a spiro linker, a bicyclic linker, and a polycyclic linker). The linker can include functional groups such as, but not limited to, an ether, an ester, a phosphate, a phosphonate, a phosphorothioate, a sulfonate, a disulfide, an acetal, a ketal, an imine, a hydrazone, or an oxime.

The cationic lipid can include one or more biodegradable bonds. The biodegradable bonds can undergo bond breaking reactions in a biological environment, e.g., in an organism, organ, tissue, cell, or organelle. Some functional groups including biodegradable bonds include, for example, esters, dithiols, and oximes. Biodegradation can be a factor that influences the clearance of the compound from the body when administered to a subject. Biodegredation can be measured in a cell based assay, where a formulation including a cationic lipid is exposed to cells, and samples taken at various time points. The lipid fractions are extracted from the cells and separated and analyzed by LC-MS. From the LC-MS data, rates of biodegradation (e.g., as $t_{1/2}$ values) can be measured.

A number of cationic lipids, and methods for making them, are described in, for example, in International Publication Nos. WO 2010/054401, WO 2010/054401, WO 2010/054405, and WO 2010/054384, WO 2009/086558 and WO 2008/042973, and applications referred to therein, including nos. U.S. Provisional Application Nos. 61/104,219, filed Oct. 9, 2008; No. 61/113,179, filed Nov. 10, 2008; No. 61/154,350, filed Feb. 20, 2009; No. 61/171,439, filed Apr. 21, 2009; No. 61/175,770, filed May 5, 2009; No. 61/185,438, filed Jun. 9, 2009; No. 61/225,898, filed Jul. 15, 2009; and No. 61/234,098, filed Aug. 14, 2009. See, for example, Table 1 of International Publication No. WO 2010/054401 at pages 16-21.

Other cationic lipids include, for example, those having alternative fatty acid groups and other dialkylamino groups, including those in which the alkyl substituents are different (e.g., N-ethyl-N-methylamino-, N-propyl-N-ethylamino- and the like). For those embodiments in which the fatty groups are long chain alkyl, alkenyl, alkynyl, or acyl groups, they can be the same or different. In general, lipids (e.g., a cationic lipid) having less-saturated acyl chains are more easily sized, particularly when the complexes are sized below about 0.3 microns, for purposes of filter sterilization. Cationic lipids containing unsaturated fatty acids with carbon chain lengths in the range of $C_{10}$ to $C_{20}$ are typical. Other scaffolds can also be used to separate the amino group (e.g., the amino group of the cationic lipid) and the fatty acid or fatty alkyl portion of the cationic lipid. Suitable scaffolds are known to those of skill in the art.

In certain embodiments, cationic lipids have at least one protonatable or deprotonatable group, such that the lipid is positively charged at a pH at or below physiological pH (e.g. pH 7.4), and neutral at a second pH, preferably at or above physiological pH. Such lipids are also referred to as cationic lipids. It will, of course, be understood that the addition or removal of protons as a function of pH is an equilibrium process, and that the reference to a charged or a neutral lipid refers to the nature of the predominant species and does not require that all of the lipid be present in the charged or neutral form. The lipids can have more than one protonatable or deprotonatable group, or can be zwitterrionic.

In certain embodiments, protonatable lipids (i.e., cationic lipids) have a $pK_a$ of the protonatable group in the range of about 4 to about 11. Typically, lipids will have a $pK_a$ of about 4 to about 7, e.g., between about 5 and about 7, such as between about 5.5 and about 6.8, when incorporated into lipid particles. Such lipids will be cationic at a lower pH formulation stage, while particles will be largely (though not completely) surface neutralized at physiological pH around pH 7.4. One of the benefits of a $pK_a$ in the range of between about 4 and 7 is that at least some nucleic acid associated with the outside surface of the particle will lose its electrostatic interaction at physiological pH and be removed by simple dialysis; thus greatly reducing the particle's susceptibility to clearance. $pK_a$ measurements of lipids within lipid particles can be performed, for example, by using the fluorescent probe 2-(p-toluidino)-6-napthalene sulfonic acid (TNS), using methods described in Cullis et al., *Chem Phys Lipids* 40, 127-144 (1986).

In additional embodiments, the lipids are charged lipids. As used herein, the term "charged lipid" is meant to include those lipids having one or two fatty acyl or fatty alkyl chains and a quaternary amino head group. The quaternary amine carries a permanent positive charge. The head group can optionally include a ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine). In some embodiments, a charged lipid is referred to as an "amino lipid." See, for example, International Application No. PCT/US10/59206, filed Dec. 7, 2010.

Net tissue accumulation and long term toxicity (if any) from the cationic lipids can be modulated in a favorable way by choosing mixtures of cationic lipids instead of selecting a single cationic lipid in a given formulation. Such mixtures can also provide better encapsulation and/or release of the drug. A combination of cationic lipids also can affect the systemic stability when compared to single entity in a formulation. See, e.g., International Patent Application No. PCT/US10/61058, filed Dec. 17, 2010.

For example, a lipid particle can contain a mixture of the cationic lipids described in, e.g., International Publication No. WO 2009/086558 and U.S. Provisional Application No. 61/104,219, filed Oct. 9, 2008, and ester analogs thereof. In another example, a lipid particle can contain a mixture of a lipid, for example, Lipid A, described in International Publication No. WO 2010/088537, and a lipid, for example, the lipid of formula V or formula VI, described in U.S. Provisional Application No. 61/175,770, filed May 5, 2009.

Other cationic lipids, which carry a net positive charge at about physiological pH, in addition to those specifically described above, may also be included in lipid particles. Such cationic lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN® (including DOTMA and DOPE, available from Invitrogen™, Carlsbad, Calif.), and LIPOFECTAMINE® (comprising DOSPA and DOPE, available from Invitrogen™, Carlsbad, Calif.). In certain embodiments, a cationic lipid is an amino lipid.

Aggregation-Reducing Lipids

Examples of lipids that reduce aggregation of particles during formation include polyethylene glycol (PEG)-modified lipids, monosialoganglioside Gm1, and polyamide oligomers ("PAO") such as those described in U.S. Pat. No. 6,320,017). Other compounds with uncharged, hydrophilic, steric-barrier moieties, which prevent aggregation during formulation, like PEG, Gm1 or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to about 15% (by mole percent of lipids). Other lipids which reduce aggregation and/or include a PEG moiety are described in, for example, U.S. Pat. No. 7,803,397, and in International Publication No. WO 2009/082607.

Specific examples of PEG-modified lipids (or lipid-polyoxyethylene conjugates) that can have a variety of "anchoring" lipid portions to secure the PEG portion to the surface of the lipid vesicle include, but are not limited to, PEG-modified phosphatidylethanolamine and phosphatidic acid, PEG-ceramide conjugates (e.g., PEG-CerC14 or PEG-CerC20) which are described in U.S. Pat. No. 5,820,873, PEG-modified dialkylamines, PEG-modified 1,2-diacyloxypropan-3-amines, PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mPEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 min in some assays.

As illustrated in U.S. Pat. No. 5,820,873, at least three characteristics can influence the rate of exchange: length of acyl chain, saturation of acyl chain, and size of the steric-barrier head group. Compounds having suitable variations of these features may be useful. For some therapeutic applications it may be preferable for the PEG-modified lipid to be rapidly lost from the nucleic acid-lipid particle in vivo and hence the PEG-modified lipid will possess relatively short lipid anchors. In other therapeutic applications it may be preferable for the nucleic acid-lipid particle to exhibit a longer plasma circulation lifetime and hence the PEG-modified lipid will possess relatively longer lipid anchors.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

Neutral Lipids and Sterols

Neutral lipids, when present in the lipid particle, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. In certain embodiments, the neutral lipid component is a lipid having two acyl groups, (e.g., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids contain saturated fatty acids with carbon chain lengths in the range of $C_{10}$ to $C_{20}$. In another group of embodiments, lipids contain mono or diunsaturated fatty acids with carbon chain lengths in the range of $C_{10}$ to $C_{20}$. Additionally, lipids having mixtures of saturated and unsaturated fatty acid chains can be used. In certain embodiments, the neutral lipids used are DOPE, DSPC, POPC, DPPC or any related phosphatidylcholine. The neutral lipids may also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. In one embodiment, the sterol is cholesterol.

Anionic and Amphipathic Lipids

Anionic lipids suitable for use in lipid particles include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In additional embodiments, amphipathic lipids are included in lipid particles. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Fusion Promoting Lipids

Also suitable for inclusion in the lipid particles are programmable fusion lipids or fusion-promoting lipid. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. The fusion promoting-lipids can be, for example, compounds of formula (I) as described above. In some cases, the signal event can be a change in pH, for example, such as the difference in pH between an extracelluar environment and an intracellular environment, or between an intracellular environment and an endosomal environment.

When time is the signal event, a fusion delaying or "cloaking" component, such as an ATTA-lipid conjugate or a PEG-lipid conjugate, can simply exchange out of the lipid particle membrane over time. By the time the lipid particle is suitably distributed in the body, it has lost sufficient cloaking agent so as to be fusogenic. With other signal events, it can be desirable to choose a signal that is associated with the disease site or target cell, such as increased temperature at a site of inflammation.

In certain embodiments, it is desirable to target the lipid particles using targeting moieties that are specific to a cell type or tissue. Targeting of lipid particles using a variety of targeting moieties, such as ligands, cell surface receptors, glycoproteins, vitamins (e.g., riboflavin) and monoclonal antibodies, may be employed (see, e.g., U.S. Pat. Nos. 4,957,773 and 4,603,044). The targeting moieties can comprise the entire protein or fragments thereof. Targeting mechanisms generally require that the targeting agents be positioned on the surface of the lipid particle in such a manner that the target moiety is available for interaction with the target, for example, a cell surface receptor. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002).

The use of lipid particles, i.e., liposomes, with a surface coating of hydrophilic polymer chains, such as polyethylene glycol (PEG) chains, for targeting has been proposed (see, e.g., Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci.* (*USA*), 87:2448-2451 (1990). Other examples of antibody conjugation are disclosed in U.S. Pat. No. 6,027,726. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes,* 149 *Methods in Enzymology* 111-119 (Academic Press, Inc. 1987)). Other targeting methods include the biotin-avidin system.

Lipid Particle Formulations

In some embodiments, the lipid particle includes a mixture of a cationic lipid and a fusion-promoting lipid. The lipid particle can further include a neutral lipid, a sterol, an aggregation-reducing lipid, or a combination of these. For example, in one embodiment, the lipid particle can include a cationic lipid, a fusion-promoting lipid, and a neutral lipid, but no sterol or aggregation-reducing lipid. In another embodiment, the lipid particle can include a cationic lipid, a fusion-promoting lipid, and a neutral lipid, but no sterol or aggregation-reducing lipid. In another embodiment, the lipid particle can include a cationic lipid, a fusion-promoting lipid, and an aggregation-reducing lipid, but no sterol or neutral lipid. In another embodiment, the lipid particle can include a cationic lipid, a fusion-promoting lipid, a sterol, and a neutral lipid, but no aggregation-reducing lipid. In another embodiment, the lipid particle can include a cationic lipid, a fusion-promoting lipid, a sterol, and an aggregation-reducing lipid, but no neutral lipid. In another embodiment, the lipid particle can include a cationic lipid, a fusion-promoting lipid, a neutral lipid, and an aggregation-reducing lipid, but no sterol. In another embodiment, the lipid particle can include a cationic lipid, a fusion-promoting lipid, a sterol, neutral lipid, and an aggregation-reducing lipid.

In one exemplary embodiment, the lipid particle comprises a mixture of a cationic lipid, a fusion-promoting lipid, neutral lipids (other than a cationic lipid), a sterol (e.g., cholesterol) and an aggregation-reducing lipid (e.g., a compound of formula (I), a PEG-DMG or PEG-DMA). In certain embodiments, the lipid mixture consists of or consists essentially of a cationic lipid, a fusion-promoting lipid, a neutral lipid, cholesterol, and an aggregation-reducing lipid. In further embodiments, the lipid particle includes the above lipid mixture in mole percentages of about 20-70% cationic lipid: about 0.1-50% fusion promoting lipid: about 5-45% neutral lipid: about 20-55% cholesterol: about 0.5-15% aggregation-reducing lipid. In some embodiments, the fusion-promoting lipid can be present in a mole percentage of about 0.1-50%, about 0.5-50%, about 1-50%, about 5%-45%, about 10%-40%, or about 15%-35%. In some embodiments, the fusion-promoting lipid can be present in a mole percentage of about 0.1-50%, about 0.5-50%, about 1-50%, about 5%-45%, about 10%-40%, or about 15%-35%. In some embodiments, the fusion-promoting lipid can be present in a mole percentage of about 0.1-50%, about 10-50%, about 20-50%, or about 30-50%. In some embodiments, the fusion-promoting lipid can be present in a mole percentage of about 0.1-50%, about 0.5-45%, about 1-40%, about 1%-35%, about 1%-30%, or about 1%-20%.

In further embodiments, the lipid particle consists of or consists essentially of the above lipid mixture in mole percentages of about 20-70% cationic lipid: about 0.1-50% fusion promoting lipid: about 5-45% neutral lipid: about 20-55% cholesterol: about 0.5-15% aggregation-reducing lipid.

In particular embodiments, the lipid particle comprises, consists of, or consists essentially of a mixture of one or more cationic lipids, DSPC, Chol, and an aggregation-reducing lipid, e.g., in mole percentages of about 20-60% cationic lipid: about 0.1-50% fusion promoting lipid: about 5-25% DSPC: about 25-55% cholesterol: about 0.5-15% aggregation-reducing lipid. In particular embodiments, the molar lipid ratio (with regard to mol % cationic lipid/DSPC/cholesterol/aggregation-reducing lipid) is approximately about 40/10/40/10, about 35/15/40/10 or about 52/13/30/5; this mixture can be further combined with a fusion-promoting lipid in a mole percentage of about 0.1-50%, about 0.1-50%, about 0.5-50%, about 1-50%, about 5%-45%, about 10%-40%, or about 15%-35%. In other words, when an about 40/10/40/10 mixture of lipid/DSPC/cholesterol/aggregation-reducing lipid is combined with a fusion-promoting peptide in a mole percentage of about 50%, the resulting lipid particles can have a total molar ratio of (mol % cationic lipid/DSPC/cholesterol/aggregation-reducing lipid/fusion-promoting peptide) about 20/5/20/5/50. In another group of embodiments, the neutral lipid, DSPC, in these compositions is replaced with POPC, DPPC, DOPE or SM.

Apolipoproteins

The formulations can further comprise an apolipoprotein. As used herein, the term "apolipoprotein" or "lipoprotein" refers to apolipoproteins known to those of skill in the art and variants and fragments thereof and to apolipoprotein agonists, analogues or fragments thereof described below.

Suitable apolipoproteins include, but are not limited to, ApoA-I, ApoA-II, ApoA-IV, ApoA-V and ApoE, and active polymorphic forms, isoforms, variants and mutants as well as fragments or truncated forms thereof. In certain embodiments, the apolipoprotein is a thiol containing apolipoprotein. "Thiol containing apolipoprotein" refers to an apolipoprotein, variant, fragment or isoform that contains at least one cysteine residue. The most common thiol containing apolipoproteins are ApoA-I Milano (ApoA-$I_M$) and ApoA-I Paris (ApoA-$I_P$) which contain one cysteine residue (Jia et al., 2002, *Biochem. Biophys. Res. Comm.*, 297: 206-13; Bielicki and Oda, 2002, *Biochemistry*, 41: 2089-96). ApoA-II, ApoE2 and ApoE3 are also thiol containing apolipoproteins. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; and 5,116,739. ApoE3 is disclosed in Weisgraber, et al., *J. Biol. Chem.*, (1981) 256: 9077-9083; and Rall, et al., *Proc. Nat. Acad. Sci.*, (1982) 79: 4696-4700. See also GenBank accession number K00396.

In certain embodiments, the apolipoprotein can be in its mature form, in its preproapolipoprotein form or in its proapolipoprotein form. Homo- and hetero-dimers (where feasible) of pro- and mature ApoA-I (Duverger et al., 1996, *Arterioscler. Thromb. Vasc. Biol.*, 16(12):1424-29), ApoA-I Milano (Klon et al., 2000, *Biophys. J.*, 79:(3)1679-87; Franceschini et al., 1985, J. Biol. Chem., 260: 1632-35), ApoA-I Paris (Daum et al., 1999, *J. Mol. Med.*, 77:614-22), ApoA-II (Shelness et al., 1985, *J. Biol. Chem.*, 260(14): 8637-46; Shelness et al., 1984, *J. Biol. Chem.*, 259(15): 9929-35), ApoA-IV (Duverger et al., 1991, *Euro. J. Biochem.* 201(2):373-83), and ApoE (McLean et al., 1983, *J. Biol. Chem.*, 258(14):8993-9000) can also be utilized.

In certain embodiments, the apolipoprotein can be a fragment, variant or isoform of the apolipoprotein. The term "fragment" refers to any apolipoprotein having an amino acid sequence shorter than that of a native apolipoprotein and which fragment retains the activity of native apolipoprotein, including lipid binding properties. By "variant" is meant substitutions or alterations in the amino acid sequences of the apolipoprotein, which substitutions or alterations, e.g., additions and deletions of amino acid residues, do not abolish the activity of native apolipoprotein, including lipid binding properties. Thus, a variant can comprise a protein or peptide having a substantially identical amino acid sequence to a native apolipoprotein provided herein in which one or more amino acid residues have been conservatively substituted with chemically similar amino acids. Examples of conservative substitutions include the substitution of at least one hydrophobic residue such as, for example, isoleucine, valine, leucine or methionine for another. Likewise, for example, the substitution of at least one hydrophilic residue such as, for example, between arginine and lysine, between glutamine and asparagine, and between glycine and serine (see U.S. Pat. Nos. 6,004,925, 6,037,323 and 6,046,166) are conservative substitutions. The term "isoform" refers to a protein having the same, greater or partial function and similar, identical or partial sequence, and may or may not be the product of the same gene and usually tissue specific (see Weisgraber 1990, *J. Lipid Res.* 31(8):1503-11; Hixson and Powers 1991, *J. Lipid Res.* 32(9):1529-35; Lackner et al., 1985, *J. Biol. Chem.* 260(2):703-6; Hoeg et al., 1986, *J. Biol. Chem.* 261(9):3911-4; Gordon et al., 1984, *J. Biol. Chem.* 259(1):468-74; Powell et al., 1987, *Cell* 50(6):831-40; Aviram et al., 1998, *Arterioscler. Thromb. Vasc. Biol.* 18(10):1617-24; Aviram et al., 1998, *J. Clin. Invest.* 101(8):1581-90; Billecke et al., 2000, *Drug Metab. Dispos.* 28(11):1335-42; Draganov et al., 2000, *J. Biol. Chem.* 275(43):33435-42; Steinmetz and Utermann 1985, *J. Biol. Chem.* 260(4):2258-64; Widler et al., 1980, *J. Biol. Chem.* 255(21):10464-71; Dyer et al., 1995, *J. Lipid Res.* 36(1):80-8; Sacre et al., 2003, *FEBS Lett.* 540(1-3): 181-7; Weers, et al., 2003, *Biophys. Chem.* 100(1-3):481-92; Gong et al., 2002, *J. Biol. Chem.* 277(33):29919-26; Ohta et al., 1984, *J. Biol. Chem.* 259(23):14888-93 and U.S. Pat. No. 6,372,886).

In certain embodiments, the methods and compositions described herein include the use of a chimeric construction of an apolipoprotein. For example, a chimeric construction of an apolipoprotein can be comprised of an apolipoprotein domain with high lipid binding capacity associated with an apolipoprotein domain containing ischemia reperfusion protective properties. A chimeric construction of an apolipoprotein can be a construction that includes separate regions within an apolipoprotein (i.e., homologous construction) or a chimeric construction can be a construction that includes separate regions between different apolipoproteins (i.e., heterologous constructions). Compositions comprising a chimeric construction can also include segments that are apolipoprotein variants or segments designed to have a specific character (e.g., lipid binding, receptor binding, enzymatic, enzyme activating, antioxidant or reduction-oxidation property) (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al, 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sorenson et al., 1999, Arterioscler. Thromb. Vasc. Biol. 19(9):2214-25; Palgunachari 1996, Arterioscler. Throb. Vasc. Biol. 16(2):328-38: Thurberg et al., J. Biol. Chem. 271(11):6062-70; Dyer 1991, J. Biol. Chem. 266(23): 150009-15; Hill 1998, J. Biol. Chem. 273(47):30979-84).

In additional embodiments, apolipoproteins utilized in the present invention also include recombinant, synthetic, semisynthetic or purified apolipoproteins. Methods for obtaining apolipoproteins or equivalents thereof are well-known in the art. For example, apolipoproteins can be separated from plasma or natural products by, for example, density gradient centrifugation or immunoaffinity chromatography, or produced synthetically, semi-synthetically or using recombinant DNA techniques known to those of the art (see, e.g., Mulugeta et al., 1998, J. Chromatogr. 798(1-2): 83-90; Chung et al., 1980, J. Lipid Res. 21(3):284-91; Cheung et al., 1987, J. Lipid Res. 28(8):913-29; Persson, et al., 1998, J. Chromatogr. 711:97-109; U.S. Pat. Nos. 5,059,528, 5,834, 596, 5,876,968 and 5,721,114; and PCT Publications WO 86/04920 and WO 87/02062).

Apolipoproteins may further include apolipoprotein agonists, such as peptides and peptide analogues that mimic the activity of ApoA-I, ApoA-I Milano (ApoA-$I_M$), ApoA-I Paris (ApoA-$I_P$), ApoA-II, ApoA-IV, and ApoE. For example, the apolipoprotein can be any of those described in U.S. Pat. Nos. 6,004,925, 6,037,323, 6,046,166, and 5,840, 688.

Apolipoprotein agonist peptides or peptide analogues can be synthesized or manufactured using any technique for peptide synthesis known in the art including, e.g., the techniques described in U.S. Pat. Nos. 6,004,925, 6,037,323 and 6,046,166. For example, the peptides may be prepared using the solid-phase synthetic technique initially described by Merrifield (1963, *J. Am. Chem. Soc.* 85:2149-2154). Other peptide synthesis techniques may be found in Bodanszky et al., Peptide Synthesis, John Wiley & Sons, 2d Ed., (1976) and other references readily available to those skilled in the art. A summary of polypeptide synthesis techniques can be found in Stuart and Young, Solid Phase Peptide. Synthesis, Pierce Chemical Company, Rockford, Ill., (1984). Peptides may also be synthesized by solution methods as described in The Proteins, Vol. II, 3d Ed., Neurath et. al., Eds., p. 105-237, Academic Press, New York, N.Y. (1976). Appropriate protective groups for use in different peptide syntheses are described in the above-mentioned texts as well as in McOmie, Protective Groups in Organic Chemistry, Plenum Press, New York, N.Y. (1973). The peptides might also be prepared by chemical or enzymatic cleavage from larger portions of, for example, apolipoprotein A-I.

In certain embodiments, the apolipoprotein can be a mixture of apolipoproteins. In one embodiment, the apolipoprotein can be a homogeneous mixture, that is, a single type of apolipoprotein. In another embodiment, the apolipoprotein can be a heterogeneous mixture of apolipoproteins, that is, a mixture of two or more different apolipoproteins. Embodiments of heterogenous mixtures of apolipoproteins can comprise, for example, a mixture of an apolipoprotein from an animal source and an apolipoprotein from a semi-synthetic source. In certain embodiments, a heterogenous mixture can comprise, for example, a mixture of ApoA-I and ApoA-I Milano. In certain embodiments, a heterogeneous mixture can comprise, for example, a mixture of ApoA-I Milano and ApoA-I Paris. Suitable mixtures for use in the methods and compositions described herein will be apparent to one of skill in the art.

If the apolipoprotein is obtained from natural sources, it can be obtained from a plant or animal source. If the apolipoprotein is obtained from an animal source, the apolipoprotein can be from any species. In certain embodiments, the apolipoprotein can be obtained from an animal source. In certain embodiments, the apolipoprotein can be obtained from a human source. In preferred embodiments, the apolipoprotein is derived from the same species as the individual to which the apolipoprotein is administered.

Therapeutic Agent-Lipid Particle Compositions and Formulations

In further embodiments, the present invention relates to compositions that include a lipid particle as described herein and an active agent, where the active agent is associated with the lipid particle. In certain embodiments, the active agent is a therapeutic agent. In some embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

"Fully encapsulated" as used herein indicates that the nucleic acid in the particles is not significantly degraded after exposure to serum or a nuclease assay that would significantly degrade free nucleic acids. In a fully encapsulated system, for example, less than about 25% of particle nucleic acid is degraded in a treatment that would normally degrade 100% of free nucleic acid, for example less than about 10% or less than about 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, Calif.). Fully encapsulated also suggests that the particles are serum stable, that is, that they do not rapidly decompose into their component parts upon in vivo administration.

Active agents, as used herein, include any molecule or compound capable of exerting a desired effect on a cell, tissue, organ, or subject. Such effects may be biological, physiological, or cosmetic, for example. Active agents may be any type of molecule or compound, including, but not limited to, nucleic acids, peptides and polypeptides, including, e.g., antibodies, such as, e.g., polyclonal antibodies, monoclonal antibodies, antibody fragments; humanized antibodies, recombinant antibodies, recombinant human antibodies, and Primatized™ antibodies, cytokines, growth factors, apoptotic factors, differentiation-inducing factors, cell surface receptors and their ligands; hormones; and small molecules, including small organic molecules or compounds.

In one embodiment, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative lacks therapeutic activity.

In various embodiments, therapeutic agents include any therapeutically effective agent or drug, such as, for example, anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs, e.g., anti-arrhythmic agents, vasoconstrictors, hormones, and steroids.

In certain embodiments, the therapeutic agent is an oncology drug, which may also be referred to as an anti-tumor drug, an anti-cancer drug, a tumor drug, an antineoplastic agent, or the like. Examples of oncology drugs that may be used include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used are ellipticin and ellipticin analogs or derivatives, epothilones, intracellular kinase inhibitors and camptothecins.

Nucleic Acid-Lipid Particles

In further embodiments, the lipid particles described herein are associated with a nucleic acid, resulting in a nucleic acid-lipid particle. In some embodiments, the nucleic acid is fully encapsulated in the lipid particle. As used herein, the term "nucleic acid" is meant to include any oligonucleotide or polynucleotide. Fragments containing up to 50 nucleotides are generally termed oligonucleotides, and longer fragments are called polynucleotides. In some embodiments, oligonucletoides are 15-50 nucleotides in length.

The terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The nucleic acid present in a lipid-nucleic acid particle may include any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNA, and triplex-forming oligonucleotides. The nucleic acid that is present in a lipid-nucleic acid particle may include one or more of the oligonucleotide modifications described below.

Nucleic acids may be of various lengths, generally dependent upon the particular form of nucleic acid. For example, in some embodiments, plasmids or genes may be from about 1,000 to about 100,000 nucleotide residues in length. In some embodiments, oligonucleotides may range from about 10 to about 100 nucleotides in length. In various embodiments, oligonucleotides, single-stranded, double-stranded, and triple-stranded, may range in length from about 10 to about 50 nucleotides, from about 20 to about 50 nucleotides, from about 15 to about 30 nucleotides or from about 20 to about 30 nucleotides in length.

In certain embodiments, the oligonucleotide (or a strand thereof) specifically hybridizes to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions, e.g. mismatches, as compared to the region of a gene or mRNA sequence that it is targeting or to which it specifically hybridizes.

RNA Interference Nucleic Acids

In certain embodiments, nucleic acid-lipid particles are associated with RNA interference (RNAi) molecules. RNA interference methods using RNAi molecules may be used to disrupt the expression of a gene or polynucleotide of interest. Small interfering RNA (siRNA) has essentially replaced antisense ODN and ribozymes as the next generation of targeted oligonucleotide drugs under development.

SiRNAs are RNA duplexes normally 16-30 nucleotides long that can associate with a cytoplasmic multi-protein complex known as RNAi-induced silencing complex (RISC). RISC loaded with siRNA mediates the degradation of homologous mRNA transcripts, therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense ODN or ribozymes. A variety of RNAi reagents, including siRNAs targeting clinically relevant targets, are currently under pharmaceutical development, as described, e.g., in de Fougerolles, A. et al., Nature Reviews 6:443-453 (2007).

While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S. and Christian, A. T., (2003) *Molecular Biotechnology* 24:111-119). Thus, the use of RNAi molecules comprising any of these different types of double-stranded molecules is contemplated. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded oligonucleotides comprising two separate strands, i.e. a sense strand and an antisense strand, e.g., small interfering RNA (siRNA); double-stranded oligonucleotide comprising two separate strands that are linked together by non-nucleotidyl linker; oligonucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

A "single strand siRNA compound" as used herein, is an siRNA compound which is made up of a single molecule. It may include a duplexed region, formed by intra-strand pairing, e.g., it may be, or include, a hairpin or pan-handle structure. Single strand siRNA compounds may be antisense with regard to the target molecule A single strand siRNA compound may be sufficiently long that it can enter the RISC and participate in RISC mediated cleavage of a target mRNA. A single strand siRNA compound is at least 14, and in other embodiments at least 15, 20, 25, 29, 35, 40, or 50 nucleotides in length. In certain embodiments, it is less than 200, 100, or 60 nucleotides in length.

Hairpin siRNA compounds will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region. In certain embodiments, the overhangs are 2-3 nucleotides in length. In some embodiments, the overhang is at the sense side of the hairpin and in some embodiments on the antisense side of the hairpin.

A "double stranded siRNA compound" as used herein, is an siRNA compound which includes more than one, and in some cases two, strands in which interchain hybridization can form a region of duplex structure.

The antisense strand of a double stranded siRNA compound may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length. As used herein, term "antisense strand" means the strand of an siRNA compound that is sufficiently complementary to a target molecule, e.g. a target RNA.

The sense strand of a double stranded siRNA compound may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded siRNA compound may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In many embodiments, the siRNA compound is sufficiently large that it can be cleaved by an endogenous molecule, e.g., by Dicer, to produce smaller siRNA compounds, e.g., siRNAs agents The sense and antisense strands may be chosen such that the double-stranded siRNA compound includes a single strand or unpaired region at one or both ends of the molecule. Thus, a double-stranded siRNA compound may contain sense and antisense strands, paired to contain an overhang, e.g., one or two 5' or 3' overhangs, or a 3' overhang of 1-3 nucleotides. The overhangs can be the result of one strand being longer than the other, or the result of two strands of the same length being staggered. Some embodiments will have at least one 3' overhang. In one embodiment, both ends of an siRNA molecule will have a 3' overhang. In some embodiments, the overhang is 2 nucleotides.

In certain embodiments, the length for the duplexed region is between 15 and 30, or 18, 19, 20, 21, 22, and 23 nucleotides in length, e.g., in the ssiRNA compound range discussed above. ssiRNA compounds can resemble in length and structure the natural Dicer processed products from long dsiRNAs. Embodiments in which the two strands of the ssiRNA compound are linked, e.g., covalently linked are also included. Hairpin, or other single strand structures which provide the required double stranded region, and a 3' overhang are also contemplated.

The siRNA compounds described herein, including double-stranded siRNA compounds and single-stranded siRNA compounds can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an ssiRNA compound of 21 to 23 nucleotides.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in certain embodiments, the siRNA compound specifically discriminates a single-nucleotide difference. In this case, the siRNA compound only mediates RNAi if exact complementary is found in the region (e.g., within 7 nucleotides of) the single-nucleotide difference.

MicroRNAs

Micro RNAs (miRNAs) are a highly conserved class of small RNA molecules that are transcribed from DNA in the genomes of plants and animals, but are not translated into protein. Processed miRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111; and also at http://microrna.sanger.ac.uk/sequences/.

Antisense Oligonucleotides

In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence, e.g. a target gene mRNA.

Antisense oligonucleotides are thought to inhibit gene expression by binding to a complementary mRNA. Binding to the target mRNA can lead to inhibition of gene expression either by preventing translation of complementary mRNA strands by binding to it, or by leading to degradation of the target mRNA. Antisense DNA can be used to target a specific, complementary (coding or non-coding) RNA. If binding takes places this DNA/RNA hybrid can be degraded by the enzyme RNase H. In certain embodiments, antisense oligonucleotides contain from about 10 to about 50 nucleotides, such as from about 15 to about 30 nucleotides. The term also encompasses antisense oligonucleotides that may not be exactly complementary to the desired target gene. Thus, instances where non-target specific-activities are found with antisense, or where an antisense sequence containing one or more mismatches with the target sequence is the most preferred for a particular use, are contemplated.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1(4):225-32; Peris et al., Brain Res Mol Brain Res. 1998 Jun. 15; 57(2):310-20; U.S. Pat. Nos. 5,801,154; 5,789,573; 5,718,709 and 5,610,288). Furthermore, antisense constructs have also been described that inhibit and can be used to treat a variety of abnormal cellular proliferations, e.g. cancer (U.S. Pat. Nos. 5,747,470; 5,591,317 and 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689. Antagomir RNAs may be synthesized using standard solid phase oligonucleotide synthesis protocols. See U.S. Patent Publication Nos. 2007/0123482 and 2007/0213292.

An antagomir can include ligand-conjugated monomer subunits and monomers for oligonucleotide synthesis. Exemplary monomers are described in U.S. Publication No. 2005/0107325. An antagomir can have a ZXY structure, such as is described in International Publication No. WO 2004/080406. An antagomir can be complexed with an amphipathic moiety. Exemplary amphipathic moieties for use with oligonucleotide agents are described in International Publication No. WO 2004/080406.

Aptamers

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9(1999), and Hermann and Patel, Science 287:820-5 (2000). Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Ribozymes

According to another embodiment, nucleic acid-lipid particles are associated with ribozymes. Ribozymes are RNA molecules complexes having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or *Neurospora* VS RNA motif, for example. Examples of hammerhead motifs are described by Rossi et al. Nucleic Acids Res. 1992 Sep. 11; 20(17):4559-65. Examples of hairpin motifs are described by Hampel et al. (European Publication No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; *Neurospora* VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Important characteristics of enzymatic nucleic acid molecules used are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in International Publication Nos. WO 93/23569 and WO 94/02595, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., International Publication Nos. WO 92/07065, WO 93/15187, WO 94/13688 and WO 91/03162; European Application No. 92110298.4; and U.S. Pat. No. 5,334,711; which describe various chemical modifications that can be made to the sugar moieties of enzymatic RNA molecules), modifications which enhance their efficacy in cells, and removal of stem II bases to shorten RNA synthesis times and reduce chemical requirements.

Immunostimulatory Oligonucleotides

Nucleic acids associated with lipid particles may be immunostimulatory, including immunostimulatory oligonucleotides (ISS; single- or double-stranded) capable of inducing an immune response when administered to a subject, which may be a mammal or other patient. ISS include, e.g., certain palindromes leading to hairpin secondary structures (see Yamamoto S., et al. (1992) *J. Immunol.* 148: 4072-4076), or CpG motifs, as well as other known ISS features (such as multi-G domains, see, e.g., international Publication No. WO 96/11266).

The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

In certain embodiments, an immunostimulatory nucleic acid is only immunostimulatory when administered in combination with a lipid particle, and is not immunostimulatory when administered in its "free form." Such an oligonucleotide is considered to be immunostimulatory.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. In another embodiment, the nucleic acid comprises the sequence 5' TAACGTTGAGGGGCAT 3'. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of said CpG dinucleotides comprises a methylated cytosine.

In one embodiment, the nucleic acid comprises the sequence 5' TTCCATGACGTTCCTGACGT 3'. In another embodiment, the nucleic acid sequence comprises the sequence 5' TCCATGACGTTCCTGACGT 3', wherein the two cytosines indicated in bold are methylated. In further embodiments, the ODN is selected from a group of ODNs consisting of ODN #1, ODN #2, ODN #3, ODN #4, ODN #5, ODN #6, ODN #7, ODN #8, and ODN #9, as shown below.

TABLE 2

Exemplary Immunostimulatory Oligonucleotides (ODNs)

| ODN NAME | SEQ ID | ODN SEQUENCE (5'-3') |
|---|---|---|
| ODN 1 human c-myc | | 5'-TAACGTTGAGGGGCAT-3 |
| * ODN 1 m | | 5'-TAAZGTTGAGGGGCAT-3 |

TABLE 2-continued

Exemplary Immunostimulatory Oligonucleotides (ODNs)

| ODN NAME | SEQ ID | ODN SEQUENCE (5'-3') |
|---|---|---|
| ODN 2 | | 5'-TCCATGACGTTCCTGACGTT-3' |
| * ODN 2 m | | 5'-TCCATGAZGTTCCTGAZGTT-3' |
| ODN 3 | | 5'-TAAGCATACGGGGTGT-3' |
| ODN 5 | | 5'-AACGTT-3' |
| ODN 6 | | 5'-GATGCTGTGTCGGGGTCTCCGGGC-3' |
| ODN 7 | | 5'-TCGTCGTTTTGTCGTTTTGTCGTT-3' |
| ODN 7 m | | 5'-TZGTZGTTTTGTZGTTTTGTZGTT-3' |
| ODN 8 | | 5'-TCCAGGACTTCTCTCAGGTT-3' |
| ODN 9 | | 5'-TCTCCCAGCGTGCGCCAT-3' |
| ODN 10 murine Intracellular Adhesion Molecule-1 | | 5'-TGCATCCCCCAGGCCACCAT-3 |
| ODN 11 human Intracellular Adhesion Molecule-1 | | 5'-GCCCAAGCTGGCATCCGTCA-3' |
| ODN 12 human Intracellular Adhesion Molecule-1 | | 5'-GCCCAAGCTGGCATCCGTCA-3' |
| ODN 13 human erb-B-2 | | 5'-GGT GCTCACTGC GGC-3' |
| ODN 14 human c-myc | | 5'-AACC GTT GAG GGG CAT-3' |
| ODN 15 human c-myc | | 5'-TAT GCT GTG CCG GGG TCT TCG GGC-3' |
| ODN 16 | | 5'-GTGCCG GGGTCTTCGGGC-3' |
| ODN 17 human Insulin Growth Factor 1-Receptor | | 5'-GGACCCTCCTCCGGAGCC-3' |
| ODN 18 human Insulin Growth Factor 1-Receptor | | 5'-TCC TCC GGA GCC AGA CTT-3' |
| ODN 19 human Epidermal Growth Factor-Receptor | | 5'-AAC GTT GAG GGG CAT-3' |
| ODN 20 Epidermal Growth Factor-Receptor | | 5'-CCGTGGTCA TGCTCC-3' |
| ODN 21 human Vascular Endothelial Growth Factor | | 5'-CAG CCTGGCTCACCG CCTTGG-3' |
| ODN 22 murine Phosphokinase C-alpha | | 5'-CAG CCA TGG TTC CCC CCA AC-3' |
| ODN 23 | | 5'-GTT CTC GCT GGT GAG TTT CA-3' |
| ODN 24 human Bcl-2 | | 5'-TCT CCCAGCGTGCGCCAT-3' |
| ODN 25 human C-Raf-s | | 5'-GTG CTC CAT TGA TGC-3' |
| ODN #26 human Vascular Endothelial Growth Factor Receptor-1 | | 5'-GAGUUCUGAUGAGGCCGAAAGG-CCGAAAGUCUG-3' |
| ODN #27 | | 5'-RRCGYY-3' |
| ODN #28 | | 5'-AACGTTGAGGGGCAT-3' |

TABLE 2-continued

Exemplary Immunostimulatory Oligonucleotides (ODNs)

| ODN NAME | SEQ ID | ODN SEQUENCE (5'-3') |
|---|---|---|
| ODN #29 | | 5'-CAACGTTATGGGGAGA-3' |
| ODN #30 human c-myc | | 5'-TAACGTTGAGGGGCAT-3' |

"Z" represents a methylated cytosine residue. ODN 14 is a 15-mer oligonucleotide and ODN 1 is the same oligonucleotide having a thymidine added onto the 5' end making ODN 1 into a 16-mer. No difference in biological activity between ODN 14 and ODN 1 has been detected and both exhibit similar immunostimulatory activity
(Mui et al., 2001)

Additional nucleic acid sequences of suitable oligonucleotides (ODNs) are described in, for example, Raney et al., *Journal of Pharmacology and Experimental Therapeutics*, 298:1185-1192 (2001). In certain embodiments, ODNs used in the compositions and methods of the present invention have a phosphodiester ("PO") backbone or a phosphorothioate ("PS") backbone, and/or at least one methylated cytosine residue in a CpG motif.

Decoy Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in, for example, Mann et al., *J. Clin. Invest.*, 2000, 106: 1071-1075.

Supermir

A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. This term includes oligonucleotides composed of naturally-occurring nucleobases, sugars and covalent internucleoside (backbone) linkages and which contain at least one non-naturally-occurring portion which functions similarly. Such modified or substituted oligonucleotides are preferred over native forms because of desirable properties such as, for example, enhanced cellular uptake, enhanced affinity for nucleic acid target and increased stability in the presence of nucleases. In one embodiment, the supermir does not include a sense strand, and in another embodiment, the supermir does not self-hybridize to a significant extent. A supermir can have secondary structure, but it is substantially single-stranded under physiological conditions. A supermir that is substantially single-stranded is single-stranded to the extent that less than about 50% (e.g., less than about 40%, less than about 30%, less than about 20%, less than about 10%, or less than about 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or n nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

miRNA Mimics miRNA mimics represent a class of molecules that can be used to imitate the gene silencing ability of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs). miRNA mimics can be comprised of nucleic acid (modified or modified nucleic acids) including oligonucleotides comprising, without limitation, RNA, modified RNA, DNA, modified DNA, locked nucleic acids, or 2'-O,4'-C-ethylene-bridged nucleic acids (ENA), or any combination of the above (including DNA-RNA hybrids). In addition, miRNA mimics can comprise conjugates that can affect delivery, intracellular compartmentalization, stability, specificity, functionality, strand usage, and/or potency. In one design, miRNA mimics are double stranded molecules (e.g., with a duplex region of between about 16 and about 31 nucleotides in length) and contain one or more sequences that have identity with the mature strand of a given miRNA. Modifications can comprise 2' modifications (including 2'-O methyl modifications and 2' F modifications) on one or both strands of the molecule and internucleotide modifications (e.g. phosphorothioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality. In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Antimir or miRNA Inhibitor

The terms "antimir," "microRNA inhibitor," "miR inhibitor," or "inhibitor," are synonymous and refer to oligonucleotides or modified oligonucleotides that interfere with the ability of specific miRNAs. In general, the inhibitors are nucleic acid or modified nucleic acids in nature including oligonucleotides comprising RNA, modified RNA, DNA, modified DNA, locked nucleic acids (LNAs), or any combination of the above. Modifications include 2' modifications (including 2'-0 alkyl modifications and 2' F modifications) and internucleotide modifications (e.g. phosphorothioate modifications) that can affect delivery, stability, specificity, intracellular compartmentalization, or potency. In addition, miRNA inhibitors can comprise conjugates that can affect delivery, intracellular compartmentalization, stability, and/or potency. Inhibitors can adopt a variety of configurations including single stranded, double stranded (RNA/RNA or RNA/DNA duplexes), and hairpin designs, in general, microRNA inhibitors comprise contain one or more sequences or portions of sequences that are complementary or partially complementary with the mature strand (or strands) of the miRNA to be targeted, in addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, or U). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. Micro-RNA inhibitors, when double stranded, may include mismatches between nucleotides on opposite strands. Furthermore, micro-RNA inhibitors may be linked to conjugate moieties in order to facilitate uptake of the inhibitor into a cell. For example, a micro-RNA inhibitor may be linked to cholesteryl 5-(bis(4-methoxyphenyl)(phenyl)methoxy)-3 hydroxypentylcarbamate) which allows passive uptake of a micro-RNA inhibitor into a cell. Micro-RNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in International Publication Nos. WO2007/095387 and WO 2008/036825. A person of ordinary skill in the art can select a sequence from the database for a desired miRNA and design an inhibitor useful for the methods disclosed herein.

U1 Adaptor

U1 adaptor inhibit polyA sites and are bifunctional oligonucleotides with a target domain complementary to a site in the target gene's terminal exon and a 'U1 domain' that binds to the U1 smaller nuclear RNA component of the U1 snRNP (Goraczniak, et al., 2008, Nature Biotechnology, 27(3), 257-263). U1 snRNP is a ribonucleoprotein complex that functions primarily to direct early steps in spliceosome formation by binding to the pre-mRNA exon-intron boundary (Brown and Simpson, 1998, *Annu. Rev. Plant Physiol. Plant Mol. Biol.*, 49:77-95). Nucleotides 2-11 of the 5' end of U1 snRNA base pair bind with the 5'ss of the pre mRNA. In one embodiment, oligonucleotides are U1 adaptors. In one embodiment, the U1 adaptor can be administered in combination with at least one other iRNA agent.

Oligonucleotide Modifications

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications of oligonucleotides can confer improved properties, and, e.g., can render oligonucleotides more stable to nucleases.

As oligonucleotides are polymers of subunits or monomers, many of the modifications described below occur at a position which is repeated within an oligonucleotide, e.g., a modification of a base, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal regions, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of a double-stranded oligonucleotide or may only occur in a single strand region of a double-stranded oligonucleotide. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is desirable, e.g., to enhance stability, to include particular nucleobases in overhangs, or to include modified nucleotides or nucleotide surrogates, in single strand overhangs, e.g., in a 5' or 3' overhang, or in both. For example, it can be desirable to include purine nucleotides in overhangs. In some embodiments, all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Additional exemplary modifications are discussed in more detail below.

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus, while not wishing to be bound by theory, it can be desirable, in some embodiments, to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following: S, Se, $BR_3$ (R is hydrogen, alkyl, aryl), C (e.g., an alkyl group or an aryl group), H, $NR_2$ (R is hydrogen, alkyl, aryl), or OR (R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is one embodiment. When the bridging oxygen is the 5'-oxygen of a nucleoside, replacement with nitrogen is one embodiment.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiments, to introduce alterations in which the charged phosphate group is replaced by a neutral moiety.

Examples of moieties which can replace the phosphate group include, for example, methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Examplary replacements include methylenecarbonylamino and methylenemethylimino groups.

Modified phosphate linkages where at least one of the oxygens linked to the phosphate has been replaced or the phosphate group has been replaced by a non-phosphorous group, are also referred to as "non phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiments, to introduce alterations in which the bases are tethered by a neutral surrogate backbone. Examples include the morpholino, cyclobutyl, pyrrolidine and peptide nucleic acid (PNA) nucleoside surrogates. A preferred surrogate is a PNA surrogate.

Sugar Modifications

A modified RNA can include modification of all or some of the sugar groups of the ribonucleic acid. For example, the 2' hydroxyl group (OH) can be modified or replaced with a number of different "oxy" or "deoxy" substituents. While not being bound by theory, enhanced stability may be observed, since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable, in some embodiments, to introduce alterations in which alkoxide formation at the 2' position is not possible.

Examples of "oxy"-2' hydroxyl group modifications include —OR, where R is H, alkyl, cycloalkyl, aryl, aralkyl, heteroaryl or sugar (e.g., —OR can be alkoxy or aryloxy); polyethyleneglycols (PEG), $O(CH_2CH_2O)_nCH_2CH_2OR$ (where R is as defined above and n is 1-20); "locked" nucleic acids (LNA) in which the 2' hydroxyl is connected, e.g., by a methylene bridge, to the 4' carbon of the same ribose sugar; —O-AMINE (where AMINE is $NH_2$, alkylamino, dialkylamino, heterocyclyl, arylamino, diaryl amino, heteroaryl amino, diheteroaryl amino, ethylene diamine, or polyamino); aminoalkoxy; —$O(CH_2)_n$AMINE, (where n is 1 to 20 and AMINE is $NH_2$, alkylamino, dialkylamino, heterocyclyl, arylamino, diaryl amino, heteroaryl amino, diheteroaryl amino, ethylene diamine, or polyamino). In one embodiment, the group is a methoxyethyl group (MOE), ($OCH_2CH_2OCH_3$, a PEG derivative).

"Deoxy" modifications include hydrogen (i.e., deoxyribose sugars, which are of particular relevance to the overhang portions of partially ds RNA); halo (e.g., fluoro); amino (e.g., $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (where AMINE is $NH_2$, alkylamino, dialkylamino, heterocyclyl, arylamino, diaryl amino, heteroaryl amino, or diheteroaryl amino and n is 1 to 20), —NHC(O)R (where R is alkyl, cycloalkyl, aryl, aralkyl, heteroaryl or sugar), cyano; mercapto; alkyl-thio-alkyl; thioalkoxy; alkyl, cycloalkyl, aryl, alkenyl and alkynyl, which may be optionally substituted with e.g., an amino functionality. Other substitutents of certain embodiments include 2'-methoxyethyl, 2'-$OCH_3$, 2'-O-allyl, 2'-C-allyl, and 2'-fluoro.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Terminal Modifications

The 3' and 5' ends of an oligonucleotide can be modified. Such modifications can be at the 3' end, the 5' end or at both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications can be added for a number of reasons, including as discussed elsewhere herein to modulate activity or to modulate resistance to degradation. Terminal modifications useful for modulating activity include modification of the 5' end with phosphate or phosphate analogs, e.g., in certain embodiments, iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate and 5'-gamma-thiotriphosphate), 5'-phosphoramidates ((HO)$_2$(O)P—NH-5', (HO)(NH$_2$)(O)P—O-5'), 5'-alkylphosphonates (e.g., R—P(OH)(O)—O-5'- where R is alkyl, such as methyl, ethyl, isopropyl, or propyl) or (OH)$_2$(O)P-5'-CH$_2$—); and 5'-alkyletherphosphonates (e.g., RP(OH)(O)—O-5'- where R is an alkylether, such as methoxymethyl (MeOCH$_2$—) or ethoxymethyl). In one embodiment, the 5' terminus of a single stranded iRNA agent, or of the antisense strand of a double stranded iRNA agent can be phosphorylated or include a phosphoryl analog, such as those described above.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases", "modified bases", "non-natural bases" and "universal bases" described herein, can be employed. Examples include, without limitation, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., *Angewandte Chemie*, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A suitable position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE is, e.g., NH$_2$, alkylamino, dialkylamino, heterocyclyl, arylamino, diaryl amino, heteroaryl amino, diheteroaryl amino, ethylene diamine, or polyamino); aminoalkoxy, e.g., O(CH$_2$)$_n$AMINE, (e.g., n is 1 to 20 and AMINE is e.g., NH$_2$, alkylamino, dialkylamino, heterocyclyl, arylamino, diaryl amino, heteroaryl amino, or diheteroaryl amino, ethylene diamine, polyamino); amino (e.g. NH$_2$, alkylamino, dialkylamino, heterocyclyl, arylamino, diaryl amino, heteroaryl amino, diheteroaryl amino, or amino acid); or NH(CH$_2$CH$_2$NH)$_n$CH$_2$CH$_2$-AMINE (where AMINE is e.g., NH$_2$, alkylamino, dialkylamino, heterocyclyl, arylamino, diarylamino, heteroarylamino, or diheteroaryl amino).

Placement within an Oligonucleotide

In further embodiments, modifications may be included on an oligonucleotide at a particular location, e.g., at an internal position of a strand, or on the 5' or 3' end of an oligonucleotide. For example, one particular location of a modification on an oligonucleotide, may confer preferred properties on the agent. For example, locations of particular modifications may confer optimum gene silencing properties, or increased resistance to endonuclease or exonuclease activity.

One or more nucleotides of an oligonucleotide may have a 2'-5' linkage. One or more nucleotides of an oligonucleotide may have inverted linkages, e.g. 3'-3', 5'-5', 2'-2' or 2'-3' linkages.

A double-stranded oligonucleotide may include at least one 5'-uridine-adenine-3' (5'-UA-3') dinucleotide wherein the uridine is a 2'-modified nucleotide, or a terminal 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

Ligands

A wide variety of entities can be coupled to the oligonucleotides and lipids. Suitable moieties are ligands, which are coupled, for example, covalently, either directly or indirectly via an intervening tether.

In certain embodiments, a ligand alters the distribution, targeting or lifetime of the molecule into which it is incorporated. In some embodiments, a ligand provides an enhanced affinity for a selected target, e.g., molecule, cell or cell type, compartment, e.g., a cellular or organ compartment, tissue, organ or region of the body, as, e.g., compared to a species absent such a ligand. Ligands providing enhanced affinity for a selected target are also termed targeting ligands. Examplary ligands for conjugation to the lipids are targeting ligands.

Some ligands can have endosomolytic properties. The endosomolytic ligands promote the lysis of the endosome and/or transport of the composition, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/ or transport of the composition, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., *J. Am. Chem. Soc.,* 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in Table 3.

TABLE 3

List of Peptides with Endosomolytic Activity.

| Name | Sequence (N to C) | Ref. |
| --- | --- | --- |
| GALA | AALEALAEALEALAEALEALAEAAAAGGC | 1 |
| EALA | AALAEALAEALAEALAEALAEALAAAAGGC<br>ALEALAEALEALAEA | 2<br>3 |
| INF-7 | GLFEAIEGFIENGWEGMIVVDYG | 4 |
| Inf HA-2 | GLFGAIAGFIENGWEGMIDGWYG | 5 |
| diINF-7 | GLF EAI EGFI ENGW EGMI DGWYGC<br>GLF EAI EGFI ENGW EGMI DGWYGC | 5 |
| diINF3 | GLF EAI EGFI ENGW EGMI DGGC<br>GLF EAI EGFI ENGW EGMI DGGC | 6 |
| GLF | GLFGALAEALAEALAEHLAEALAEALEALA<br>AGGSC | 6 |
| GALA-INF3 | GLFEAIEGFIENGWEGLAEALAEALEALAAG<br>GSC | 6 |
| INF-5 | GLF EAI EGFI ENGW EGnI DG K<br>GLF EAI EGFI ENGW EGnI DG | 4 | n, norleucine
1. Subbarao et al., Biochemistry, 1987, 26: 2964-2972.
2. Vogel et al., J. Am. Chem. Soc., 1996, 118: 1581-1586
3. Turk, M. J., Reddy, J. A. et al. (2002). Characterization of a novel pH-sensitive peptide that enhances drug release from folate-targeted liposomes at endosomal pHs. *Biochim. Biophys. Acta* 1559, 56-68.
4. Plank, C. Oberhauser, B. Mechtler, K. Koch, C. Wagner, E. (1994). The influence of endosome-disruptive peptides on gene transfer using synthetic virus-like gene transfer systems, J. Biol. Chem. 269 12918-12924.
5. Mastrobattista, E., Koning, G. A. et al. (2002). Functional characterization of an endosome-disruptive peptide and its application in cytosolic delivery of immunoliposome-entrapped proteins. *J. Biol. Chem.* 277, 27135-43.
6. Oberhauser, B., Plank, C. et al. (1995). Enhancing endosomal exit of nucleic acids using pH-sensitive viral fusion peptides. Deliv. Strategies Antisense Oligonucleotide Ther. 247-66.

Examplary ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include, for example, lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 4 shows some examples of targeting ligands and their associated receptors.

TABLE 4

Targeting Ligands and their Associated Receptors

| Liver cells | Ligand | Receptor |
|---|---|---|
| Parenchymal Cell (PC) hepatocytes | Galactose | ASGP-R (Asiologlycoprotein receptor) |
| | Gal NAc (N-acetyl galactosamine) | ASPG-R Gal NAc Receptor |
| | Lactose | |
| | Asialofetuin | ASPG-r |
| Sinusoidal Endothelial Cell (SEC) | Hyaluronan | Hyaluronan receptor |
| | Procollagen | Procollagen receptor |
| | Negatively charged molecules | Scavenger receptors |
| | Mannose | Mannose receptors |
| | N-acetyl Glucosamine | Scavenger receptors |
| | Immunoglobulins | Fc Receptor |
| | LPS | CD14 Receptor |
| | Insulin | Receptor mediated transcytosis |
| | Transferrin | Receptor mediated transcytosis |
| | Albumins | Non-specific |
| | Mannose-6-phosphate | Mannose-6-phosphate receptor |
| Kupffer Cell (KC) | Mannose | Mannose receptors |
| | Fucose | Fucose receptors |
| | Albumins | Non-specific |
| | Mannose-albumin conjugates | |

Other examples of ligands include, but are not limited to, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one embodiment, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In one embodiment, the lipid based ligand binds HSA. For example, it binds HSA with a sufficient affinity such that the conjugate will be preferably distributed to a non-kidney tissue. However, it is desirable that the affinity not be so strong that the HSA-ligand binding cannot be reversed.

In another embodiment, the lipid based ligand binds HSA weakly or not at all, such that the conjugate will be distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are useful for treating disorders characterized by unwanted cell proliferation, e.g., of the malignant or non-malignant type, e.g., cancer cells. Exemplary vitamins include vitamin A, E, and K. Other exemplary vitamins include B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, about 10, about 15, about 20, about 25, about 30, about 35, about 40, about 45, or about 50 amino acids long (see, e.g., Table 5).

peptide moiety can be a "delivery" peptide, which can carry large polar molecules including peptides, oligonucleotides, and protein across cell membranes. For example, sequences from the HIV Tat protein (GRKKRRQRRRPPQ) and the Drosophila Antennapedia protein (RQIKIWFQNRRMK-WKK) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). For example, the peptide or peptidomimetic tethered to an iRNA agent via an incorporated monomer unit is a cell targeting peptide such as an

TABLE 5

Exemplary Cell Permeation Peptides.

| Cell Permeation Peptide | Amino acid Sequence | Reference |
|---|---|---|
| Penetratin | RQIKIWFQNRRMKWKK | Derossi et al., J. Biol. Chem. 269: 10444, 1994 |
| Tat fragment (48-60) | GRKKRRQRRRPPQ | Vives et al., J. Biol. Chem., 272: 16010, 1997 |
| Signal Sequence-based peptide | GALFLGWLGAAGSTMGAWSQPKKKRKV | Chaloin et al., Biochem. Biophys. Res. Commun., 243: 601, 1998 |
| PVEC | LLIILRRRIRKQAHAHSK | Elmquist et al., Exp. Cell Res., 269: 237, 2001 |
| Transportan | GWTLNSAGYLLKINLKALAALAKKIL | Pooga et al., FASEB J., 12: 67, 1998 |
| Amphiphilic model peptide | KLALKLALKALKAALKLA | Oehlke et al., Mol. Ther., 2: 339, 2000 |
| Arg$_9$ | RRRRRRRRR | Mitchell et al., J. Pept. Res., 56: 318, 2000 |
| Bacterial cell wall permeating | KFFKFFKFFK | |
| LL-37 | LLGDFFRKSKEKIGKEFKRIVQRIKDFLRNLVPRTES | |
| Cecropin P1 | SWLSKTAKKLENSAKKRISEGIAIAIQGGPR | |
| α-defensin | ACYCRIPACIAGERRYGTCIYQGRLWAFCC | |
| b-defensin | DHYNCVSSGGQCLYSACPIFTKIQGTCYRGKAKCCK | |
| Bactenecin | RKCRIVVIRVCR | |
| PR-39 | RRRPRPPYLPRPRPPPFFPPRLPPRIPPGFPPRFPPRFPGKR-NH2 | |
| Indolicidin | ILPWKWPWWPWRR-NH2 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP. An RFGF analogue (e.g., amino acid sequence AALLPVLLAAP) containing a hydrophobic MTS can also be a targeting moiety. The arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., *Cancer Gene Therapy*, 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_V\beta_3$ (Haubner et al., *J. Nucl. Med.*, 42:326-336, 2001).

Peptides that target markers enriched in proliferating cells can be used. E.g., RGD containing peptides and peptidomimetics can target cancer cells, in particular cells that exhibit an $\alpha v\beta 3$ integrin. Thus, one could use RGD peptides, cyclic peptides containing RGD, RGD peptides that include D-amino acids, as well as synthetic RGD mimics. In addition to RGD, one can use other moieties that target the $\alpha v\beta 3$ integrin ligand. Generally, such ligands can be used to control proliferating cells and angiogeneis. Examplary conjugates of this type are ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide tethered to an iRNA agent and/or the carrier oligomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, H₂A peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include, for example, imidazoles, poly or oligoimidazoles, PEIs, peptides, fusogenic peptides, polycaboxylates, polycations, masked oligo- or poly-cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulators include, for example, lipophiles, bile acids, steroids, phospholipid analogues, peptides, protein binding agents, PEG, and vitamins. Examplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, and biotin. Oligonucleotides that comprise a number of phosphorothioate linkages are also known to bind to serum protein, thus short oligonucleotides, e.g. oligonucleotides of about 5 bases, about 10 bases, about 15 bases or about 20 bases, comprising multiple of phosphorothioate linkages in the backbone are also amenable as ligands (e.g. as PK modulating ligands).

In addition, aptamers that bind serum components (e.g. serum proteins) are also amenable as PK modulating ligands.

Other amenable ligands are described in U.S. Patent Application Nos. 2005/0107325, 2005/0164235, and 2008-0255345, and in U.S. Pat. Nos. 7,021,394, and 7,626,014.

When two or more ligands are present, the ligands can all have same properties, all have different properties or some ligands have the same properties while others have different properties. For example, a ligand can have targeting properties, have endosomolytic activity or have PK modulating properties. In one embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-(CH₂)ₙNH₂ may be incorporated into a growing sense or antisense strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. In general, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17.

Characteristics of Nucleic Acid-Lipid Particles

Methods and compositions for producing lipid-encapsulated nucleic acid particles in which nucleic acids are encapsulated within a lipid layer are provided. Such nucleic acid-lipid particles, incorporating siRNA oligonucleotides, are characterized using a variety of biophysical parameters including: (1) drug to lipid ratio; (2) encapsulation efficiency; and (3) particle size. High drug to lipid rations, high encapsulation efficiency, good nuclease resistance and serum stability and controllable particle size, generally less than about 200 nm in diameter are desirable. In addition, the nature of the nucleic acid polymer is of significance, since the modification of nucleic acids in an effort to impart nuclease resistance adds to the cost of therapeutics while in many cases providing only limited resistance. Unless stated otherwise, these criteria are calculated in this specification as follows:

Nucleic acid to lipid ratio is the amount of nucleic acid in a defined volume of preparation divided by the amount of lipid in the same volume. This may be on a mole per mole basis or on a weight per weight basis, or on a weight per mole basis. For final, administration-ready formulations, the nucleic acid:lipid ratio is calculated after dialysis, chromatography and/or enzyme (e.g., nuclease) digestion has been employed to remove as much of the external nucleic acid as possible.

Encapsulation efficiency refers to the drug to lipid ratio of the starting mixture divided by the drug to lipid ratio of the final, administration competent formulation. This is a measure of relative efficiency. For a measure of absolute efficiency, the total amount of nucleic acid added to the starting mixture that ends up in the administration competent formulation, can also be calculated. The amount of lipid lost during the formulation process may also be calculated. Efficiency is a measure of the wastage and expense of the formulation; and Size indicates the size (diameter) of the particles formed. Size distribution may be determined using quasi-elastic light scattering (QELS) on a Nicomp Model 370 sub-micron particle sizer. Particles under 200 nm are preferred for distribution to neo-vascularized (leaky) tissues, such as neoplasms and sites of inflammation.

Pharmaceutical Compositions

The lipid particles, particularly, when associated with a therapeutic agent, may be formulated as a pharmaceutical composition, which further comprises a pharmaceutically acceptable diluent, excipient, or carrier, such as physiological saline or phosphate buffer, selected in accordance with the route of administration and standard pharmaceutical practice.

In certain embodiments, pharmaceutical compositions comprising the lipid-nucleic acid particles are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, and the like, including glycoproteins for enhanced stability, such as albumin, lipoprotein, and globulin. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical formulations can vary widely, for example, from less than about 0.01%, usually at or at least about 0.05 to about 5% to as much as about 10 to about 30% by weight and will be selected primarily by fluid volumes, viscosities, in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgment of the clinician but will generally be between about 0.01 and about 50 mg per kilogram of body weight, for example, between about 0.1 and about 5 mg/kg of body weight.

Lipid-therapeutic agent compositions can also be provided in kit form. The kit will typically be comprised of a container that is compartmentalized for holding the various elements of the kit. The kit will contain the particles or pharmaceutical compositions, preferably in dehydrated or concentrated form, with instructions for their rehydration or dilution and administration. In certain embodiments, the particles comprise the active agent, while in other embodiments, they do not.

Methods of Manufacture

The methods and compositions described make use of certain cationic lipids, the synthesis, preparation and characterization of which is described in, for example, in International Publication Nos. WO 2010/054401, WO 2010/054401, WO 2010/054405, WO 2009/086558; and WO 2008/042973 and WO 2010/054384, and applications referred to therein, including nos. and in U.S. Provisional Application No. 61/104,219, filed Oct. 9, 2008; No. 61/113,179, filed Nov. 10, 2008; No. 61/154,350, filed Feb. 20, 2009; No. 61/171,439, filed Apr. 21, 2009; No. 61/175,770, filed May 5, 2009; No. 61/185,438, filed Jun. 9, 2009; No. 61/225,898, and filed Jul. 15, 2009; and No. 61/234,098, filed Aug. 14, 2009; WO 2009/086558; and WO 2008/042973. See, for example, Table 1 of International Publication No. WO 2010/054401 at pages 16-21, and Tables 1-4 and 9 of U.S. Provisional Application No. 61/287,995, at pages 28-53 and 135-141.

In addition, methods of preparing lipid particles, including those associated with a therapeutic agent, e.g., a nucleic acid are described. In the methods described herein, a mixture of lipids is combined with a buffered aqueous solution of nucleic acid to produce an intermediate mixture containing nucleic acid encapsulated in lipid particles wherein the encapsulated nucleic acids are present in a nucleic acid/lipid ratio of from about 3 wt % to about 25 wt %, for example from about 5 to about 15 wt %. The intermediate mixture may optionally be sized to obtain lipid-encapsulated nucleic acid particles wherein the lipid portions are unilamellar vesicles, preferably having a diameter of from about 30 to about 150 nm, such as, from about 40 to about 90 nm. The pH is then raised to neutralize at least a portion of the surface charges on the lipid-nucleic acid particles, thus providing an at least partially surface-neutralized lipid-encapsulated nucleic acid composition.

As described above, several of these cationic lipids are amino lipids that are charged at a pH below the $pK_a$ of the amino group and substantially neutral at a pH above the $pK_a$. These cationic lipids are termed titratable cationic lipids and can be used in the formulations using a two-step process. First, lipid vesicles can be formed at the lower pH with titratable cationic lipids and other vesicle components in the presence of nucleic acids. In this manner, the vesicles will encapsulate and entrap the nucleic acids. Second, the surface charge of the newly formed vesicles can be neutralized by increasing the pH of the medium to a level above the $pK_a$ of the titratable cationic lipids present, i.e., to physiological pH or higher. Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations. Additional details concerning these uses of such titratable cationic lipids in the formulation of nucleic acid-lipid particles are provided in U.S. Pat. Nos. 6,287,591 and 6,858,225.

It is further noted that the vesicles formed in this manner provide formulations of uniform vesicle size with high content of nucleic acids. Additionally, the vesicles have a size range of from about 30 to about 150 nm, such as from about 30 to about 90 nm.

Without intending to be bound by any particular theory, it is believed that the very high efficiency of nucleic acid encapsulation is a result of electrostatic interaction at low pH. At acidic pH (e.g. pH 4.0) the vesicle surface is charged and binds a portion of the nucleic acids through electrostatic interactions. When the external acidic buffer is exchanged for a more neutral buffer (e.g., pH 7.5) the surface of the lipid particle or liposome is neutralized, allowing any external nucleic acid to be removed. See, e.g., U.S. Pat. Nos. 6,287,591 and 6,858,225.

In view of the above, methods of preparing lipid/nucleic acid formulations are described. In the methods described herein, a mixture of lipids is combined with a buffered aqueous solution of nucleic acid to produce an intermediate mixture containing nucleic acid encapsulated in lipid particles, e.g., wherein the encapsulated nucleic acids are present in a nucleic acid/lipid ratio of from about 10 wt % to about 20 wt %. The intermediate mixture may optionally be sized to obtain lipid-encapsulated nucleic acid particles wherein the lipid portions are unilamellar vesicles, preferably having a diameter of from about 30 to about 150 nm, such as from about 40 to about 90 nm. The pH is then raised to neutralize at least a portion of the surface charges on the lipid-nucleic acid particles, thus providing an at least partially surface-neutralized lipid-encapsulated nucleic acid composition.

In certain embodiments, the mixture of lipids includes at least two lipid components: a first lipid component that is selected from among lipids which have a $pK_a$ such that the lipid is cationic at pH below the $pK_a$ and neutral at pH above the $pK_a$, and a second lipid component that is selected from among lipids that prevent particle aggregation during lipid-nucleic acid particle formation. In particular embodiments, the amino lipid is a cationic lipid.

In preparing the nucleic acid-lipid particles, the mixture of lipids is typically a solution of lipids in an organic solvent. This mixture of lipids can then be dried to form a thin film or lyophilized to form a powder before being hydrated with an aqueous buffer to form liposomes. Alternatively, in a preferred method, the lipid mixture can be solubilized in a water miscible alcohol, such as ethanol, and this ethanolic solution added to an aqueous buffer resulting in spontaneous liposome formation. In most embodiments, the alcohol is used in the form in which it is commercially available. For example, ethanol can be used as absolute ethanol (100%), or as 95% ethanol, the remainder being water. See, U.S. Pat. No. 5,976,567).

In one embodiment, the mixture of lipids is a mixture of cationic lipids, neutral lipids (other than a cationic lipid), a sterol (e.g., cholesterol) and an aggregation-reducing lipid (e.g., a compound of formula (I), a PEG-DMG or PEG-DMA) in an alcohol solvent. In other embodiments, the lipid mixture consists essentially of one or more cationic lipids, a neutral lipid, cholesterol and an aggregation-reducing lipid in alcohol, such as ethanol. In further embodiments, the first solution consists of the above lipid mixture in mole percentages of about 20-70% cationic lipid: about 5-45% neutral lipid: about 20-55% cholesterol: about 0.5-15% aggregation-reducing lipid. In still further embodiments, the first solution consists essentially of a cationic lipid or a mixture of cationic lipids, DSPC, Chol and an aggregation-reducing lipid, more preferably in mole percentages of about 20-60% cationic lipid: about 5-25% DSPC: about 25-55% cholesterol: about 0.5-15% aggregation-reducing lipid. In further embodiments, the molar lipid ratio is approximately about 40/10/40/10 (mol % cationic lipid/DSPC/cholesterol/aggregation-reducing lipid), about 35/15/40/10 (mol % cationic lipid/DSPC/cholesterol/aggregation-reducing lipid) or about 52/13/30/5 (mol % cationic lipid/DSPC/cholesterol/aggregation-reducing lipid). In another group of embodiments, the neutral lipid in these compositions is replaced with POPC, DPPC, DOPE or SM.

The lipid mixture is combined with a buffered aqueous solution that may contain the nucleic acids. The buffered aqueous solution of is typically a solution in which the buffer has a pH of less than the $pK_a$ of the protonatable lipid in the lipid mixture. Examples of suitable buffers include citrate, phosphate, acetate, and MES. An exemplary buffer is citrate buffer. In certain embodiments, the buffers will be in the range of about 1-1000 mM of the anion, depending on the chemistry of the nucleic acid being encapsulated, and optimization of buffer concentration may be significant to achieving high loading levels (see, e.g., U.S. Pat. Nos. 6,287,591 and 6,858,225)). Alternatively, pure water acidified to pH 5-6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of nucleic acid in buffer can vary, but will typically be from about 0.01 mg/mL to about 200 mg/mL, such as from about 0.5 mg/mL to about 50 mg/mL.

The mixture of lipids and the buffered aqueous solution of therapeutic nucleic acids is combined to provide an intermediate mixture. The intermediate mixture is typically a mixture of lipid particles having encapsulated nucleic acids. Additionally, the intermediate mixture may also contain some portion of nucleic acids which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$ of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of formulation produced. For example, when the total volume is about 10-20 mL or less, the solutions can be combined in a test tube and stirred together using a vortex mixer. Large-scale processes can be carried out in suitable production scale glassware.

Optionally, the lipid-encapsulated therapeutic agent (e.g., nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm. Several techniques are available for sizing liposomes to a desired size. One sizing method is described in U.S. Pat. No. 4,737,323. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and about 0.5 microns, are observed. In both methods, the particle size distribution can be monitored by conventional laser-beam particle size determination. For certain methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

In certain embodiments, methods further comprise a step of neutralizing at least some of the surface charges on the lipid portions of the lipid-nucleic acid compositions. By at least partially neutralizing the surface charges, unencapsulated nucleic acid is freed from the lipid particle surface and can be removed from the composition using conventional techniques. Preferably, unencapsulated and surface adsorbed nucleic acids are removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and nucleic acid release from the surface. The released nucleic acid can then be removed via chromatography using standard methods, and then switched into a buffer with a pH above the $pK_a$ of the lipid used.

Optionally the lipid vesicles (i.e., lipid particles) can be formed by hydration in an aqueous buffer and sized using any of the methods described above prior to addition of the nucleic acid. As described above, the aqueous buffer should be of a pH below the $pK_a$ of the amino lipid. A solution of the nucleic acids can then be added to these sized, preformed vesicles. To allow encapsulation of nucleic acids into such "pre-formed" vesicles the mixture should contain an alcohol, such as ethanol. In the case of ethanol, it should be present at a concentration of about 20% (w/w) to about 45% (w/w). In addition, it may be necessary to warm the mixture of pre-formed vesicles and nucleic acid in the aqueous buffer-ethanol mixture to a temperature of about 25° C. to about 50° C. depending on the composition of the lipid vesicles and the nature of the nucleic acid. It will be apparent to one of ordinary skill in the art that optimization of the encapsulation process to achieve a desired level of nucleic acid in the lipid vesicles will require manipulation of variable such as ethanol concentration and temperature. Examples of suitable conditions for nucleic acid encapsulation are provided in the Examples. Once the nucleic acids are encapsulated within the preformed vesicles, the external pH can be increased to at least partially neutralize the surface charge. Unencapsulated and surface adsorbed nucleic acids can then be removed as described above.

Methods of Use

The lipid particles may be used to deliver a therapeutic agent to a cell, in vitro or in vivo. In certain embodiments, the therapeutic agent is a nucleic acid, which is delivered to a cell using nucleic acid-lipid particles. While the following description of various methods of using the lipid particles and related pharmaceutical compositions are exemplified by description related to nucleic acid-lipid particles, it is understood that these methods and compositions may be readily adapted for the delivery of any therapeutic agent for the treatment of any disease or disorder that would benefit from such treatment.

In certain embodiments, methods for introducing a nucleic acid into a cell are described. Preferred nucleic acids for introduction into cells are siRNA, immune-stimulating oligonucleotides, plasmids, antisense and ribozymes. These methods may be carried out by contacting the particles or compositions with the cells for a period of time sufficient for intracellular delivery to occur.

The compositions can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited, it is believed that in the case of particles taken up into the cell by endocytosis the particles then interact with the endosomal membrane, resulting in destabilization of the endosomal membrane, possibly by the formation of non-bilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 μmol and about 10 mmol. In certain embodiments, treatment of the cells with the lipid-nucleic acid compositions will generally be carried out at physiological temperatures (about 37° C.) for periods of time from about 1 to 24 hours, preferably from about 2 to about 8 hours. For in vitro applications, the delivery of nucleic acids can be to any cell grown in culture, whether of plant or animal origin, vertebrate or invertebrate, and of any tissue or type. In certain embodiments, the cells will be animal cells, for example mammalian cells, such as human cells.

In one group of embodiments, a lipid-nucleic acid particle suspension is added to about 60-80% confluent plated cells having a cell density of from about $10^3$ to about $10^5$ cells/mL, such as about $2 \times 10^4$ cells/mL. The concentration of the suspension added to the cells may be from about 0.01 to 20 μg/mL, such as about 1 μg/mL.

In another embodiment, the lipid particles can be may be used to deliver a nucleic acid to a cell or cell line (for example, a tumor cell line). Non-limiting examples of such cell lines include: HELA (ATCC Cat N: CCL-2), KB (ATCC Cat N: CCL-17), HEP3B (ATCC Cat N: HB-8064), SKOV-3 (ATCC Cat N: HTB-77), HCT-116 (ATCC Cat N: CCL-247), HT-29 (ATCC Cat N: HTB-38), PC-3 (ATCC Cat N: CRL-1435), A549 (ATCC Cat N: CCL-185), MDA-MB-231 (ATCC Cat N: HTB-26).

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630-643 (1989), and for cystic fibrosis, see Goodfellow, *Nature* 341:102-103 (1989)). Other uses for the compositions include introduction of antisense oligonucleotides in cells (see, Bennett, et al., *Mol. Pharm.* 41:1023-1033 (1992)).

Alternatively, the compositions can also be used for deliver of nucleic acids to cells in vivo, using methods which are known to those of skill in the art. With respect to delivery of DNA or mRNA sequences, Zhu, et al., *Science* 261:209-211 (1993), describes the intravenous delivery of cytomegalovirus (CMV)-chloramphenicol acetyltransferase (CAT) expression plasmid using DOTMA-DOPE complexes. Hyde, et al., *Nature* 362:250-256 (1993), describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278-281 (1989), describes the in vivo transfection of lungs of mice with a functioning prokaryotic gene encoding the intracellular enzyme, chloramphenicol acetyltransferase (CAT). Thus, the compositions can be used in the treatment of infectious diseases.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. For one example, see Stadler, et al., U.S. Pat. No. 5,286,634. Intracellular nucleic acid delivery has also been discussed in Straubringer, et al., Methods in Enzymology, Academic Press, New York. 101: 512-527 (1983); Mannino, et al., *Biotechniques* 6:682-690 (1988); Nicolau, et al., *Crit. Rev. Ther. Drug Carrier Syst.* 6:239-271 (1989), and Behr, *Acc. Chem. Res.* 26:274-278 (1993). Still other methods of administering lipid-based therapeutics are described in, for example, U.S. Pat. Nos. 3,993,754; 4,145,410; 4,235,871; 4,224,179; 4,522,803; and 4,588,578.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, et al., Am. J. Sci. 298(4):278-281 (1989)) or by direct injection at the site of disease (Culver, Human Gene Therapy, MaryAnn Liebert, Inc., Publishers, New York. pp. 70-71 (1994)).

The methods may be practiced in a variety of hosts. Examplary hosts include mammalian species, such as humans, non-human primates, dogs, cats, cattle, horses, sheep, and the like.

Dosages for the lipid-therapeutic agent particles will depend on the ratio of therapeutic agent to lipid and the administrating physician's opinion based on age, weight, and condition of the patient.

In one embodiment, a method of modulating the expression of a target polynucleotide or polypeptide is described. These methods generally comprise contacting a cell with a lipid particle that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least about 10%, about 20%, about 30%, about 40%, about 50%, or greater than 50% as compared to an appropriate control value.

For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polynucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In one embodiment, a method of modulating the expression of a polypeptide by a cell, includes providing to a cell a lipid particle that consists of or consists essentially of a mixture of one or more cationic lipids, DSPC, cholesterol and an aggregation-reducing lipid, e.g., in a mole percentages of about 20-60% cationic lipid: about 0.1-50% fusion-promoting lipid: about 5-25% DSPC: about 25-55% cholesterol: 0.5-15% aggregation-reducing lipid, wherein the lipid particle is associated with a nucleic acid capable of modulating the expression of the polypeptide. In particular embodiments, the molar lipid ratio is 0.1-50% fusion promoting lipid, with the remaining components present in a relative molar lipid ratio (mol % cationic lipid/DSPC/cholesterol/aggregation-reducing lipid) of about 40/10/40/10, about 35/15/40/10, or about 52/13/30/5. In another group of embodiments, the neutral lipid in these compositions is replaced with POPC, DPPC, DOPE or SM.

In certain embodiments, the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In additional embodiments, a method of treating a disease or disorder characterized by overexpression of a polypeptide in a subject, includes providing to the subject a pharmaceutical composition, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In one embodiment, the pharmaceutical composition comprises a lipid particle that consists of or consists essentially of a mixture of one or more cationic lipid, DSPC, cholesterol and an aggregation-reducing lipid, e.g., in a mole percentages of about 20-60% cationic lipid: about 5-25% DSPC: about 25-55% cholesterol: about 0.5-15% aggregation-reducing lipid, wherein the lipid particle is associated with the therapeutic nucleic acid. In certain embodiments, the molar lipid ratio is about 40/10/40/10 (mol % cationic lipid/DSPC/cholesterol/aggregation-reducing lipid), about 35/15/40/10 (mol % cationic lipid/DSPC/cholesterol/aggregation-reducing lipid) or about 52/13/30/5 (mol % cationic lipid/DSPC/cholesterol/aggregation-reducing lipid). In another group of embodiments, the neutral lipid in these compositions is replaced with POPC, DPPC, DOPE or SM.

In another related embodiment, a method of treating a disease or disorder characterized by underexpression of a polypeptide in a subject, includes providing to the subject a pharmaceutical composition, wherein the therapeutic agent is a plasmid that encodes the polypeptide or a functional variant or fragment thereof.

In one embodiment, the pharmaceutical composition comprises a lipid particle that consists of or consists essentially of a mixture of one or more cationic lipids, DSPC, cholesterol and an aggregation-reducing lipid, e.g., in mole percentages of about 20-60% cationic lipid: about 0.1-50% fusion-promoting lipid: about 5-25% DSPC: about 25-55% cholesterol: about 0.5-15% aggregation-reducing lipid, wherein the lipid particle is associated with the therapeutic nucleic acid. In particular embodiments, the molar lipid ratio is about 0.1-50% fusion promoting lipid, with the remaining components present in a relative molar lipid ratio (mol % cationic lipid/DSPC/cholesterol/aggregation-reducing lipid) of about 40/10/40/10, about 35/15/40/10, or about 52/13/30/5. In another group of embodiments, the neutral lipid in these compositions is replaced with POPC, DPPC, DOPE or SM.

A method of inducing an immune response in a subject, can include providing to the subject the pharmaceutical composition, wherein the therapeutic agent is an immunostimulatory oligonucleotide. In certain embodiments, the immune response is a humoral or mucosal immune response. In one embodiment, the pharmaceutical composition comprises a lipid particle that consists of or consists essentially of mixture of one or more cationic lipids, DSPC, cholesterol and an aggregation-reducing lipid, e.g., in mole percentages of about 20-60% cationic lipid: about 0.1-50% fusion-promoting lipid: about 5-25% DSPC: about 25-55% cholesterol: about 0.5-15% aggregation-reducing lipid, wherein the lipid particle is associated with the therapeutic nucleic acid. In particular embodiments, the molar lipid ratio is about 0.1-50% fusion promoting lipid, with the remaining components present in a relative molar lipid ratio (mol % cationic lipid/DSPC/cholesterol/aggregation-reducing lipid) of about 40/10/40/10, 35/15/40/10, or about 52/13/30/5. In another group of embodiments, the neutral lipid in these compositions is replaced with POPC, DPPC, DOPE or SM.

In further embodiments, the pharmaceutical composition is provided to the subject in combination with a vaccine or antigen. Thus, vaccines can include a lipid particle, which comprises an immunostimulatory oligonucleotide, and is also associated with an antigen to which an immune response is desired. In particular embodiments, the antigen is a tumor antigen or is associated with an infective agent, such as, e.g., a virus, bacteria, or parasite.

A variety of tumor antigens, infections agent antigens, and antigens associated with other disease are well known in the art and examples of these are described in references cited herein. Examples of suitable antigens include, but are not limited to, polypeptide antigens and DNA antigens. Specific examples of antigens are Hepatitis A, Hepatitis B, small pox, polio, anthrax, influenza, typhus, tetanus, measles, rotavirus, diphtheria, pertussis, tuberculosis, and *rubella* antigens. In a preferred embodiment, the antigen is a Hepatitis B recombinant antigen. In other aspects, the antigen is a Hepatitis A recombinant antigen. In another aspect, the antigen is a tumor antigen. Examples of such tumor-associated antigens are MUC-1, EBV antigen and antigens associated with Burkitt's lymphoma. In a further aspect, the antigen is a tyrosinase-related protein tumor antigen recombinant antigen. Those of ordinary skill in the art will readily appreciate additional antigens that may be suitable for use.

Tumor-associated antigens suitable for use include both mutated and non-mutated molecules that may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Examplary embodiments of tumor-associated antigens include, e.g., mutated antigens such as the protein products of the Ras p21 protooncogenes, tumor suppressor p53 and BCR-abl oncogenes, as well as CDK4, MUM1, caspase 8, and Beta catenin; overexpressed antigens such as galectin 4, galectin 9, carbonic anhydrase, aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Pathogens include, but are not limited to, infectious agents, e.g., viruses, that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, *rubella* viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Also, gram negative and gram positive bacteria serve as antigens in vertebrate animals. Such gram positive bacteria include, but are not limited to *Pasteurella* species, Staphylococci species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borelia burgdorferi, Legionella pneumophilia, Mycobacteria* sps (e.g., *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus infuenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli.*

Additional examples of pathogens include, but are not limited to, infectious fungi that infect mammals, and more particularly humans. Examples of infectious fungi include, but are not limited to: *Cryptococcus neoformans, Histoplasma capsulatum, Coccidioides immitis, Blastomyces dermatitidis, Chlamydia trachomatis, Candida albicans*. Examples of infectious parasites include *Plasmodium* such as *Plasmodium falciparum, Plasmodium malariae, Plasmodium ovale*, and *Plasmodium vivax*. Other infectious organisms (i.e., protists) include *Toxoplasma gondii*.

In one embodiment, the formulations can be used to silence or modulate a target gene such as but not limited to FVII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, SORT1 gene, XBP1 gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, tumor suppressor genes, p53 tumor suppressor gene, p53 family member DN-p63, pRb tumor suppressor gene, APC1 tumor suppressor gene, BRCA1 tumor suppressor gene, PTEN tumor suppressor gene, mLL fusion gene, BCR/ABL fusion gene, TEL/AML1 fusion gene, EWS/FLI1 fusion gene, TLS/FUS1 fusion gene, PAX3/FKHR fusion gene, AML1/ETO fusion gene, alpha v-integrin gene, Flt-1 receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene.

DEFINITIONS

A subject or patient in whom administration of the complex is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, and cats, avian species, such as chickens, turkeys, and songbirds, i.e., for veterinary medical use.

Many of the chemical groups recited in the generic formulas above are written in a particular order (for example, —OC(O)—). It is intended that the chemical group is to be incorporated into the generic formula in the order presented unless indicated otherwise. For example, a generic formula of the form X—Y—Z where Y is —OC(O)— refers to X—OC(O)—Y unless specified otherwise. It is to be understood that when a chemical group is written in a particular order, the reverse order is also contemplated unless otherwise specified. For example, in a generic formula X—Y—Z where Y is defined as —C(O)NH— (i.e., X—C(O)—NH—Z), the compound where Y is —NHC(O)— (i.e., X—NH—C(O)—Z) is also contemplated unless otherwise specified.

As used herein, an "aliphatic" group is a non-aromatic group in which carbon atoms are linked into chains, and is either saturated or unsaturated.

The term "alkyl" refers to a straight or branched chain saturated hydrocarbon moiety. In one embodiment, the alkyl group is a straight chain saturated hydrocarbon. Unless otherwise specified, the "alkyl" group contains from 1 to 24 carbon atoms. Representative saturated straight chain alkyl groups include methyl, ethyl, n-propyl, n-butyl, n-pentyl, and n-hexyl; while saturated branched alkyl groups include isopropyl, sec-butyl, isobutyl, tert-butyl, and isopentyl. Representative saturated cyclic alkyl groups (also called "cycloalkyl") include cyclopropyl, cyclobutyl, cyclopentyl, and cyclohexyl; while unsaturated cyclic alkyl groups include cyclopentenyl and cyclohexenyl.

The term "alkenyl" refers to a straight or branched chain hydrocarbon moiety having one or more carbon-carbon double bonds. In one embodiment, the alkenyl group contains 1, 2, or 3 double bonds and is otherwise saturated. Unless otherwise specified, the "alkenyl" group contains from 2 to 24 carbon atoms. Alkenyl groups include both cis and trans isomers. Representative straight chain and branched alkenyl groups include ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl.

The term "alkynyl" refers to a straight or branched chain hydrocarbon moiety having one or more carbon-carbon triple bonds. Unless otherwise specified, the "alkynyl" group contains from 2 to 24 carbon atoms. Representative straight chain and branched alkynyl groups include acetylenyl, propynyl, 1-butynyl, 2-butynyl, 1-pentynyl, 2-pentynyl, and 3-methyl-1-butynyl.

The term "acyl" refers to hydrogen, alkyl, partially saturated or fully saturated cycloalkyl, partially saturated or fully saturated heterocycle, aryl, and heteroaryl substituted carbonyl groups. For example, acyl groups include groups such as ($C_1$-$C_{20}$)alkanoyl (e.g., formyl, acetyl, propionyl, butyryl, valeryl, caproyl, and t-butylacetyl), ($C_3$-$C_{20}$)cycloalkylcarbonyl (e.g., cyclopropylcarbonyl, cyclobutylcarbonyl, cyclopentylcarbonyl, and cyclohexylcarbonyl), heterocyclic carbonyl (e.g., pyrrolidinylcarbonyl, pyrrolid-2-one-5-carbonyl, piperidinylcarbonyl, piperazinylcarbonyl, and tetrahydrofuranylcarbonyl), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, and benzo[b]thiophenyl-2-carbonyl).

The term "aryl" refers to an aromatic monocyclic, bicyclic, or tricyclic hydrocarbon ring system. Examples of aryl moieties include, but are not limited to, phenyl, naphthyl, anthracenyl, and pyrenyl.

The term "cycloalkyl" refers to a saturated cyclic or bicyclic hydrocarbon moiety such as cyclopropyl, cyclobutyl, cyclopentyl, and cyclohexyl.

The term "heterocycle" (or "heterocyclyl") refers to a non-aromatic 5- to 8-membered monocyclic, or 7- to 12-membered bicyclic, or 11- to 14-membered tricyclic ring system which is either saturated or unsaturated, and which contains from 1 to 3 heteroatoms if monocyclic, 1-6 heteroatoms if bicyclic, or 1-9 heteroatoms if tricyclic, independently selected from nitrogen, oxygen and sulfur, and wherein the nitrogen and sulfur heteroatoms may be optionally oxidized, and the nitrogen heteroatom may be optionally quaternized. For instance, the heterocycle may be a cycloalkoxy group. The heterocycle may be attached to the rest of the molecule via any heteroatom or carbon atom in the heterocycle. Heterocycles include, but are not limited to, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

The term "heteroaryl" refers to an aromatic 5-8 membered monocyclic, 7-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively). The heteroaryl groups herein described may also contain fused rings that share a common carbon-carbon bond.

The term "substituted", unless otherwise indicated, refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and an aliphatic group. It is understood that the substituent may be further substituted. Exemplary substituents include amino, alkylamino, dialkylamino, and cyclic amino compounds.

The term "halogen" or "halo" refers to fluoro, chloro, bromo and iodo.

In some embodiments, the methods may require the use of protecting groups. Protecting group methodology is well known to those skilled in the art (see, for example, *Protective Groups in Organic Synthesis*, Green, T. W. et. al., Wiley-Interscience, New York City, 1999). Briefly, protecting groups are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

The compounds may be prepared by known organic synthesis techniques.

General References

The following references provide background information that may be pertinent to the present invention.

The oligoribonucleotides and oligoribonucleosides may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Modifications described in International Publication Nos. WO 00/44895, WO01/75164, and WO02/44321 can also be used herein.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 and 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7, 651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligoribonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in International Publication Nos. WO 92/20822 WO and WO 92/20823. Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. *Nucleic Acids Res.* 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033. Peptide Nucleic Acids (PNAs) can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references disclosed therein.

Nucleobases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908.

Preparation of Oligonucleotide Conjugates

U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; and 6,559,279 describe the preparation of oligonucleotide conjugates.

EXAMPLES

The present invention will now be further described by way of the following non-limiting examples. In applying the disclosure of these examples, it should be kept clearly in mind that the examples are merely illustrative of the present invention and should not be construed as limiting the scope of the invention in any way as many variations and equivalents that are encompassed by the present invention will become apparent to those skilled in the art upon reading the present disclosure.

The following abbreviations are used herein: Py (pyridine), Ms (methane sulfonyl), DMAP (4-dimethylamino pyridine), DCM (dichloromethane), DMF (dimethylformamide), THF (tetrahydrofuran), DSC (N,N'-disuccinimidyl carbonate), TEA (triethylamine), m-PEG-amine and m-PEG-NH$_2$ (monomethoxy polyethylene glycol-amine), MALDI (matrix-assisted laser desorption and ionization).

Example 1

Synthesis of PEG-C-DSMO (8)

PEG-C-DSMO (8) may be prepared according to the synthetic scheme outline below.

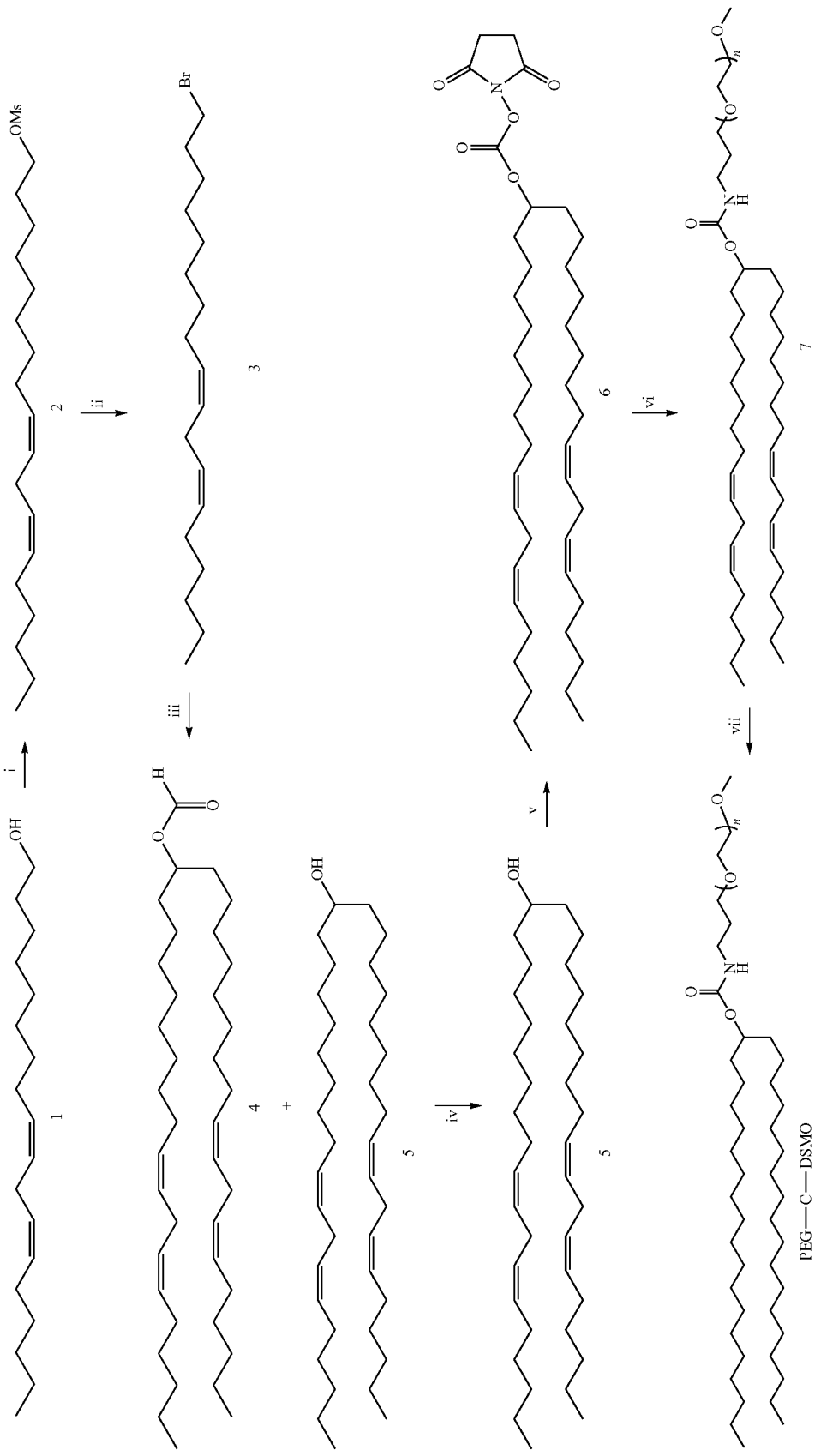

Step 1: Synthesis of methanesulfonic acid octadeca-9,12-dienyl ester (2)

To a solution of the alcohol 1 (26.6 g, 100 mmol) in dichloromethane (100 mL), triethylamine (13.13 g, 130 mmol) was added and this solution was cooled in an ice-bath. To this cold solution, a solution of mesyl chloride (12.6 g, 110 mmol) in dichloromethane (60 mL) was added dropwise and after the completion of the addition, the reaction mixture was allowed to warm to ambient temperature and stirred overnight. The TLC of the reaction mixture showed the completion of the reaction. The reaction mixture was diluted with dichloromethane (200 mL), washed with water (200 mL), satd. NaHCO$_3$ (200 mL), brine (100 mL) and dried (NaSO$_4$). The organic layer was concentrated to get the crude product which was purified by column chromatography (silica gel) using 0-10% Et$_2$O in hexanes. The pure product fractions were combined and concentrated to obtain the pure product (2) as colorless oil (30.6 g, 89%). $^1$H NMR (CDCl$_3$, 400 MHz) δ=5.42-5.21 (m, 4H), 4.20 (t, 2H), 3.06 (s, 3H), 2.79 (t, 2H), 2.19-2.00 (m, 4H), 1.90-1.70 (m, 2H), 1.06-1.18 (m, 18H), 0.88 (t, 3H). $^{13}$C NMR (CDCl$_3$) δ=130.76, 130.54, 128.6, 128.4, 70.67, 37.9, 32.05, 30.12, 29.87, 29.85, 29.68, 29.65, 29.53, 27.72, 27.71, 26.15, 25.94, 23.09, 14.60. MS. Molecular weight calculated for C$_{19}$H$_{36}$O$_3$S, Cal. 344.53, Found 343.52 (M-H$^-$).

Step 2: Synthesis of 18-Bromo-octadeca-6,9-diene (3)

The mesylate (2) (13.44 g, 39 mmol) was dissolved in anhydrous ether (500 mL) and to it the MgBr.Et$_2$O complex (30.7 g, 118 mmol) was added under argon and the mixture was refluxed under argon for 26 h after which the TLC showed the completion of the reaction. The reaction mixture was diluted with ether (200 mL) and ice-cold water (200 mL) was added to this mixture and the layers were separated. The organic layer was washed with 1% aqueous K$_2$CO$_3$ (100 mL), brine (100 mL) and dried (Anhyd. Na$_2$SO$_4$). Concentration of the organic layer provided the crude product which was further purified by column chromatography (silica gel) using 0-1% Et$_2$O in hexanes to isolate the bromide 3 (12.6 g, 94%) as a colorless oil. $^1$H NMR (CDCl$_3$, 400 MHz) δ=5.41-5.29 (m, 4H), 4.20 (d, 2H), 3.40 (t, J=7 Hz, 2H), 2.77 (t, J=6.6 Hz, 2H), 2.09-2.02 (m, 4H), 1.88-1.00 (m, 2H), 1.46-1.27 (m, 18H), 0.88 (t, J=3.9 Hz, 3H). $^{13}$C NMR (CDCl$_3$) δ=130.41, 130.25, 128.26, 128.12, 34.17, 33.05, 31.75, 29.82, 29.57, 29.54, 29.39, 28.95, 28.38, 27.42, 27.40, 25.84, 22.79, 14.28.

Step 3: Synthesis of Dilinoleyl Methanol (5)

To a flame dried 500 mL RB flask, freshly activated Mg turnings (2.4 g, 100 mmol) were added and the flask was equipped with a magnetic stir bar, an addition funnel and a reflux condenser. This set-up was degassed and flushed with argon and 10 mL of anhydrous ether was added to the flask via syringe. The bromide (3) (26.5 g, 80.47 mmol) was dissolved in anhydrous ether (50 mL) and added to the addition funnel. About 5 mL of this ether solution was added to the Mg turnings while stirring vigorously. An exothermic reaction was noticed (to confirm/accelerate the Grignard reagent formation, 5 mg of iodine was added and immediate decolorization was observed confirming the formation of the Grignard reagent) and the ether started refluxing. The rest of the solution of the bromide was added dropwise while keeping the reaction under gentle reflux by cooling the flask in water. After the completion of the addition the reaction mixture was kept at 35° C. for 1 h and then cooled in ice bath. Ethyl formate (2.68 g, 36.2 mmol) was dissolved in anhydrous ether (40 mL) and transferred to the addition funnel and added dropwise to the reaction mixture with stirring. An exothermic reaction was observed and the reaction mixture started refluxing. After the initiation of the reaction the rest of the ethereal solution of formate was quickly added as a stream and the reaction mixture was stirred for a further period of 1 h at ambient temperature. The reaction was quenched by adding 10 mL of acetone dropwise followed by ice cold water (60 mL). The reaction mixture was treated with aq. H$_2$SO$_4$ (10% by volume, 300 mL) until the solution became homogeneous and the layers were separated. The aq. phase was extracted with ether (2×100 mL). The combined ether layers were dried (Na$_2$SO$_4$) and concentration of the organic layer over reduced pressure provided the crude product as a mixture of required dilinoleylmethanol along with minor amounts of O-formylated product. This crude product was re-dissolved in THF (100 mL) and treated with ice-cold aqueous NaOH (10%) and heated at 40° C. for 18 h after which the TLC (10% ether in hexanes) showed the complete conversion of the O-formylated product to the required dilinoleylmethanol. The reaction mixture was cooled and was extracted with ether (3×100 mL) and the combined organic layers were washed with brine and dried over sodium sulfate. Filtration followed by concentration of the organic layer provided the crude product. The thus obtained crude product was purified by column chromatography using 60-120 mesh silica gel using 4% ether in hexanes. Concentration of the pure product fractions provided the pure product (15.4 g, 86%) as a colorless liquid. NMR (400 MHz, CDCl$_3$) δ 5.47-5.24 (m, 8H), 3.56 (dd, J=6.8, 4.2, 1H), 2.85-2.66 (m, 4H), 2.12-1.91 (m, 9H), 1.50-1.17 (m, 46H), 0.98-0.76 (m, 6H). $^{13}$C NMR (101 MHz, CDCl$_3$) δ 130.41, 130.37, 128.18, 128.15, 77.54, 77.22, 76.91, 72.25, 37.73, 31.75, 29.94, 29.89, 29.83, 29.73, 29.58, 29.53, 27.46, 27.43, 25.89, 25.86, 22.80, 14.30.

Step 4: Synthesis of Active Ester (6)

Dilinoleyl methanol (20.66 g, 39.1 mmol), DSC (15.00 g, 58.6 mmol) and triethylamine (16 mL, 117 mmol) were taken together in DCM (200 mL) and heated the reaction mixture for 2 days and over the weekend (3 days) at room temperature. Reaction was monitored by TLC and the reaction mixture was diluted with DCM/hexane and washed with water (300 mL) and dried organic layer over sodium sulfate. Solvent was removed and the residue was purified by silica gel flash chromatography using ethyl acetate/hexane (0-30%) to get product as a color less oil (15.7 g, 60%). This compound used as such for the next reaction.

Step 5: Synthesis of (7)

mPEG-NH$_2$ (4.00 g, 1.86 mmol) and compound 6 (1.87 g, 2.79 mmol) were dissolved in DCM and cooled in an ice-water mixture. Pyridine (5 mL) was added to the reaction mixture and stirred the mixture overnight. TLC checked and the reaction mixture diluted with DCM, washed with water and brine. Organic layer was dried over sodium sulfate and removed the volatiles. The crude product was purified by silica gel flash chromatography (10% EtOAc/DCM, EtOAc then 2-15% MeOH/DCM to get the product as white solid (3.36 g, 65%). $^1$H NMR (400 MHz, CDCl$_3$) δ 5.30 (dd, J=9.8, 6.5 Hz, 10H), 5.04 (s, 1H), 4.66 (s, 1H), 3.77 (s, 1H), 3.70-3.38 (m, 301H), 3.36-3.30 (m, 4H), 3.23 (s, 3H), 2.72 (s, 5H), 2.00 (s, 10H), 1.72 (s, 2H), 1.33 (d, J=84.4 Hz, 54H), 0.95-0.72 (m, 6H). MALDI MW calculated ~2800; Found ~2800.

Step 6: Synthesis of PEG-C-DSMO (8)

Compound (7) (1.57 g, 0.603 mmol) was dissolved in Methanol (100 mL) and hydrogenated under balloon pressure using Pd/C (150 mg, 10 wt % degusa type wet) overnight. Reaction was monitored by TLC and filtered through a small pad of celite and washed with methanol.

Solvents were removed and the crude product was purified by silica gel chromatography (2-15% MeOH/DCM) to get the compound as a white solid (1.088 g, 69%). $^1$H NMR (400 MHz, CDCl3) δ 5.06 (s, 1H), 4.63 (s, 1H), 3.81-3.06 (m, 308H), 2.30 (d, J=6.8 Hz, 1H), 1.82-1.59 (m, 2H), 1.44 (d, J=28.3 Hz, 7H), 1.18 (s, 79H), 0.80 (t, J=6.9 Hz, 6H). MALDI MW calculated ~2800; Found ~2800.

Alternate Synthesis of PEG-C-DMSO (8)

PEG-C-DMSO (8) may also be prepared according to the synthetic scheme outline below.

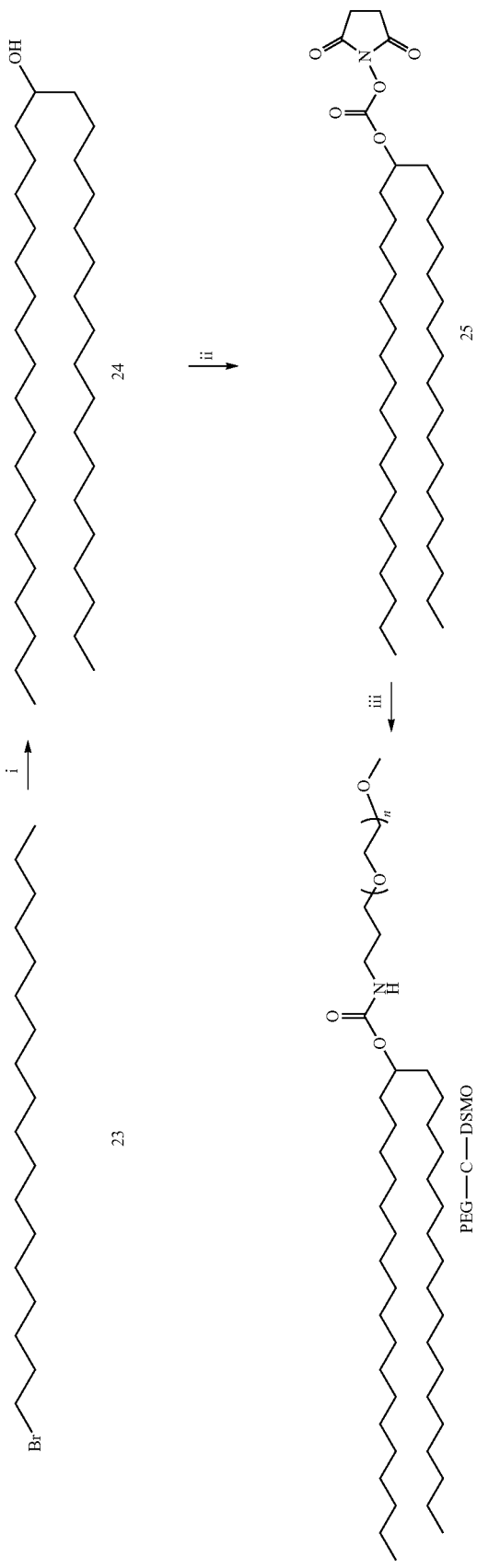

In a similar procedure to that used for the synthesis of dilinoleylmethanol 5, commercially available stearyl bromide is converted to distearylmethanol 24. Conversion of the distearylmethanol 24 to the activated succinimidyl carbonate 25 is achieved by using a similar procedure to that used for the synthesis of 6. Treatment of the activated carbonate 10 with mPEG-amine affords the product PEG-C-DSMO.

Example 2

Synthesis of PEG-C-DMSA (13)

PEG-C-DMSA (13) may be prepared according to the synthetic scheme outline below.

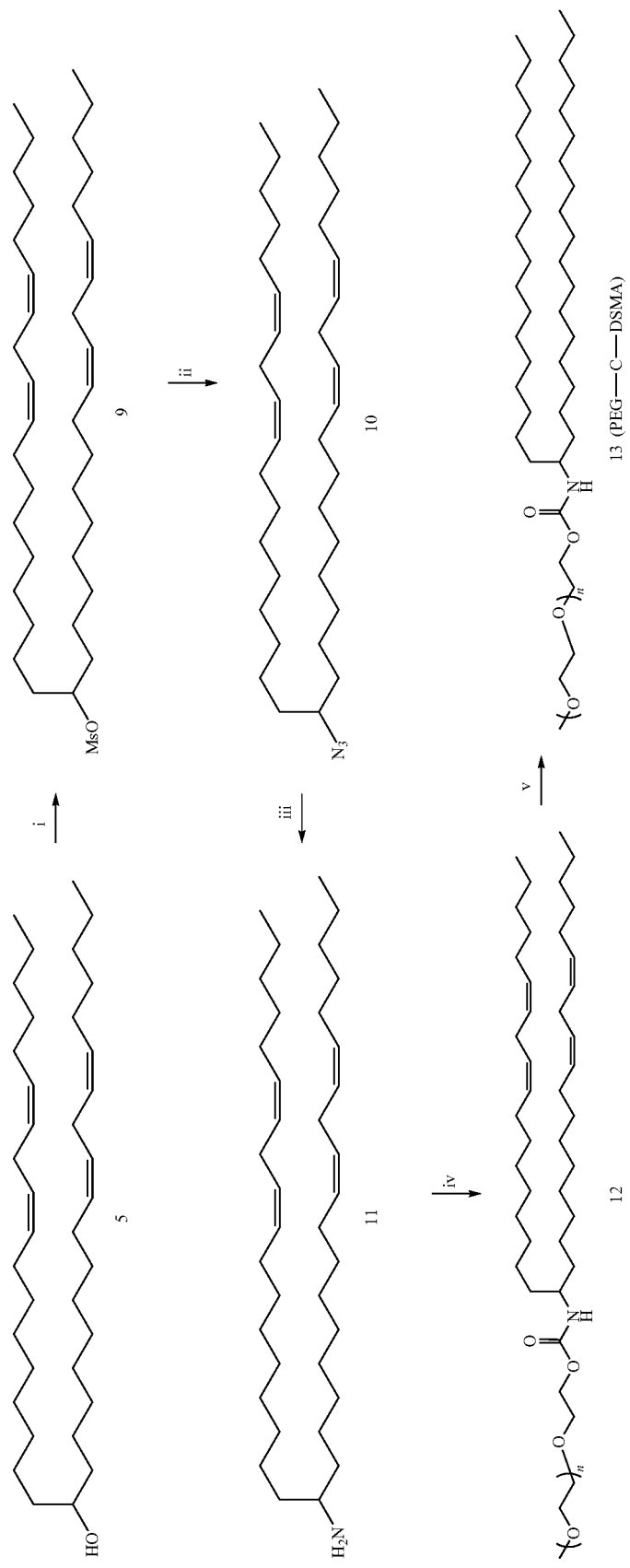

Step 1: Synthesis of (9)

To a solution of (5) (50 g, 95 mmol) in DCM (400 ml) under argon atmosphere, was added TEA (53 mL, 378 mmol) and DMAP (1.2 g, 9.5 mmol) and stirred at room temperature. Reaction mass was cooled to −5° C. and a solution of mesyl chloride (15 mL, 190 mmol) in DCM (100 mL) was added slowly at temperature below −5° C. and allowed to warm to RT after addition. After 30 minutes (TLC), reaction mass was quenched with ice cold water (20 ml). Organic layer was separated, washed with 1N HCl (30 ml), water, brine, dried over sodium sulfate and evaporated at reduced pressure to obtain pure product (55 g, 95.5%) as yellow liquid. 1H NMR (400 MHz, CDCl$_3$): δ 0.89 (t, 6H, J=6.8), 1.2-1.5 (m, 36H), 1.67 (m, 4H), 2.05 (q, 8H, J1=6.8, J2=6.8), 2.77 (t, 4H, J=6.4), 2.99 (s, 3H), 4.71 (m, 1H) and 5.36 (m, 8H).

Step 2: Synthesis of (10)

To a solution of (9) (50 g, 82 mmol) in DMF (500 mL) under argon atmosphere, was added NaN$_3$ (27 g, 410 mmol) and heated to 70° C. and maintained the temperature for four hours (TLC). The mixture was diluted with water and extracted with ethyl acetate (3×250 mL). The organic layer was washed with water, brine, dried over Na$_2$SO$_4$ and evaporated at reduced pressure to give crude product, which was purified by silica gel chromatography using hexane/ether as eluent. The product was eluted at 2% ether hexane to afford (10) (36 g, 86%) as a pale yellow liquid. $^1$H NMR (400 MHz, CDCl3): δ 0.90 (t, 8H), 1.30 (m, 36H), 1.49 (t, 4H, J=6.4 Hz) 2.04 (q, 8H, J1=7.6, J2=14 Hz), 2.77 (t, 4H, J=6.4 Hz), 3.22 (m, 1H), 5.34 (m, 8H). $^{13}$C NMR (400 MHz, CDCl$_3$): δ 14.1, 22.5, 25.6, 26.1, 27.2, 29.2, 29.3, 29.45, 29.65, 31.5, 34.1, 63.1, 127.9, and 130.1. IR (KBr): 2098.

Step 3: Synthesis of (11)

To a suspension of lithium aluminiumhydride in dry THF at argon atmosphere, was added (10) in THF at 0° C. drop-wise. It was then allowed to warm to room temperature and stirred for 20 hrs at RT (TLC). It was cooled to 0° C. and quenched with saturated solution of sodium sulfate. The quenched mass was filtered through celite bed and washed with ethyl acetate. The combined filtrate was evaporated at reduced pressure to obtain crude product, which was purified by silica gel chromatography using 10% ethyl acetate in hexane to afford pure product 11 (3.7 g, yield: 71%) as a pale brown liquid, HPLC: 93.8%. $^1$H NMR (400 MHz, CDCl$_3$): δ 0.87 (t, 6H, J=6.8 Hz), 1.27 (m, 48H), 2.03 (q, 8H, J=6.8 Hz), 2.60 (d, 2H, J=4.0 Hz), 2.76 (t, 4H, J=6.4 Hz), 5.31 (m, 8H). $^{13}$CNMR (100 MHz, CDCl$_3$): δ 14.1, 22.6, 25.6, 26.8, 27.1, 27.2, 29.3, 29.5, 29.6, 30.1, 31.5, 40.9, 45.2, 128.0, 130.1.

Step 4: Synthesis of (12)

Compound (11) (1.00 g, 1.89 mmol) and mPEG-active ester (3.00 g, 1.42 mmol) were dissolved in DCM (100 mL) and cooled in an ice-water bath. Pyridine (5 mL) was added and the reaction mixture stirred overnight. TLC checked and the reaction mixture diluted with DCM, washed with water and brine. Organic layer was dried over sodium sulfate and removed the solvent. The crude product was purified by silica gel flash chromatography (10% EtOAc/DCM, EtOAc followed by 2-15% MeOH/DCM) to afford the product as a white solid (2.50 g, 71%). $^1$H NMR (400 MHz, CDCl3) δ 5.44-5.21 (m, 9H), 4.48 (d, J=9.2 Hz, 1H), 4.26-4.11 (m, 3H), 3.78 (dd, J=8.7, 3.4 Hz, 2H), 3.74-3.41 (m, 229H), 3.35 (s, 4H), 2.74 (t, J=6.3 Hz, 5H), 2.10-1.88 (m, 10H), 1.50-1.11 (m, 51H), 0.86 (t, J=6.8 Hz, 6H) and MALDI MW calculated ~2550; Found ~2550.

Step 5: Synthesis of PEG-C-DSMA (13)

Compound (12) (1.50 g, 0.600 mmol) was dissolved in methanol (100 mL) and hydrogenated under balloon pressure using Pd/C (150 mg, 10 wt % degusa type wet) overnight. Reaction was monitored by TLC and filtered through a small pad of celite and washed with methanol. Solvents were removed and the crude product was purified by silica gel chromatography (2-15% MeOH/DCM) to afford the product (13) as a white solid (1.287 g, 85%). $^1$H NMR (400 MHz, CDCl$_3$) δ 4.48 (d, J=9.1 Hz, 1H), 4.26-4.02 (m, 3H), 3.85-3.69 (m, 1H), 3.69-3.35 (m, 239H), 3.30 (s, 4H), 2.30 (s, 1H), 1.54-0.95 (m, 88H), 0.80 (t, J=6.7 Hz, 6H). MALDI MW calculated ~2550; Found ~2550.

Alternate Synthesis of PEG-C-DSMA (13)

PEG-C-DSMA (13) may also be prepared according to the synthetic scheme outline below.

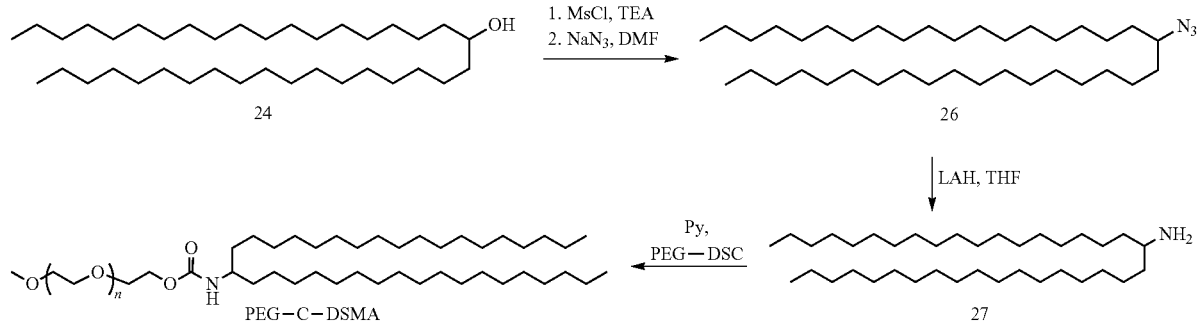

In a similar procedure used for the synthesis of 13, the distearyl alcohol 24 is converted to the corresponding azide 26 by treating the corresponding mesylate with sodium azide in DMF. The thus obtained azide, on treatment with LAH in refluxing THF, affords the amine 27. Treatment of the distearylmethylamine 27 with commercial PEG-DSC in the presence of pyridine affords the coupled product PEG-C-DSMA (13).

Example 3

Synthesis of PEG-S-DMSO (16)

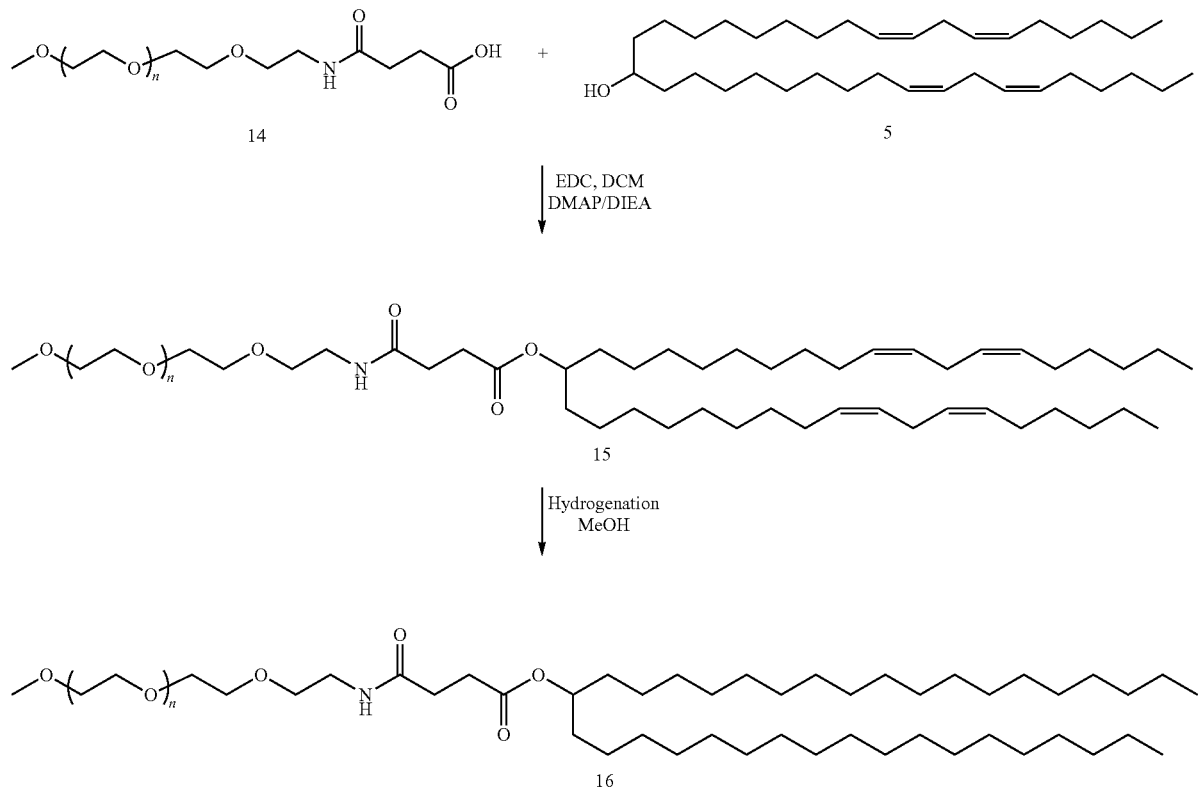

Synthesis of Compound 15

PEG-COOH 14 (5.00 g, 2.5 mmol) and DiLin-OH 5 were taken in DCM and treated with EDC (0.718 g, 1.5 eq), DMAP (100 mg, 0.819 mmol) and DIEA (0.869 mL, 2 eq). The resulting mixture was stirred at ambient temperature overnight and diluted with DCM. The organic layer was washed with water (2×100 mL) and dried over sodium sulfate. The crude product was purified by chromatography. First it was eluted with 10% EtOAC/DCM then 100% EtOAc to remove unreacted lipids. This was followed by 2-15% MeOH/DCM to afford the product (3.36 g, 53%) as a white solid. $^1$H NMR (400 MHz, CDCl$_3$) δ 7.27 (d, J=9.8 Hz, 1H), 6.20 (t, J=5.1 Hz, 1H), 5.43-5.19 (m, 9H), 4.83 (p, J=6.0 Hz, 1H), 3.85-3.72 (m, 2H), 3.71-3.48 (m, 255H), 3.46-3.39 (m, 4H), 3.36 (d, J=0.7 Hz, 4H), 2.75 (t, J=6.3 Hz, 5H), 2.62 (t, J=7.1 Hz, 3H), 2.45 (t, J=7.1 Hz, 2H), 2.02 (q, J=6.4 Hz, 10H), 1.45 (t, J=16.2 Hz, 5H), 1.31 (ddd, J=23.6, 14.9, 10.1 Hz, 46H), 0.87 (t, J=6.7 Hz, 6H). MALDI MW calculated ~2570; found ~2570.

Synthesis of PEG-S-DMSO (16)

Compound 15 (1.00 g, 0.357 mmol) was dissolved in methanol (100 mL) and hydrogenated under balloon pressure using Pd/C (100 mg, 10 wt % degusa type wet) overnight. The reaction mixture was then filtered through a small pad of celite and washed with methanol. Solvents were removed and the crude product was purified by silica gel chromatography (2-15% MeOH/DCM) to afford the compound as a white solid (0.950, 94%). $^1$H NMR (400 MHz, CDCl$_3$) δ 6.38 (s, 1H), 4.91-4.77 (m, 1H), 3.86-3.75 (m, 1H), 3.74-3.39 (m, 187H), 3.39-3.34 (m, 3H), 2.63 (t, J=7.1 Hz, 2H), 2.47 (t, J=7.1 Hz, 2H), 1.96 (s, 6H), 1.49 (d, J=5.9 Hz, 3H), 1.27 (s, 2H), 1.36-1.06 (m, 56H), 0.87 (t, J=6.8 Hz, 4H). MALDI MW calculated ~2600; found ~2605.

Example 4

Synthesis of PEG-S-DSMA (18)

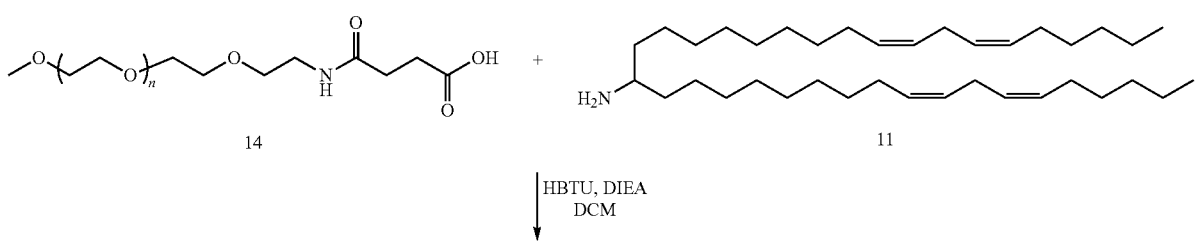

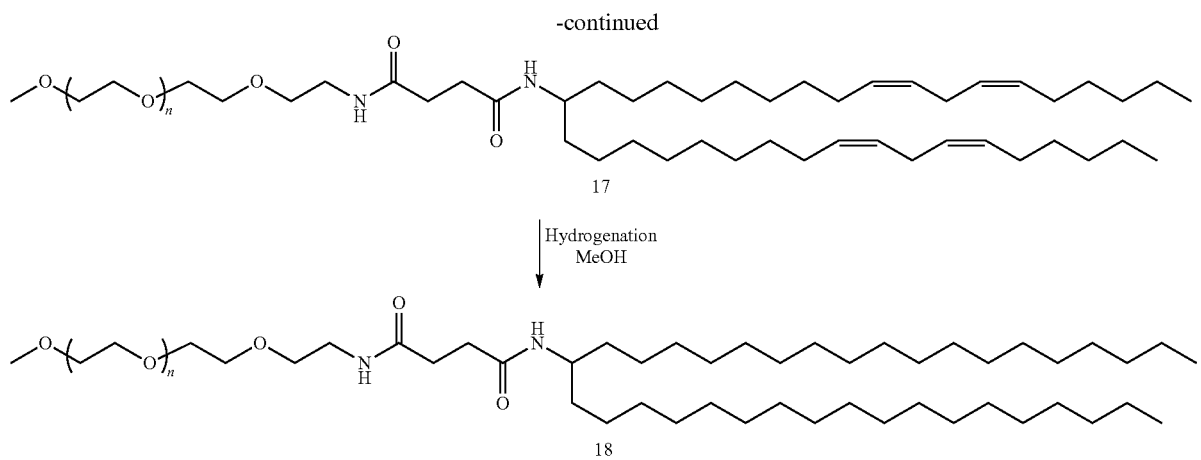

17

Hydrogenation
MeOH

18

Synthesis of Compound 17

PEG-COOH 14 (3.00 g, 1.5 mmol) and DiLin-NH$_2$ 11 (0.949 g, 1.79 mmol) were taken in DCM and treated with HBTU (1.137 g, 2 eq) and DIEA (0.780 mL, 3 eq). The mixture was stirred at ambient temperature overnight then diluted with DCM. The organic layer was washed with water (2×100 mL) then dried over sodium sulfate. The crude product was purified by chromatography. First it was eluted with 10% EtOAC/DCM then 100% EtOAc to remove unreacted lipids. This was followed by 2-15% MeOH/DCM to afford the product (1.227 g, 38%) and mixture 2.00 g as white solids. $^1$H NMR (400 MHz, CDCl$_3$) δ 6.41 (t, J=5.1 Hz, 1H), 5.80 (d, J=9.1 Hz, 1H), 5.46-5.21 (m, 7H), 3.80 (dd, J=9.9, 5.2 Hz, 3H), 3.73-3.50 (m, 175H), 3.49-3.40 (m, 3H), 3.38 (d, J=11.7 Hz, 3H), 2.76 (t, J=6.4 Hz, 3H), 2.56-2.41 (m, 4H), 2.01 (dd, J=18.5, 12.1 Hz, 9H), 1.49-1.12 (m, 36H), 0.87 (t, J=6.7 Hz, 4H). MALDI MW calculated ~2598; found ~2598.

Synthesis of PEG-S-DSMA (18)

Compound 17 (1.00 g, 0.358 mmol) was dissolved in methanol (100 mL) and hydrogenated under balloon pressure using Pd/C (100 mg, 10 wt % degusa type wet) overnight. The reaction mixture was then filtered through a small pad of celite and washed with methanol. Solvents were removed and the crude product was purified by silica gel chromatography (2-15% MeOH/DCM) to afford the compound as a white solid (0.850, 84%). $^1$H NMR (400 MHz, CDCl$_3$) δ 6.39 (dd, J=13.5, 8.4 Hz, 1H), 5.76 (dd, J=37.7, 9.9 Hz, 1H), 3.61 (d, J=5.3 Hz, 221H), 3.34 (s, 3H), 2.54-2.41 (m, 4H), 2.38-2.32 (m, 1H), 1.22 (s, 75H), 0.84 (t, J=6.8 Hz, 5H). MALDI MW calculated ~2650; found ~2650.

Example 5

Synthesis of Compound 22

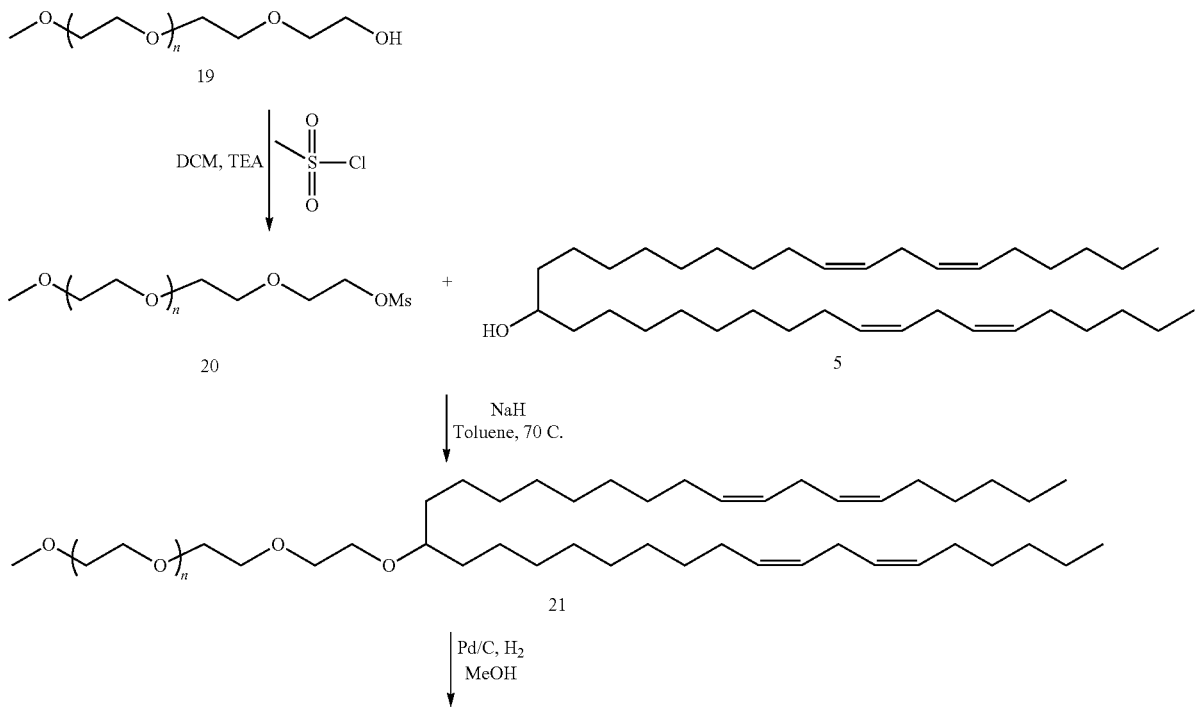

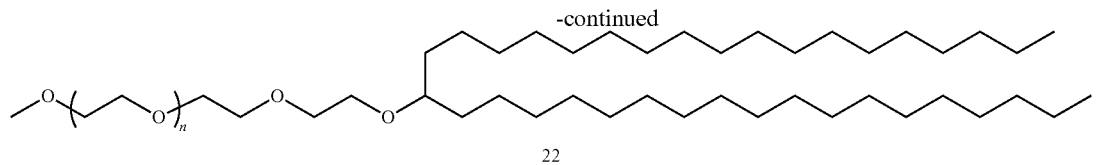

22

Synthesis of (21)

DiLin-OH 5 (5 mmol g, 1.79 mmol) was dissolved in toluene (100 mL) and NaH (0.400 g, 60 wt % in mineral oil) was added. The resulting mixture was stirred for 30 minutes at room temperature. A solution of PEG-mesilate 20 (5.00 g, 2.5 mmol) in toluene (50 mL) was then added and the mixture stirred for 10 minutes. The mixture was then heated at 70° C. for 5 days. Then quenched with cold water. Solvents were removed and the residue was dissolved in DCM, washed with water and brine. The organic layer was dried over sodium sulfate and the crude product was purified by silica gel chromatography to afford the product as white solid (1.27 g) containing some unreacted PEG precursor. MALDI MW calculated ~2455; found ~2455.

Synthesis of (22)

Compound 21 (1.20 g, 0.48 mmol) was dissolved in methanol (100 mL) and hydrogenated under balloon pressure using Pd/C (120 mg, 10 wt % degusa type wet) overnight. The reaction mixture was then filtered through a small pad of celite and washed with methanol. Solvents were removed and the crude product was purified by silica gel chromatography (2-15% MeOH/DCM) to afford 22 as a white solid (0.600 g, 51%) after multiple purifications. MALDI MW calculated ~2450; found ~2450.

Example 6

Synthesis of PEG-C-DSEA (30)

and evaporated at reduced pressure to afford pure product mesylate (55 g, 95.5%) as a yellow liquid. $^1$H NMR (400 MHz, CDCl$_3$): δ 0.89 (t, 6H, J=6.8), 1.2-1.5 (m, 36H), 1.67 (m, 4H), 2.05 (q, 8H, J1=6.8, J2=6.8), 2.77 (t, 4H, J=6.4), 2.99 (s, 3H), 4.71(m, 1H) and 5.36 (m, 8H).

To a stirred solution of sodium cyanide (1.70 g, 0.0330 mol) in DMF, was added mesylate (10 g, 0.0165 mol) in DMF (100 mL) and the mixture was slowly heated to 55° C. for 24 hrs. It was then cooled to room temperature, diluted with water and extracted with ethyl acetate several times. The combined organic layers were washed with water, brine, dried over sodium sulfate and evaporated at reduced pressure to afford crude product, which was purified by silica gel chromatography using 1% ether/hexane to afford the product as a pale yellow liquid (5.80 g, 62%). $^1$H NMR (400 MHz, CDCl$_3$): δ 0.87 (t, 6H, J=6.8 Hz), 1.25(m, 38H), 1.52 (m, 4H), 2.03 (q, 8H, J=6.8 Hz, J=6.8 Hz), 2.47 (m, 1H), 2.76 (t, 4H, J=6.4 Hz), 5.32 (m, 8H).

Synthesis of (29)

Compound 28 (5.2 g, 0.0097 mol) in THF was added drop-wise to a cooled suspension of LAH (1.50 g, 0.0387 mol) in THF (52 ml) at 0° C. under an argon atmosphere. After addition, the mixture was allowed to warm to RT and stirred for 20 hrs. The mixture was then cooled to 0° C. and quenched with a saturated solution of sodium sulfate (10 ml) followed by ethyl acetate. It was then filtered through a bed of celite and washed with ethyl acetate. The combined organic filtrate was evaporated at reduced pressure to obtain

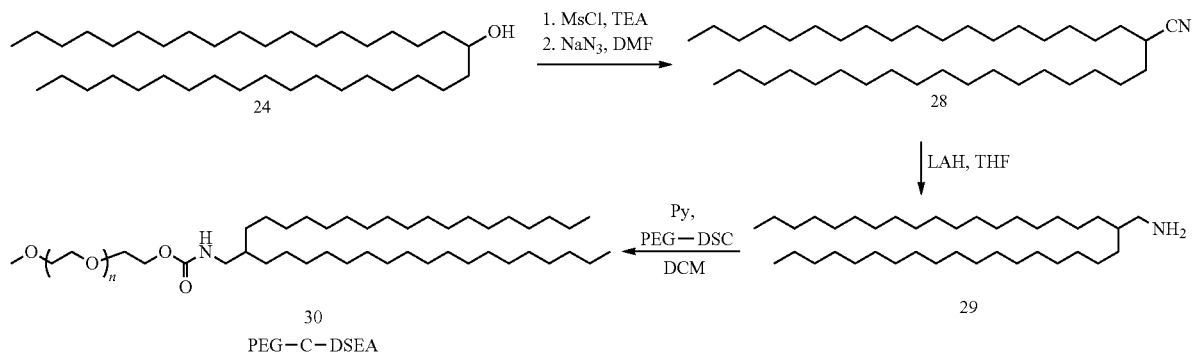

Synthesis of 28

TEA (53 mL, 378 mmol) and DMAP (1.2 g, 9.5 mmol) were added to a solution of 24 (50 g, 95 mmol) in DCM (400 ml) under an atmosphere of argon, and the resulting mixture was stirred at room temperature under the argon atmosphere. The reaction mass was cooled to −5° C. and a solution of mesyl chloride (15 mL, 190 mmol) in DCM (100 ml) was added slowly at a temperature below −5° C. Once addition was complete, the reaction mixture was then allowed to warm to RT. After 30 minutes, the reaction mass was quenched with ice cold water (20 ml). The organic layer was separated, washed with 1N HCl (30 ml), water, brine, dried over sodium sulfate crude product, which was purified by silica gel chromatography using 10% ethyl acetate in hexane to afford 29 as pale brown liquid (3.70 g, 71%). $^1$H NMR (400 MHz, CDCl$_3$): δ 0.87(t, 6H, J=6.8 Hz), 1.27(m, 48H), 2.03(q, 8H, 6.8 Hz, 6.8 Hz), 2.60(d, 2H, J=4.0 Hz), 2.76(t, 4H, J=6.4 Hz), 5.31(m, 8H). $^{13}$C NMR (100 MHz, CDCl$_3$): δ 14.1, 22.6, 25.6, 26.8, 27.1, 27.2, 29.3, 29.5, 29.6, 30.1, 31.5, 40.9, 45.2, 128.0, 130.1. Mass 543 (M+).

Synthesis of 30 (PEG-C-DSEA)

Amine 29 was treated with PEG-DSC in a manner similar to that described above to afford PEG-C-DSEA (30).

Example 7

FVII In Vivo Evaluation Using the Cationic Lipid Derived Liposomes

C57BL/6 mice (Charles River Labs, MA) receive either saline or siRNA in desired formulations via tail vein injection at a volume of 0.01 mL/g. At various time points post-administration, animals are anesthesized by isofluorane inhalation and blood is collected into serum separator tubes by retro orbital bleed. Serum levels of Factor VII protein are determined in samples using a chromogenic assay (Coaset Factor VII, DiaPharma Group, OH or Biophen FVII, Aniara Corporation, OH) according to manufacturer protocols. A standard curve is generated using serum collected from saline treated animals. In experiments where liver mRNA levels were assessed, at various time points post-administration, animals are sacrificed and livers are harvested and snap frozen in liquid nitrogen. Frozen liver tissue is ground into powder. Tissue lysates were prepared and liver mRNA levels of Factor VII and apoB are determined using a branched DNA assay (QuantiGene Assay, Panomics, CA).

Example 8

Determination of Efficacy of Lipid Particle Formulations Containing Various Cationic Lipids Using an In Vivo Rodent Factor VII Silencing Model Factor VII (FVII), a prominent protein in the coagulation cascade, is synthesized in the liver (hepatocytes) and secreted into the plasma. FVII levels in plasma can be determined by a simple, plate-based colorimetric assay. As such, FVII represents a convenient model for determining sirna-mediated downregulation of hepatocyte-derived proteins, as well as monitoring plasma concentrations and tissue distribution of the nucleic acid lipid particles and siRNA.

| Duplex | Sequence 5'-3' | SEQ ID NO: | Target |
|---|---|---|---|
| AD-1661 | GGAfUfCAfUfCfUfCAAGfUfCfUfUAfCdTsdT GfUAAGAfCfUfUGAGAfUGAfUfCfCdTsdT | | FVII |

Lower case is 2'OMe modification and Nf is a 2'F modified nucleobase, dT is deoxythymidine, s is phosphothioate The cationic lipids shown above are used to formulate liposomes containing the AD-1661 duplex using an in-line mixing method, as described in e.g., U.S. provisional patent application 61/228,373. Lipid particles are formulated using the following mole percentages: 50% cationic lipid/10% distearoylphosphatidylcholine (DSPC)/38.5% cholesterol/1.5% aggregation-reducing lipid.

General Protocol for in-line Mixing

Individual and separate stock solutions are prepared—one containing lipid and the other siRNA. Lipid stock containing a desired lipid or lipid mixture, DSPC, cholesterol and aggregation-reducing lipid is prepared by solubilizing in 90% ethanol. The remaining 10% is low pH citrate buffer. The concentration of the lipid stock is 4 mg/mL. The pH of this citrate buffer can range between pH 3 and pH 5, depending on the type of lipid employed. The siRNA is also solubilized in citrate buffer at a concentration of 4 mg/mL. 5 mL of each stock solution was prepared.

Stock solutions are completely clear and lipids are checked to be certain of complete dissolution before combining with siRNA. Stock solutions may be heated to completely solubilize the lipids. The siRNAs used in the process may be unmodified oligonucleotides or modified and may be conjugated with lipophilic moieties such as cholesterol.

The individual stocks are combined by pumping each solution to a T-junction. A dual-head Watson-Marlow pump is used to simultaneously control the start and stop of the two streams. A 1.6 mm polypropylene tubing is further downsized to 0.8 mm tubing in order to increase the linear flow rate. The polypropylene line (ID=0.8 mm) are attached to either side of a T-junction. The polypropylene T has a linear edge of 1.6 mm for a resultant volume of 4.1 mm$^3$. Each of the large ends (1.6 mm) of polypropylene line is placed into test tubes containing either solubilized lipid stock or solubilized siRNA. After the T-junction, a single tubing is placed where the combined stream exited. The tubing is then extended into a container with 2× volume of PBS, which is rapidly stirred. The flow rate for the pump is at a setting of 300 rpm or 110 mL/min. Ethanol is removed and exchanged for PBS by dialysis. The lipid formulations are then concentrated using centrifugation or diafiltration to an appropriate working concentration.

C57BL/6 mice (Charles River Labs, MA) receive either saline or formulated siRNA via tail vein injection. At various time points after administration, serum samples are collected by retroorbital bleed. Serum levels of Factor VII protein are determined in samples using a chromogenic assay (Biophen FVII, Aniara Corporation, OH). To determine liver mRNA levels of Factor VII, animals are sacrificed and livers were harvested and snap frozen in liquid nitrogen. Tissue lysates are prepared from the frozen tissues and liver mRNA levels of Factor VII are quantified using a branched DNA assay (QuantiGene Assay, Panomics, CA).

FVII activity is evaluated in FVII siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

Example 9 siRNA Formulation Using Preformed Vesicles

Cationic lipid containing particles are made using the preformed vesicle method. Cationic lipid, DSPC, cholesterol and aggregation-reducing lipid were solubilized in ethanol at mole percentages of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. This generally requires 1-3 passes. For some cationic lipid mixtures which did not form small vesicles hydrating the lipid mixture with a lower pH buffer (50 mM citrate, pH 3) to protonate the phosphate group on the DSPC headgroup helps form stable 70-90 nm vesicles.

The FVII siRNA (solubilized in a 50 mM citrate, pH 4 aqueous solution containing 30% ethanol) is added to the vesicles, pre-equilibrated to 35° C., at a rate of ~5 mL/min with mixing. After a final target siRNA/lipid ratio of 0.06 (wt/wt) is achieved, the mixture is incubated for a further 30 min at 35° C. to allow vesicle re-organization and encapsulation of the FVII siRNA. The ethanol is then removed and the external buffer replaced with PBS (155 mM NaCl, 3 mM $Na_2HPO_4$, 1 mM $KH_2PO_4$, pH 7.5) by either dialysis or tangential flow diafiltration. The final encapsulated siRNA-to-lipid ratio is determined after removal of unencapsulated siRNA using size-exclusion spin columns or ion exchange spin columns.

Example 10

In Vivo Determination of Efficacy of Lipid Formulations

Test formulations are initially assessed for their FVII knockdown in female 7-9 week old, 15-25 g, female C57B1/6 mice at 0.1, 0.3, 1.0 and 5.0 mg/kg with 3 mice per treatment group. All studies included animals receiving either phosphate-buffered saline (PBS, Control group) or a benchmark formulation. Formulations are diluted to the appropriate concentration in PBS immediately prior to testing. Mice are weighed and the appropriate dosing volumes calculated (10 μL body weight). Test and benchmark formulations as well as PBS (for Control animals) are administered intravenously via the lateral tail vein. Animals are anesthetised 24 h later with an intraperitoneal injection of Ketamine/Xylazine and 500-700 μL of blood is collected by cardiac puncture into serum separator tubes (BD Microtainer). Blood is centrifuged at 2,000×g for 10 min at 15° C. and serum is collected and stored at −70° C. until analysis. Serum samples are thawed at 37° C. for 30 min, diluted in PBS and aliquoted into 96-well assay plates. Factor VII levels are assessed using a chromogenic assay (Biophen FVII kit, Hyphen BioMed) according to manufacturer's instructions and absorbance measured in microplate reader equipped with a 405 nm wavelength filter. Plasma FVII levels are quantified and $ED_{50}$ values (dose resulting in a 50% reduction in plasma FVII levels compared to control animals) calculated using a standard curve generated from a pooled sample of serum from Control animals. Those formulations of interest showing high levels of FVII knockdown ($ED_{50} \ll 0.1$ mg/kg) are re-tested in independent studies at a lower dose range to confirm potency and establish $ED_{50}$.

Example 11 siRNA Silencing in Subcutaneous Hep3B-luc Tumors in Mice

Silencing of luciferase was performed in subcutaneous Hep3B-luc tumors following intravenous administration of siRNA formulated in either PEG-C-DSMO or PEG-C-DSMA containing siRNA-lipid nanoparticles.

Tumors were established by implantation of $3 \times 10^6$ Hep3B-luc cells into the right flank of 6 week-old female C.B17/Icr-scid/scid Jcl mice. The cells were engineered to stably express firefly luciferase. Nineteen days after tumor implantation, cohorts of tumor-bearing mice received intravenous (tail vein) injections of a test article as follows:

| Group | Test article | Dose (siRNA) | n |
|---|---|---|---|
| 1 | PBS | — | 4 |
| 2 | L152 | 0.3 mg/kg | 4 |
| 3 | L153 | 0.3 mg/kg | 4 |
| 4 | L154 | 0.3 mg/kg | 4 |
| 5 | L155 | 0.3 mg/kg | 4 |
| 6 | L156 | 0.3 mg/kg | 4 |
| 7 | L157 | 0.3 mg/kg | 4 |
| 8 | L158 | 0.3 mg/kg | 4 |
| 9 | L159 | 0.3 mg/kg | 4 |

L152, L153, L154 and L155 are luciferase siRNA formulated by an in-line mixing method in lipid nanoparticles comprising PEG-C-DSMO (1.1 mol %, 1.4 mol %, 1.7 mol % and 2.0 mol %), MC3 (57.1 mol %), DPPC (7.1 mol %) and compensating cholesterol (33.8 mol %~34.7 mol %) at an N:P ratio of 3.2.

L156, L157, L158 and L159 are luciferase siRNA formulated by an in-line mixing method in lipid nanoparticles comprising PEG-C-DSMA (1.1 mol %, 1.4 mol %, 1.7 mol % and 2.0 mol %), MC3 (57.1 mol %), DPPC (7.1 mol %) and compensating cholesterol (33.8 mol %~34.7 mol %) at an N:P ratio of 3.2.

The sequences of luciferase siRNA are shown in the table below.

| Duplex | Sequence 5'-3' |
|---|---|
| Luc siRNA | [mC][mU][mU]A[mC]G[mC][mU]GAG[mU]A[mC][mU][mU][mC]GA[ts]tUCGAAGUACUCAGCGUAAG[ts]t |

[mN] is 2'OMe modification, t is deoxythymidine and s is phosphothioate

Forty-eight hours following treatment, mice were euthanized and tumors were collected for analysis. Total RNA was extracted followed by cDNA synthesis by random priming. Expression levels of luciferase normalized to human beta-actin was measured by TaqMan RT-PCR. The results are shown the FIGURE.

Sequences of TaqMan probe and primers for each gene are shown in the table below.

| Target | FAM-labeled probe sequence | Forward primer sequence Reverse primer sequence |
|---|---|---|
| Human beta-actin | ATCAAGATCATTGCTCCTCCTGAGCGC | CCTGGCACCCAGCACAAT GCCGATCCACACGGAGTACT |
| Luciferase | AAACAATCCGGAAGCGACCAACGC | AGGTCCTATGATTATGTCCGGTTATG GAATGTAGCCATCCATCCTTGTC |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various patents, patent applications, publications, product descriptions, and protocols are cited throughout this application, the disclosures of each of which are incorporated herein by reference in their entireties for all purposes.

What is claimed is:

1. A compound of formula (I):

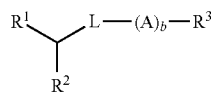

(I)

or a pharmaceutically acceptable salt thereof, wherein
$R^1$ and $R^2$ are each, independently, a $C_{10}$ to $C_{30}$ aliphatic group, wherein each aliphatic group is optionally substituted by one or more groups each independently selected from $R^a$;
L is -$L^1$-$Z^1$-($L^2$-$Z^2$)$_c$-$L^3$-;
$L^1$ is a bond, —(CR$^5$R$^{5'}$)$_i$—, or —(CR$^5$R$^{5'}$)$_i$—(C(R$^a$)═C(R$^b$))$_k$—(C≡C)$_k$—(CR$^a$R$^b$)$_j$—;
$Z^1$ is —O—, —S—, —N(R$^c$)—, —OC(O)—, —C(O)O—, —OC(O)O—, —N(R$^c$)C(O)O—, —N(R$^c$)C(O)N(R$^c$)—, —N(R$^c$)C(O)—, —C(O)N(R$^c$)—, —N═C(R$^a$)—, —C(R$^a$)═N—, —O—N═C(R$^a$)—, —O—N(R$^c$)—; heteroaryl, or heterocyclyl;
$L^2$ is —(CR$^a$R$^b$)$_p$— or —(CR$^a$R$^b$)$_j$—(C(R$^a$)═C(R$^b$))$_k$—(C≡C)$_k$—(CR$^a$R$^b$)$_j$—;
$Z^2$ is —O—, —S—, —N(R$^c$)—, —OC(O)—, —C(O)O—, —OC(O)O—, —OC(O)N(R$^c$)—, —N(R$^c$)C(O)O—, —N(R$^c$)C(O)—, —C(O)N(R$^c$)—, —N═C(R$^a$)—, —C(R$^a$)═N—, —O—N═C(R$^a$)—, —O—N(R$^c$)—, heteroaryl, or heterocyclyl;
$L^3$ is —(CR$^a$R$^b$)$_i$—;
each A, independently, is -$L^4$-, —NH-($L^4$)$_q$-(CR$^a$R$^b$)$_r$—C(O)—, or —C(O)—(CR$^a$R$^b$)$_r$-($L^4$)$_q$-NH—; wherein each q, independently, is 0, 1, 2, 3, or 4; and each r, independently, is 0, 1, 2, 3, or 4;
each $L^4$, independently, is —(CR$^a$R$^b$)$_s$O— or —O(CR$^a$R$^b$)$_s$—, wherein each s, independently, is 0, 1, 2, 3, or 4;
$R^3$ is H, —$R^c$, or —OR$^c$;
each occurrence of $R^5$ and $R^{5'}$ is, independently, H, halo, cyano, hydroxy, nitro, alkyl, alkenyl, alkynyl, or cycloalkyl;
each occurrence of $R^a$ and $R^b$ is, independently, H, halo, cyano, hydroxy, nitro, amino, alkylamino, dialkylamino, alkyl, alkenyl, alkynyl, cycloalkyl, alkoxy, aryl, heteroaryl, or heterocyclyl;
each $R^c$ is, independently, H, alkyl, acyl, cycloalkyl, alkenyl, alkynyl, aryl, heteroaryl, or heterocyclyl;
b ranges from 5 to about 500;
c is 0 or 1;
each i is, independently, 1, 2, 3, 4, 5, 6, 7, 8, or 9;
each occurrence of j and k, independently, is 0, 1, 2, or 3; and
p is an integer from 1 to 10.

2. The compound of claim 1, wherein $R^1$ and $R^2$ are independently $C_{10}$ to $C_{20}$ alkyl or $C_{10}$ to $C_{20}$ alkenyl.

3. The compound of claim 1, wherein $L^1$ is a bond or —(CR$^5$R$^{5'}$)$_i$—.

4. The compound of claim 1, wherein $Z^1$ is —O—, —N(H)—, —N(CH$_3$)—, —OC(O)—, —C(O)O—, —OC(O)N(CH$_3$)—, —N(H)C(O)O—, —N(CH$_3$)C(O)O—, —N(H)C(O)N(H)—, —N(H)C(O)N(CH$_3$)—, —N(CH$_3$)C(O)N(CH$_3$)—, —N(CH$_3$)C(O)N(H)—, —N(H)C(O)—, —N(CH$_3$)C(O)—, —C(O)N(H)—, —C(O)N(CH$_3$)—, —O—N═C(H)—, —O—N═C(CH$_3$)—, —O—N(H)—, —O—N(CH$_3$)— or heteroaryl.

5. The compound of claim 1, wherein $Z^1$ is —N(R$^c$)—, —N(R$^c$)C(O)O—, —N(R$^c$)C(O)N(R$^c$)—, —N(R$^c$)C(O)—, or —N═C(R$^a$)—, and the leftmost nitrogen atom in $Z^1$ is attached to the tertiary carbon atom of formula (I), or
$Z^1$ is a nitrogen-containing heteroaryl or heterocyclyl, wherein the nitrogen atom of the heteroaryl or heterocyclyl is bound to $L^1$ or if $L^1$ is a bond, then to the central tertiary carbon atom.

6. The compound of claim 1, wherein c is 1 and $L^2$ is —(CR$^a$R$^b$)$_p$—.

7. The compound of claim 1, wherein c is 1 and $Z^2$ is —O—, —C(O)O—, —C(O)N(R$^c$)—, or heteroaryl.

8. The compound of claim 1, wherein each A is, independently, $L^4$ and each $L^4$ is, independently —OCH$_2$CH$_2$—, —CH$_2$CH$_2$O—, —OCH$_2$CH$_2$CH$_2$—, —OCH(CH$_3$)CH$_2$CH$_2$—, —OCH$_2$CH$_2$—CH(CH$_3$)—, —OCH(CH$_3$)CH$_2$— or —OCH$_2$CH(CH$_3$)—.

9. The compound of claim 1, wherein $R^3$ is alkoxy.

10. The compound of claim 9, wherein $R^3$ is methoxy.

11. The compound of claim 1, wherein b is from about 30 to about 60.

12. The compound of claim 1, wherein c is 0.

13. The compound of claim 1, wherein c is 1.

14. The compound of claim 1, wherein
$R^1$ and $R^2$ are each, independently $C_{12}$ to $C_{20}$ alkyl or $C_{12}$ to $C_{20}$ alkenyl;
L is -$L^1$-$Z^1$-$L^3$- or -$L^1$-$Z^1$-($L^2$-$Z^2$)-$L^3$-;
$L^1$ is a bond or —(CR$^5$R$^{5'}$)$_i$—;
$Z^1$ is —O—, —N(R$^c$)—, —OC(O)—, —C(O)O—, —N(R$^c$)C(O)O—, —N(R$^c$)C(O)N(R$^c$)—, —N(R$^c$)C(O)—, —C(O)N(R$^c$)—, —O—N═C(R$^a$)—, —O—N(R$^c$)—, heteroaryl, or heterocyclyl;
$L^2$ is —(CR$^a$R$^b$)$_p$;
$Z^2$ is —O—, —C(O)O—, —C(O)N(R$^c$)—, or heteroaryl;
$L^3$ is —(CR$^a$R$^b$)$_i$—;
each A is, independently, -$L^4$-;
each $L^4$ is, independently, —OCH$_2$CH$_2$—, —CH$_2$CH$_2$O—, —OCH(CH$_3$)CH$_2$ or —OCH$_2$CH(CH$_3$)—;
$R^3$ is —OR$^c$;
each occurrence of $R^a$ is, independently, H or alkyl;
each occurrence of $R^b$ is, independently, H or alkyl; and
$R^c$ is H or alkyl.

15. The compound of claim 1, wherein
$R^1$ and $R^2$ are each, independently $C_{12}$ to $C_{20}$ alkyl or $C_{12}$ to $C_{20}$ alkenyl; and
$Z^1$ is —N(R$^c$)—, —N(R$^c$)C(O)O—, —N(R$^c$)C(O)N(R$^c$)—, —N(R$^c$)C(O)—, or —N═C(R$^a$)—, wherein the leftmost nitrogen atom in $Z^1$ is bound to $L^1$ or if $L^1$ is a bond, then to the central tertiary carbon atom of formula (I)), or
$Z^1$ is a nitrogen-containing heteroaryl or heterocyclyl, wherein the nitrogen atom of the heteroaryl or heterocyclyl is bound to $L^1$ or if $L^1$ is a bond, then to the central tertiary carbon atom of formula (I).

16. A compound of formula (II):

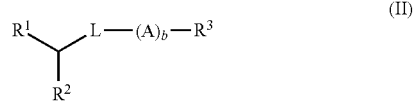

(II)

or a pharmaceutically acceptable salt thereof, wherein
$R^1$ and $R^2$ are each, independently, $C_{10}$ to $C_{30}$ aliphatic group;

L is -L¹-Z¹-L³-;
L¹ is a bond or —(CR⁵R⁵')ᵢ—;
Z¹ is —N(Rᶜ)—, —N(Rᶜ)C(O)O—, —N(Rᶜ)C(O)N(Rᶜ)—, —N(Rᶜ)C(O)—, or —N═C(Rᵃ)—, wherein the leftmost nitrogen atom in Z¹ is bound to L¹ or if L¹ is a bond, then to the central tertiary carbon atom of formula (II)), or Z¹ is a nitrogen-containing heteroaryl or heterocyclyl, wherein the nitrogen atom of the heteroaryl or heterocyclyl is bound to L¹ or if L¹ is a bond, then to the central tertiary carbon atom of formula (II));

L³ is —(CRᵃRᵇ)ᵢ—;
each A is, independently, -L⁴-;
b ranges from about 5 to about 500;
each L⁴, independently, is —OCH₂CH₂—, —CH₂CH₂O—, —OCH(CH₃)CH₂— or —OCH₂CH(CH₃)—;
R³ is —ORᶜ;
each occurrence of Rᵃ, Rᶜ, R⁵ and R⁵' is, independently, H or alkyl; and
i is 2, 3, 4 or 5.

17. A compound of formula (III):

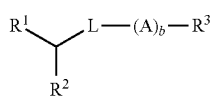

or a pharmaceutically acceptable salt thereof, wherein
R¹ and R² are each, independently C₁₂ to C₂₀ alkyl or C₁₂ to C₂₀ alkenyl;
L is -L¹-Z¹-L²-Z²-L³-;
L¹ is a bond or —(CR⁵R⁵')ᵢ—;
Z¹ is —N(Rᶜ)—, —N(Rᶜ)C(O)O—, —N(Rᶜ)C(O)N(Rᶜ)—, —N(Rᶜ)C(O)—, or —N═C(Rᵃ)—, wherein the leftmost nitrogen atom in Z¹ is bound to L¹ or if L¹ is a bond, then to the central tertiary carbon atom of formula (II)), or Z¹ is a nitrogen-containing heteroaryl or heterocyclyl, wherein the nitrogen atom of the heteroaryl or heterocyclyl is bound to L¹ or if L¹ is a bond, then to the central tertiary carbon atom of formula (II));

L² is —(CRᵃRᵇ)ₚ—;
Z² is —O—, —C(O)O—, —C(O)N(Rᶜ)—, or heteroaryl;
L³ is —(CRᵃRᵇ)ᵢ—;
each A is, independently, -L⁴-;
b ranges from about 5 to about 500;
each L⁴, independently, is —OCH₂CH₂—, —CH₂CH₂O—, —OCH(CH₃)CH₂— or —OCH₂CH(CH₃)—;
R³ is —ORᶜ;
each occurrence of Rᵃ, Rᵇ, Rᶜ, R⁵ and R⁵' is, independently, H or alkyl;
i is 2, 3, 4 or 5; and
p is 1 to 10.

18. The compound selected from:

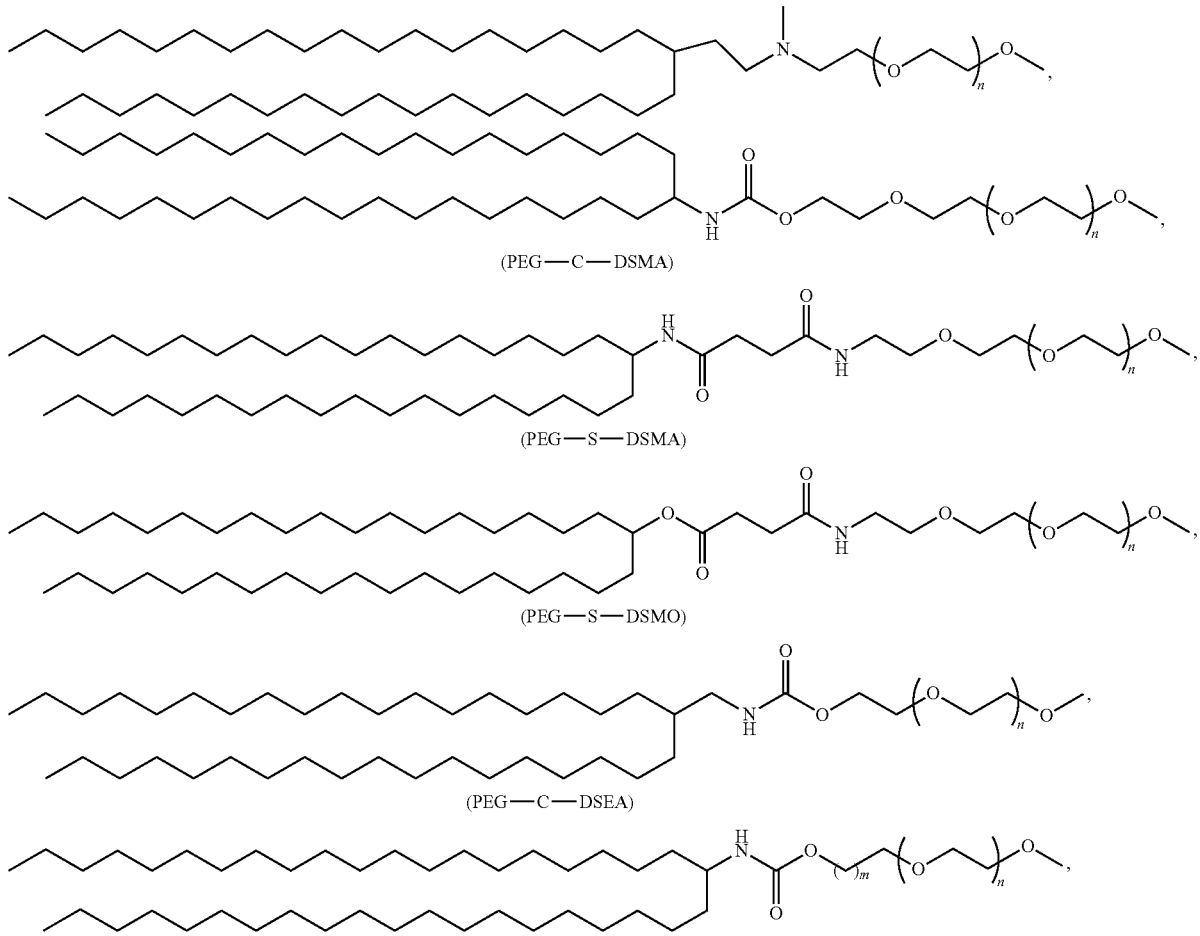

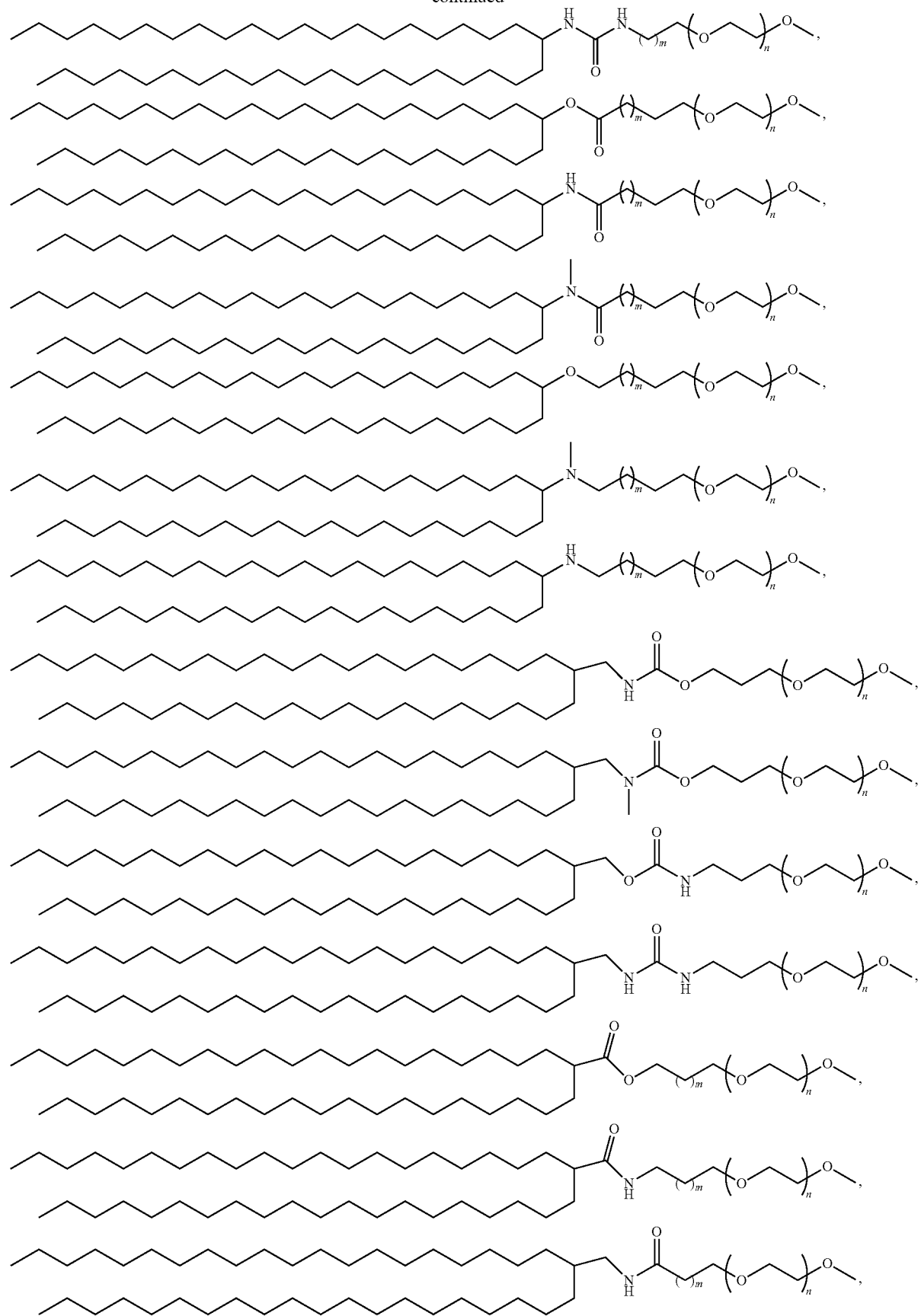

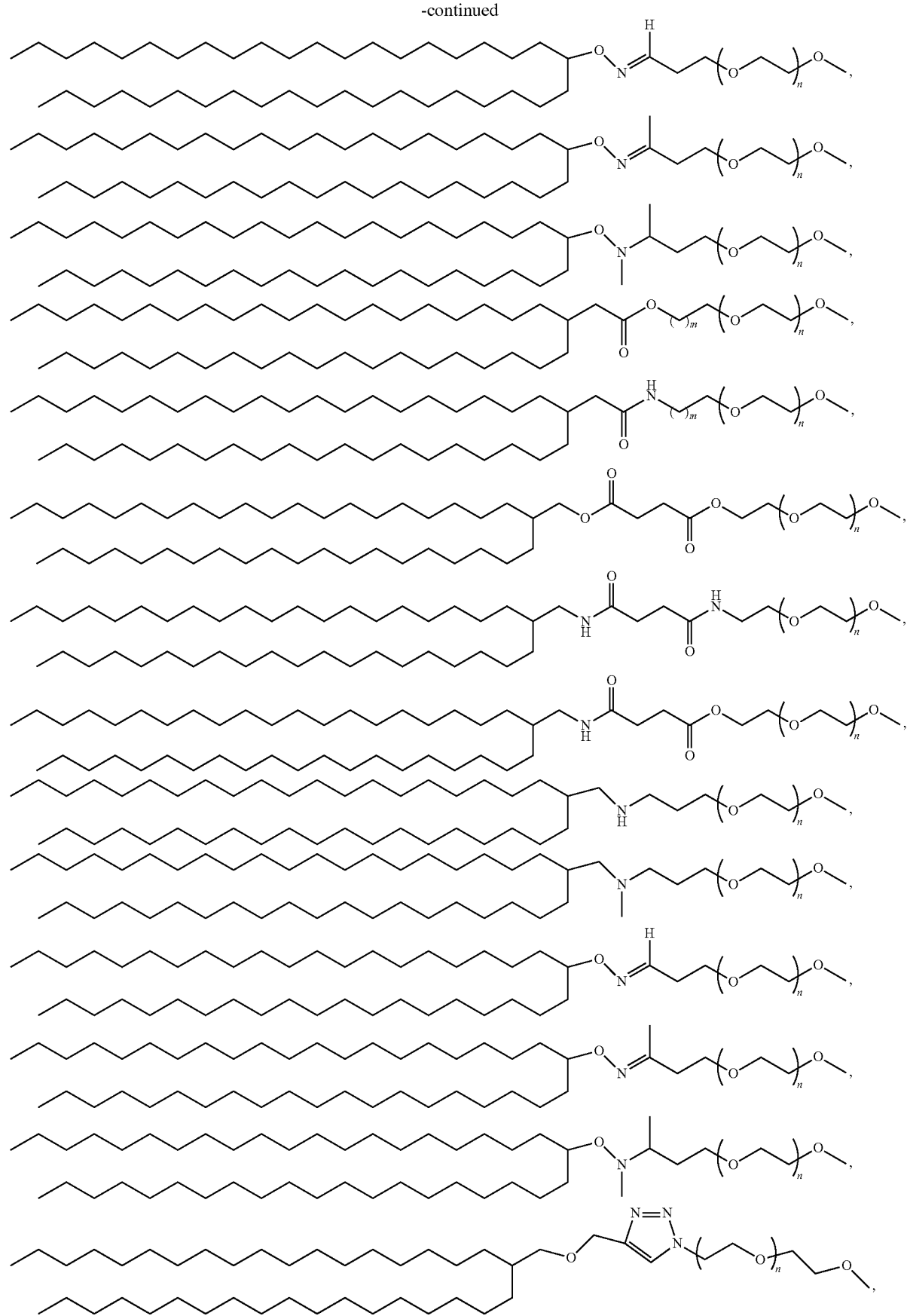

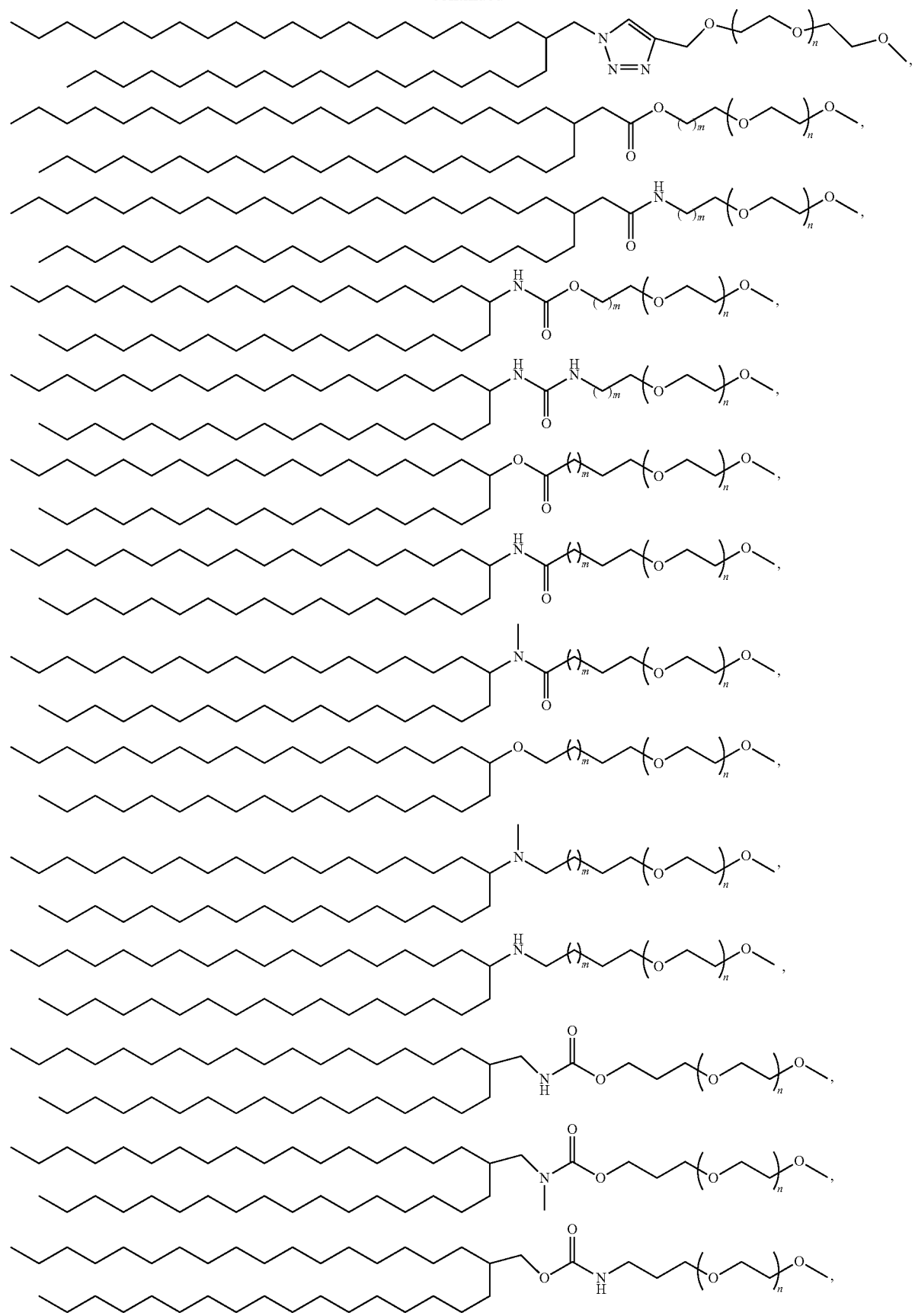

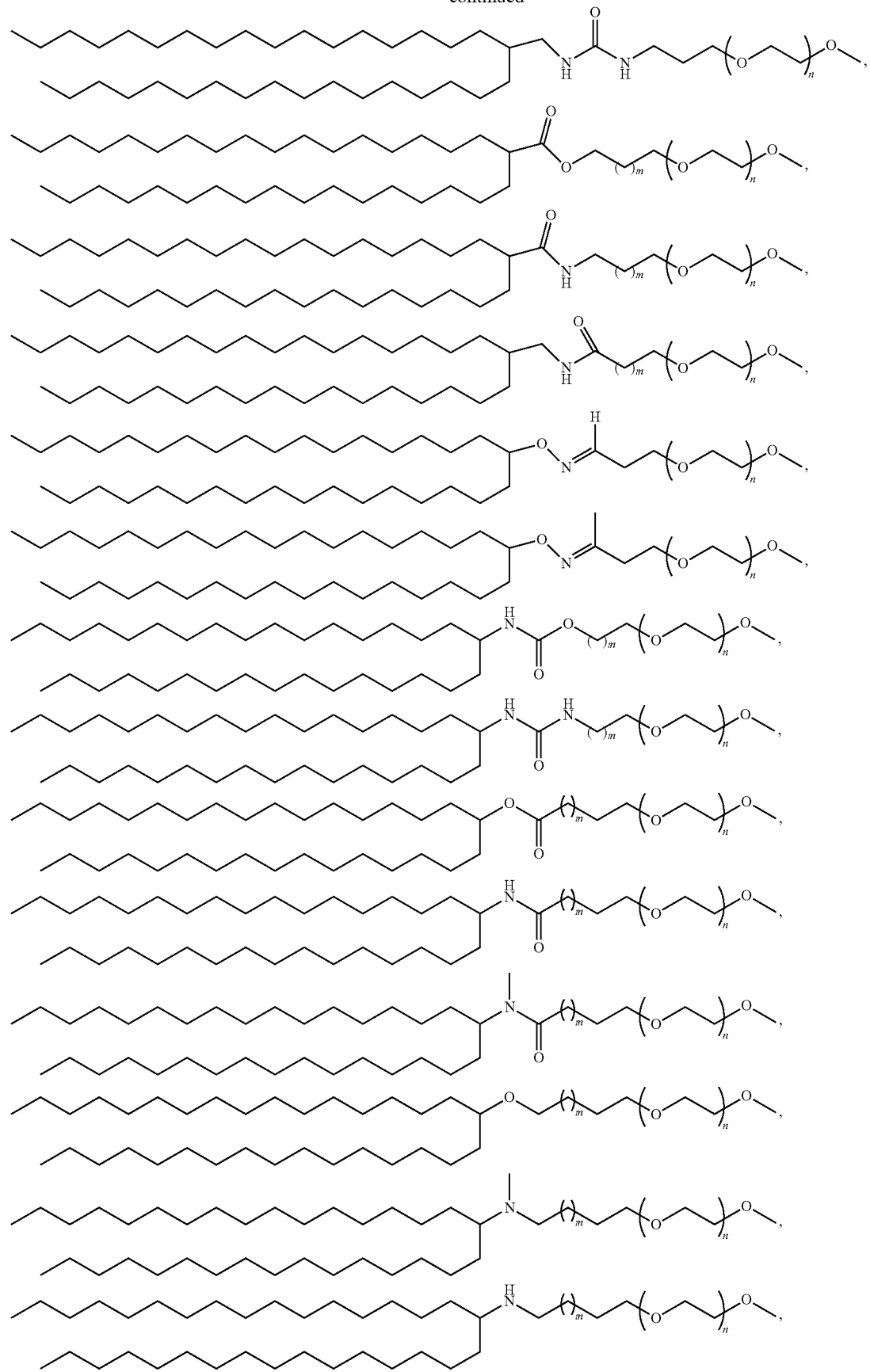

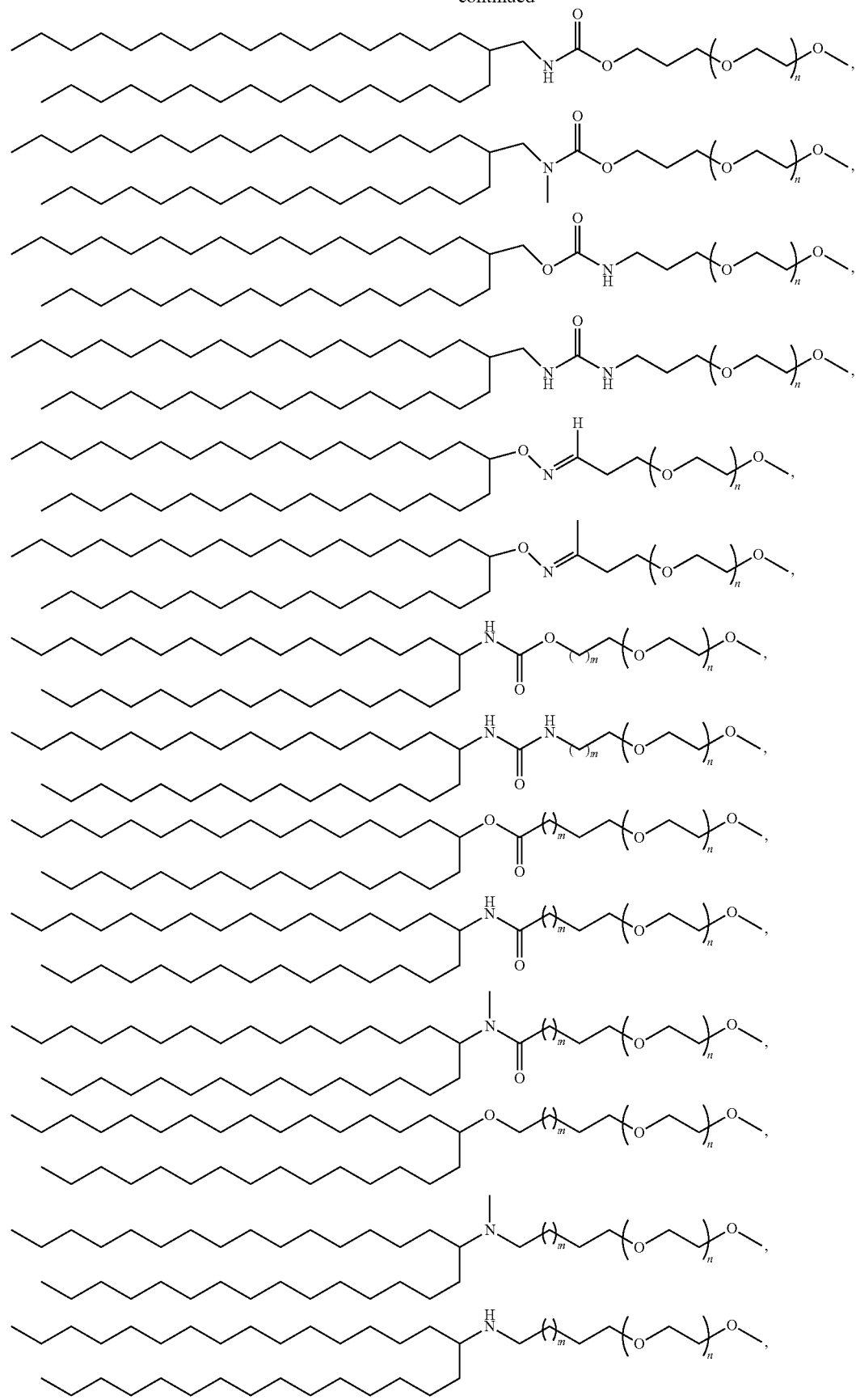

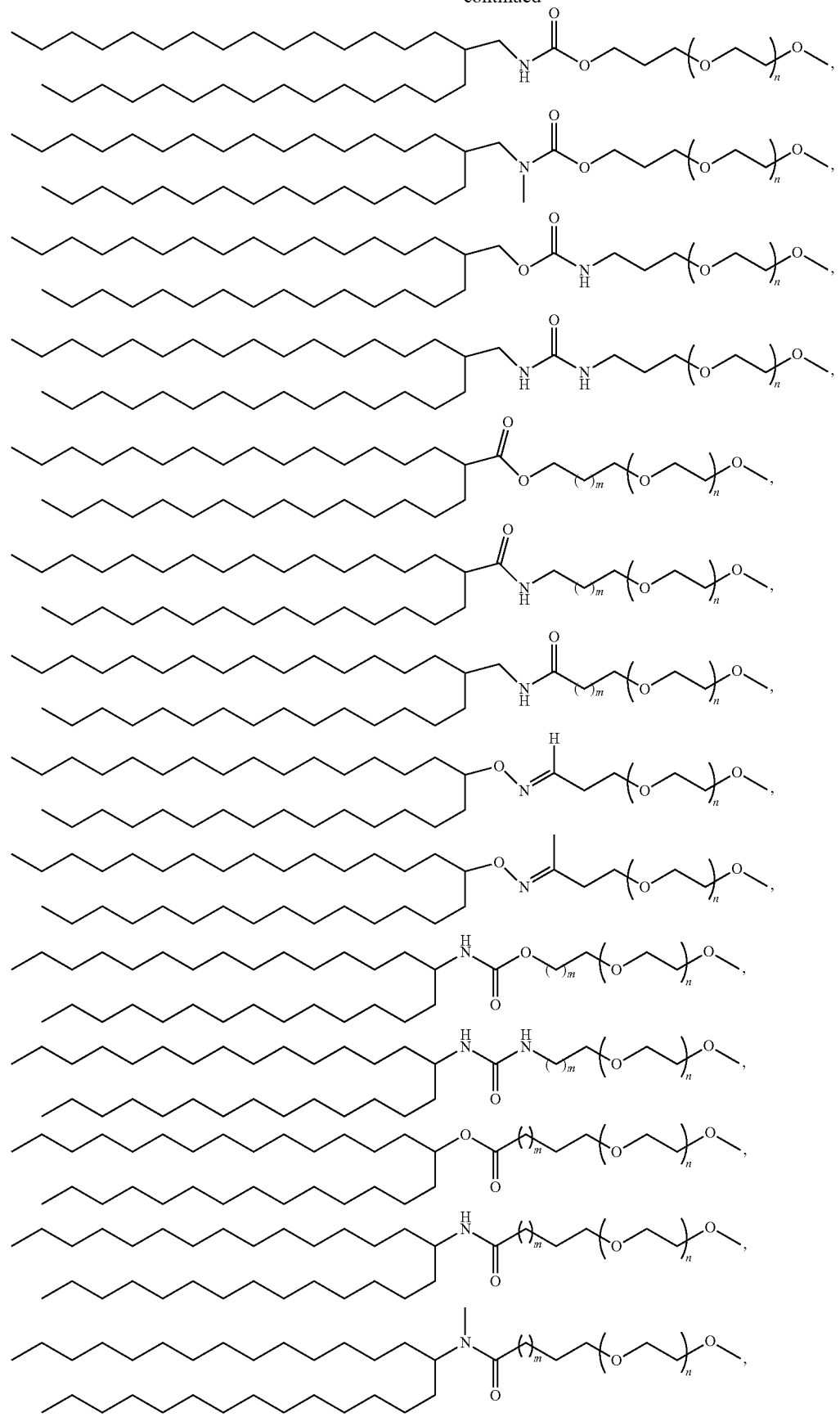

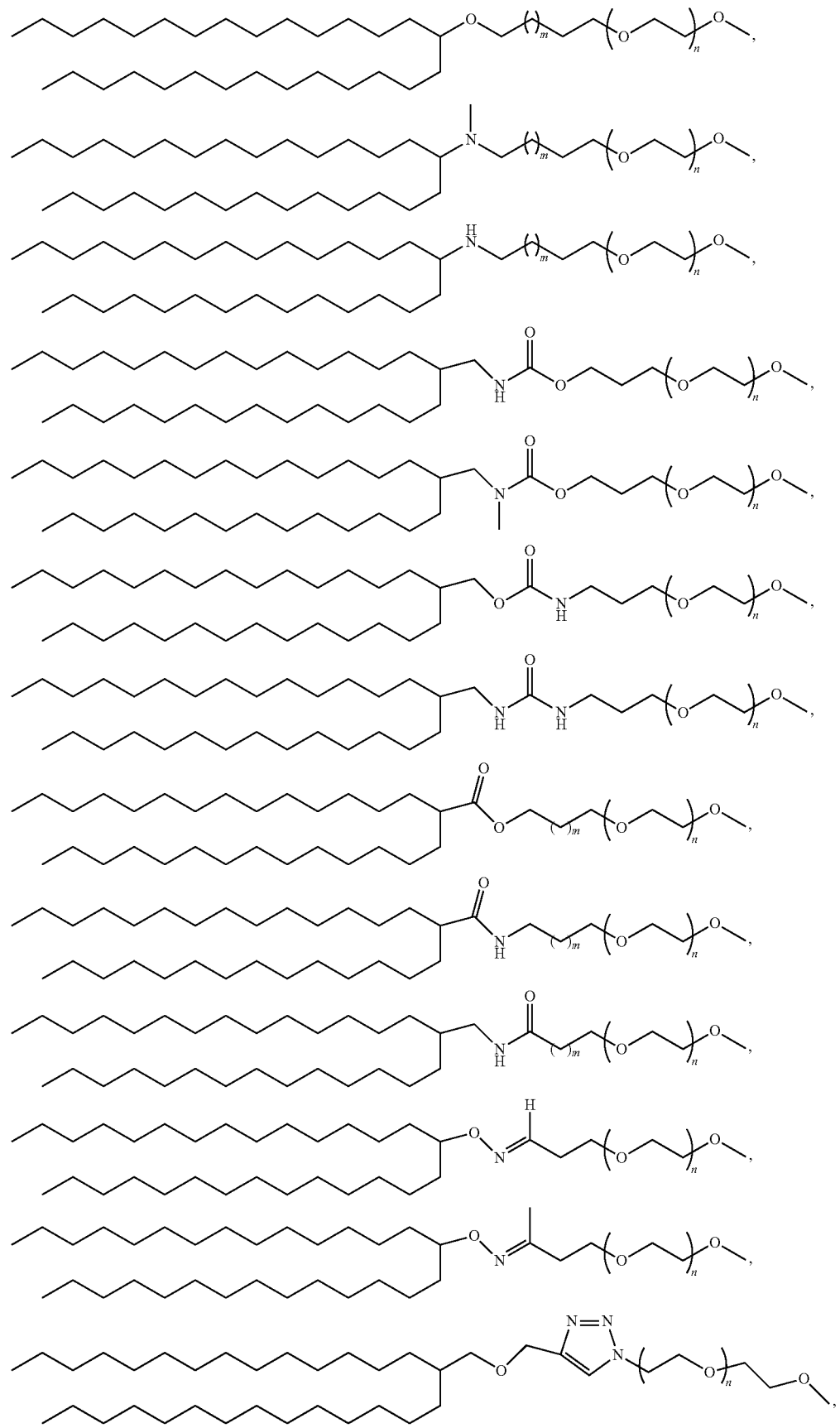

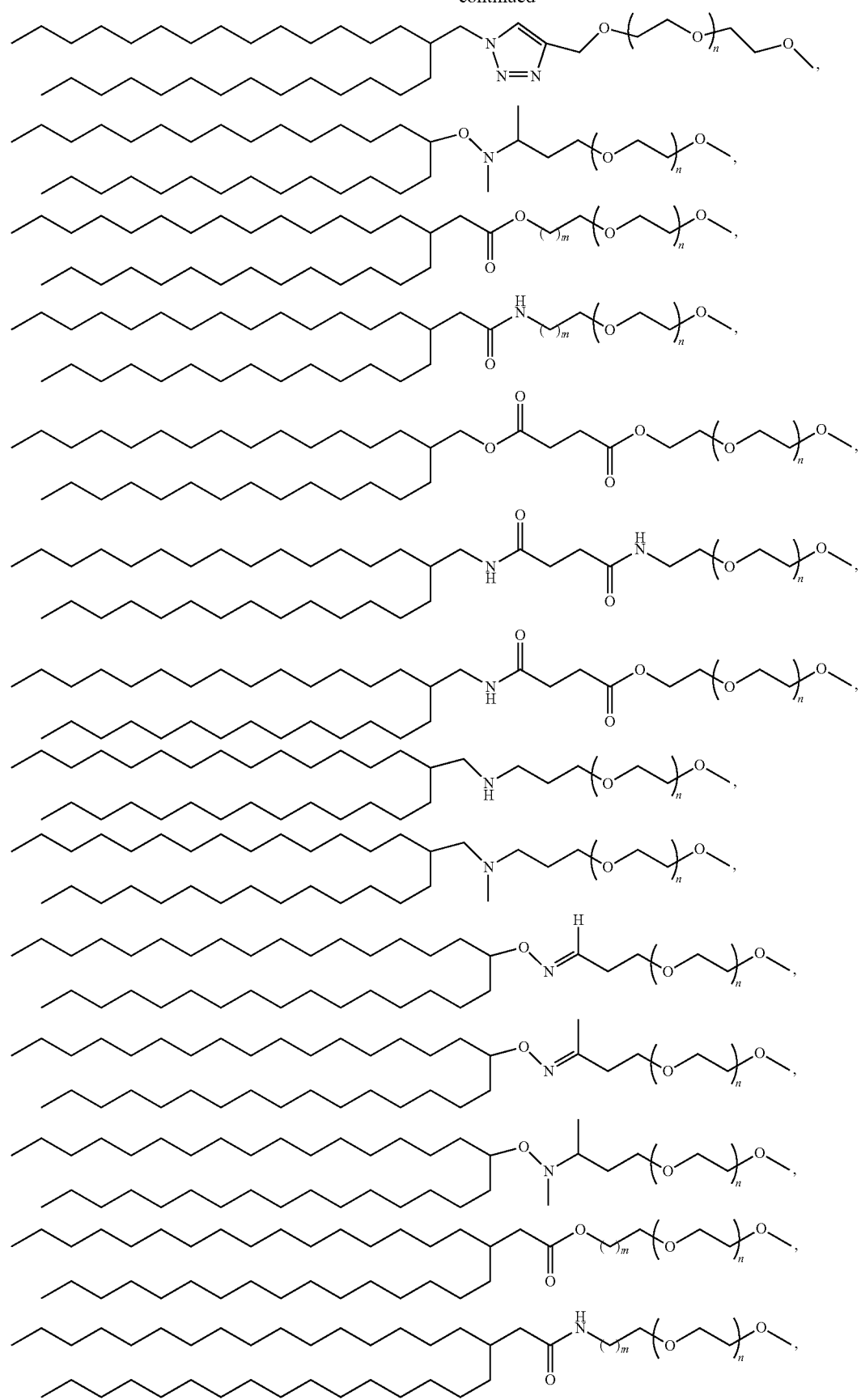

-continued
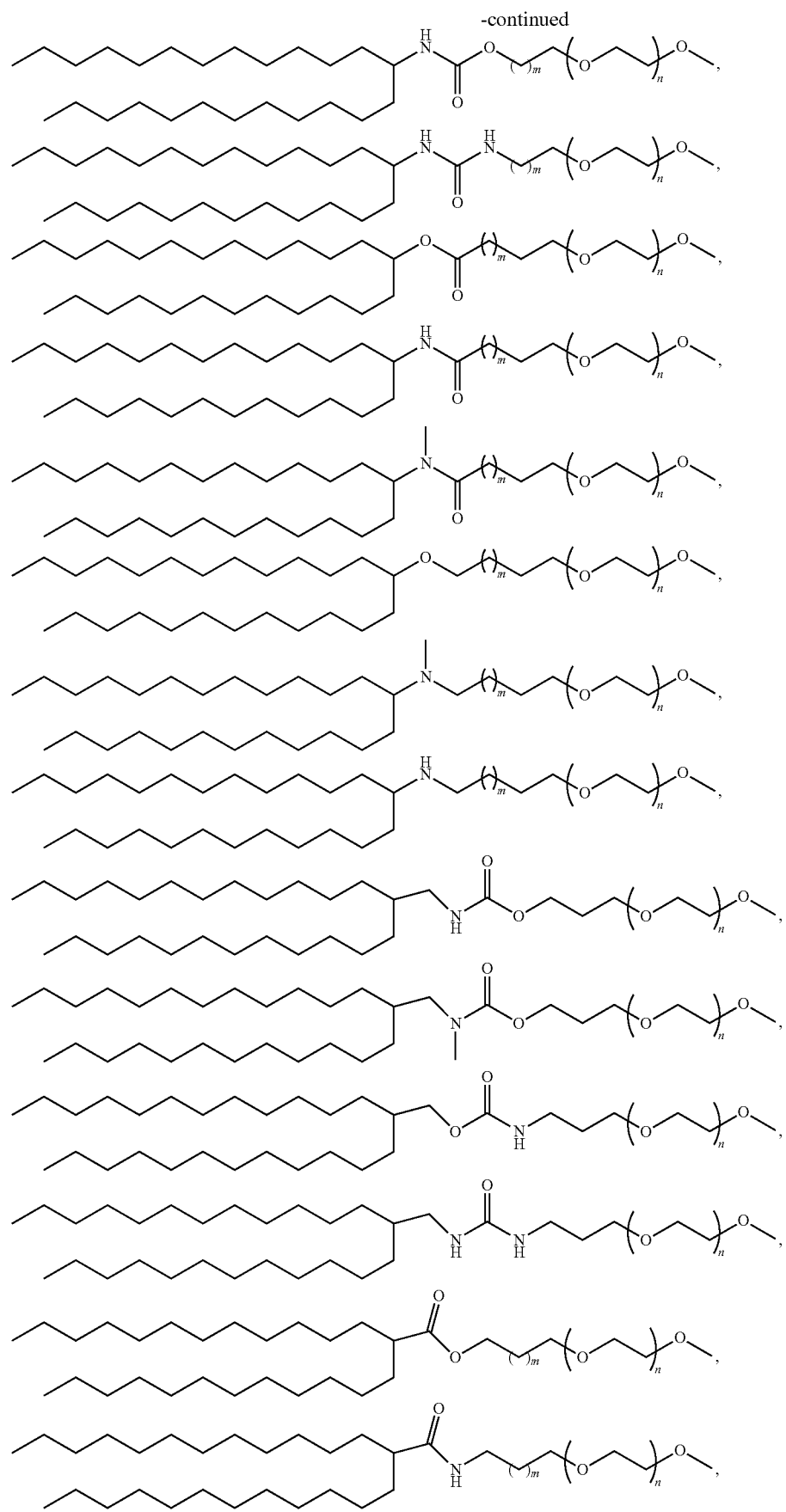

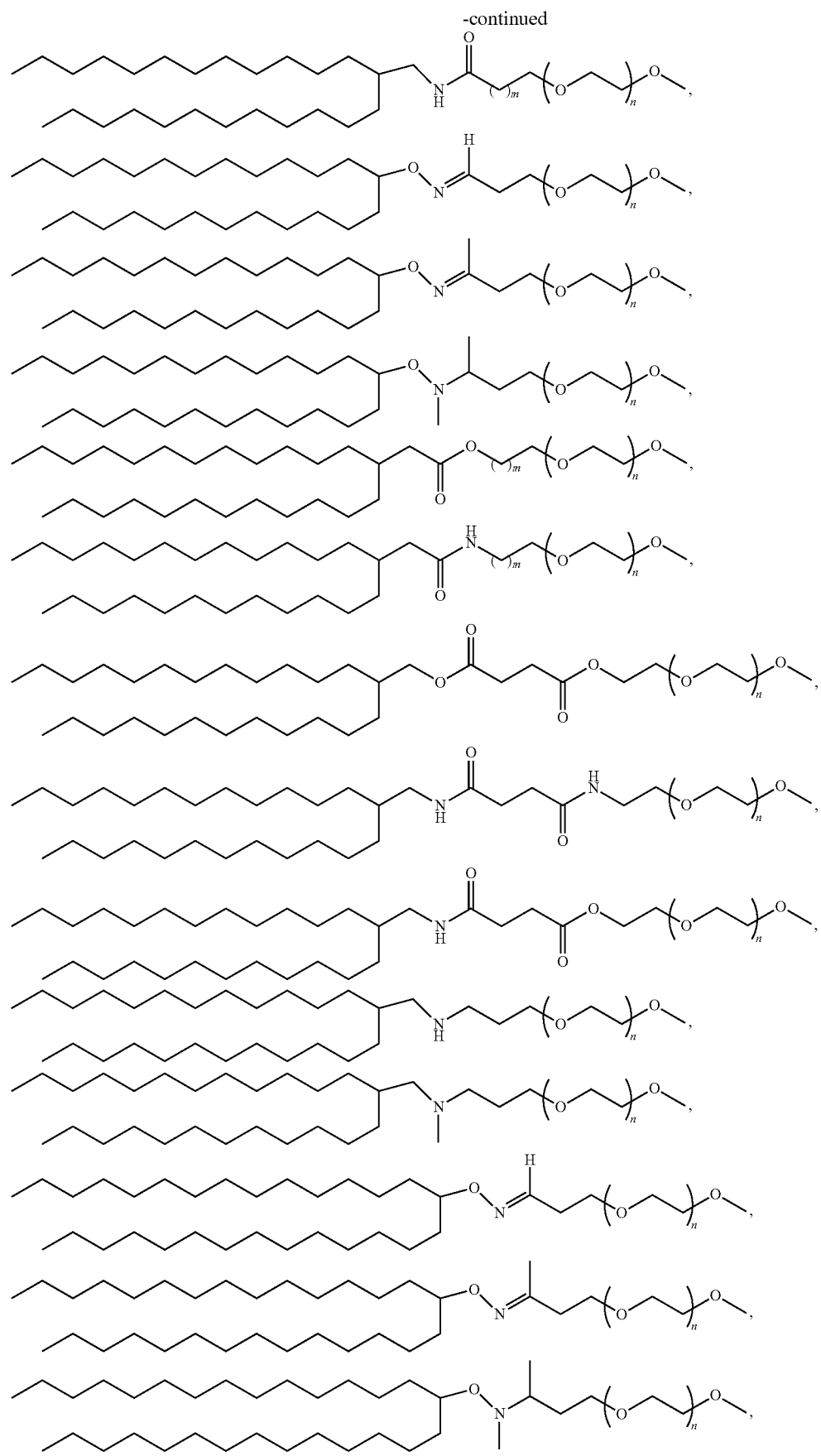

-continued

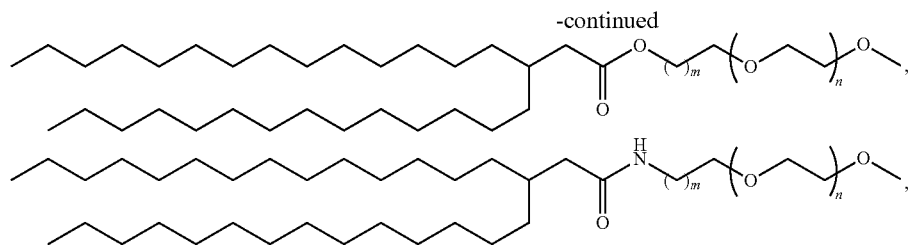

or a pharmaceutically acceptable salt thereof, wherein
n is an integer from 1 to 1,000; and
m is 0, 1, 2, 3, 4, 5, or 6.

19. The compound of claim 18, wherein n is from about 30 to about 60.

20. A lipid particle comprising a compound of formula (I) claim 1, a cationic lipid, a neutral lipid, and a sterol.

21. The lipid particle of claim 20, wherein the cationic lipid is present in a mole percentage of about 20% and about 60%; the neutral lipid is present in a mole percentage of about 5% to about 25%; the sterol is present in a mole percentage of about 25% to about 55%; and the compound according to formula (I) is present in a mole percentage of about 0.5% to about 15%.

22. The lipid particle of claim 20, further comprising an active agent selected from a plasmid, an immunostimulatory oligonucleotide, an siRNA, an antisense oligonucleotide, a microRNA, an antagomir, an aptamer, and a ribozyme.

23. A pharmaceutical composition comprising a lipid particle of claim 20 and a pharmaceutically acceptable carrier.

24. A method of modulating the expression of a target gene in a cell comprising providing a lipid particle of claim 22 to the cell.

25. The compound of claim 1, wherein b ranges from about 10 to about 500.

26. The compound of claim 1, wherein b ranges from about 10 to about 250.

27. The compound of claim 1, wherein b ranges from about 25 to about 100.

28. The compound of claim 1, wherein b ranges from about 40 to about 50.

29. The compound of claim 16, wherein b ranges from about 10 to about 500.

30. The compound of claim 16, wherein b ranges from about 10 to about 250.

31. The compound of claim 16, wherein b ranges from about 25 to about 100.

32. The compound of claim 16, wherein b ranges from about 30 to about 60.

33. The compound of claim 16, wherein b ranges from about 40 to about 50.

34. The compound of claim 17, wherein b ranges from about 10 to about 500.

35. The compound of claim 17, wherein b ranges from about 10 to about 250.

36. The compound of claim 17, wherein b ranges from about 25 to about 100.

37. The compound of claim 17, wherein b ranges from about 30 to about 60.

38. The compound of claim 17, wherein b ranges from about 40 to about 50.

39. The compound of claim 1, wherein $R^3$ is —$R^c$, or —$OR^c$, and $R^c$ is alkyl, acyl, cycloalkyl, alkenyl, alkynyl, aryl, heteroaryl, or heterocyclyl.

40. The compound of claim 1, wherein $Z^1$ is —S—, —N($R^c$)—, —OC(O)—, —C(O)O—, —OC(O)O—, —N($R^c$)C(O)O—, —N($R^c$)C(O)N($R^c$)—, —N($R^c$)C(O)—, —C(O)N($R^c$)—, —N=C($R^a$)—, —C($R^a$)=N—, —O—N=C($R^a$)—, —O—N($R^c$)—; heteroaryl, or heterocyclyl.

* * * * *

```
SEQUENCE LISTING

<160> NUMBER OF SEQ ID NOS: 66

<210> SEQ ID NO 1
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
taacgttgag gggcat                                                       16

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ttccatgacg ttcctgacgt                                                   20

<210> SEQ ID NO 3
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
tccatgacgt tcctgacgt                                                    19

<210> SEQ ID NO 4
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(4)
<223> OTHER INFORMATION: methylated cytosine

<400> SEQUENCE: 4
taacgttgag gggcat                                                       16

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 5
tccatgacgt tcctgacgtt                                              20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: methylated cytosine
<220> FEATURE:
<221> NAME/KEY: modified_base
<222> LOCATION: (17)..(17)
<223> OTHER INFORMATION: methylated cytosine

<400> SEQUENCE: 6
tccatgacgt tcctgacgtt                                              20

<210> SEQ ID NO 7
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
taagcatacg gggtgt                                                  16

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gatgctgtgt cggggtctcc gggc                                         24

<210> SEQ ID NO 9
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tcgtcgtttt gtcgttttgt cgtt                                         24

<210> SEQ ID NO 10
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: modified_base
<222> LOCATION: (2)..(2)
<223> OTHER INFORMATION: methylated cytosine
<220> FEATURE:
<221> NAME/KEY: modified_base
<222> LOCATION: (5)..(5)
<223> OTHER INFORMATION: methylated cytosine
<220> FEATURE:
<221> NAME/KEY: modified_base
<222> LOCATION: (13)..(13)
<223> OTHER INFORMATION: methylated cytosine
<220> FEATURE:
<221> NAME/KEY: modified_base
<222> LOCATION: (21)..(21)
<223> OTHER INFORMATION: methylated cytosine

<400> SEQUENCE: 10
tcgtcgtttt gtcgttttgt cgtt                                          24

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
tccaggactt ctctcaggtt                                               20

<210> SEQ ID NO 12
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
tctcccagcg tgcgccat                                                 18

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
tgcatccccc aggccaccat                                               20

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gcccaagctg gcatccgtca                                               20
```

```
<210> SEQ ID NO 15
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ggtgctcact gcggc                                                    15

<210> SEQ ID NO 16
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
aaccgttgag gggcat                                                   16

<210> SEQ ID NO 17
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
tatgctgtgc cggggtcttc gggc                                          24

<210> SEQ ID NO 18
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
gtgccggggt cttcgggc                                                 18

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ggaccctcct ccggagcc                                                 18

<210> SEQ ID NO 20
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 20
tcctccggag ccagactt                                                 18

<210> SEQ ID NO 21
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
aacgttgagg ggcat                                                    15

<210> SEQ ID NO 22
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ccgtggtcat gctcc                                                    15

<210> SEQ ID NO 23
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
cagcctggct caccgccttg g                                             21

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
cagccatggt tcccccaac                                                20

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gttctcgctg gtgagtttca                                               20

<210> SEQ ID NO 26
<211> LENGTH: 15
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 26
gtgctccatt gatgc                                                           15

<210> SEQ ID NO 27
<211> LENGTH: 33
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
gaguucugau gaggccgaaa ggccgaaagu cug                                        33

<210> SEQ ID NO 28
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
caacgttatg gggaga                                                          16

<210> SEQ ID NO 29
<211> LENGTH: 29
<212> TYPE: PRT
<213> ORGANISM: Unknown
<220> FEATURE:
<221> NAME/KEY: source
<223> OTHER INFORMATION: /note="Description of Unknown: GALA
      peptide"

<400> SEQUENCE: 29

Ala Ala Leu Glu Ala Leu Ala Glu Ala Leu Glu Ala Leu Glu Ala
1               5                   10                  15

Leu Glu Ala Leu Ala Glu Ala Ala Ala Gly Gly Cys
                20                  25

<210> SEQ ID NO 30
<211> LENGTH: 45
<212> TYPE: PRT
<213> ORGANISM: Unknown
<220> FEATURE:
<221> NAME/KEY: source
<223> OTHER INFORMATION: /note="Description of Unknown: EALA
      polypeptide"

<400> SEQUENCE: 30

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys Ala Leu
                20                  25                  30

Glu Ala Leu Ala Glu Ala Leu Glu Ala Leu Ala Glu Ala
            35                  40                  45
```

```
<210> SEQ ID NO 31
<211> LENGTH: 22
<212> TYPE: PRT
<213> ORGANISM: Unknown
<220> FEATURE:
<221> NAME/KEY: source
<223> OTHER INFORMATION: /note="Description of Unknown: INF-7
      peptide"

<400> SEQUENCE: 31

Gly Leu Phe Glu Ala Ile Glu Gly Phe Ile Glu Asn Gly Trp Glu Gly
1               5                   10                  15

Met Ile Trp Asp Tyr Gly
            20

<210> SEQ ID NO 32
<211> LENGTH: 23
<212> TYPE: PRT
<213> ORGANISM: Unknown
<220> FEATURE:
<221> NAME/KEY: source
<223> OTHER INFORMATION: /note="Description of Unknown: Inf HA-2
      peptide"

<400> SEQUENCE: 32

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 33
<211> LENGTH: 24
<212> TYPE: PRT
<213> ORGANISM: Unknown
<220> FEATURE:
<221> NAME/KEY: source
<223> OTHER INFORMATION: /note="Description of Unknown: diINF-7
      peptide"

<400> SEQUENCE: 33

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 34
<211> LENGTH: 22
<212> TYPE: PRT
<213> ORGANISM: Unknown
<220> FEATURE:
<221> NAME/KEY: source
<223> OTHER INFORMATION: /note="Description of Unknown: diINF3
      peptide"

<400> SEQUENCE: 34

Gly Leu Phe Glu Ala Ile Glu Gly Phe Ile Glu Asn Gly Trp Glu Gly
1               5                   10                  15

Met Ile Asp Gly Gly Cys
            20

<210> SEQ ID NO 35
<211> LENGTH: 35
<212> TYPE: PRT
<213> ORGANISM: Unknown
```

```
<220> FEATURE:
<221> NAME/KEY: source
<223> OTHER INFORMATION: /note="Description of Unknown: GLF
      polypeptide"

<400> SEQUENCE: 35

Gly Leu Phe Gly Ala Leu Ala Glu Ala Leu Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 36
<211> LENGTH: 34
<212> TYPE: PRT
<213> ORGANISM: Unknown
<220> FEATURE:
<221> NAME/KEY: source
<223> OTHER INFORMATION: /note="Description of Unknown: GALA-INF3
      polypeptide"

<400> SEQUENCE: 36

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

<210> SEQ ID NO 37
<211> LENGTH: 21
<212> TYPE: PRT
<213> ORGANISM: Unknown
<220> FEATURE:
<221> NAME/KEY: source
<223> OTHER INFORMATION: /note="Description of Unknown: INF-5
      peptide"
<220> FEATURE:
<221> NAME/KEY: MOD_RES
<222> LOCATION: (17)..(17)
<223> OTHER INFORMATION: Norleucine

<400> SEQUENCE: 37

Gly Leu Phe Glu Ala Ile Glu Gly Phe Ile Glu Asn Gly Trp Glu Gly
1               5                   10                  15

Xaa Ile Asp Gly Lys
        20

<210> SEQ ID NO 38
<211> LENGTH: 20
<212> TYPE: PRT
<213> ORGANISM: Unknown
<220> FEATURE:
<221> NAME/KEY: source
<223> OTHER INFORMATION: /note="Description of Unknown: INF-5
      peptide"
<220> FEATURE:
<221> NAME/KEY: MOD_RES
<222> LOCATION: (17)..(17)
<223> OTHER INFORMATION: Norleucine

<400> SEQUENCE: 38

Gly Leu Phe Glu Ala Ile Glu Gly Phe Ile Glu Asn Gly Trp Glu Gly
1               5                   10                  15

Xaa Ile Asp Gly
        20
```

-continued

```
<210> SEQ ID NO 39
<211> LENGTH: 16
<212> TYPE: PRT
<213> ORGANISM: Unknown
<220> FEATURE:
<221> NAME/KEY: source
<223> OTHER INFORMATION: /note="Description of Unknown: Penetratin
      peptide"

<400> SEQUENCE: 39

Arg Gln Ile Lys Ile Trp Phe Gln Asn Arg Arg Met Lys Trp Lys Lys
1               5                   10                  15

<210> SEQ ID NO 40
<211> LENGTH: 13
<212> TYPE: PRT
<213> ORGANISM: Human immunodeficiency virus

<400> SEQUENCE: 40

Gly Arg Lys Lys Arg Arg Gln Arg Arg Arg Pro Pro Gln
1               5                   10

<210> SEQ ID NO 41
<211> LENGTH: 27
<212> TYPE: PRT
<213> ORGANISM: Unknown
<220> FEATURE:
<221> NAME/KEY: source
<223> OTHER INFORMATION: /note="Description of Unknown: signal
      sequence-based peptide"

<400> SEQUENCE: 41

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 42
<211> LENGTH: 18
<212> TYPE: PRT
<213> ORGANISM: Unknown
<220> FEATURE:
<221> NAME/KEY: source
<223> OTHER INFORMATION: /note="Description of Unknown: PVEC
      peptide"

<400> SEQUENCE: 42

Leu Leu Ile Ile Leu Arg Arg Arg Ile Arg Lys Gln Ala His Ala His
1               5                   10                  15

Ser Lys

<210> SEQ ID NO 43
<211> LENGTH: 26
<212> TYPE: PRT
<213> ORGANISM: Unknown
<220> FEATURE:
<221> NAME/KEY: source
<223> OTHER INFORMATION: /note="Description of Unknown: Transportan
      peptide"

<400> SEQUENCE: 43

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25
```

```
<210> SEQ ID NO 44
<211> LENGTH: 18
<212> TYPE: PRT
<213> ORGANISM: Unknown
<220> FEATURE:
<221> NAME/KEY: source
<223> OTHER INFORMATION: /note="Description of Unknown: Amphiphilic
      model peptide"

<400> SEQUENCE: 44

Lys Leu Ala Leu Lys Leu Ala Leu Lys Ala Leu Lys Ala Ala Leu Lys
1               5                   10                  15

Leu Ala

<210> SEQ ID NO 45
<211> LENGTH: 9
<212> TYPE: PRT
<213> ORGANISM: Unknown
<220> FEATURE:
<221> NAME/KEY: source
<223> OTHER INFORMATION: /note="Description of Unknown: 'Arg9' motif
      peptide"

<400> SEQUENCE: 45

Arg Arg Arg Arg Arg Arg Arg Arg Arg
1               5

<210> SEQ ID NO 46
<211> LENGTH: 10
<212> TYPE: PRT
<213> ORGANISM: Unknown
<220> FEATURE:
<221> NAME/KEY: source
<223> OTHER INFORMATION: /note="Description of Unknown: Bacterial cell
      wall permeating peptide"

<400> SEQUENCE: 46

Lys Phe Phe Lys Phe Phe Lys Phe Phe Lys
1               5                   10

<210> SEQ ID NO 47
<211> LENGTH: 37
<212> TYPE: PRT
<213> ORGANISM: Unknown
<220> FEATURE:
<221> NAME/KEY: source
<223> OTHER INFORMATION: /note="Description of Unknown: LL-37
      polypeptide"

<400> SEQUENCE: 47

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
        35

<210> SEQ ID NO 48
<211> LENGTH: 31
<212> TYPE: PRT
<213> ORGANISM: Unknown
<220> FEATURE:
<221> NAME/KEY: source
<223> OTHER INFORMATION: /note="Description of Unknown: Cecropin P1
      polypeptide"
```

```
<400> SEQUENCE: 48

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 49
<211> LENGTH: 30
<212> TYPE: PRT
<213> ORGANISM: Unknown
<220> FEATURE:
<221> NAME/KEY: source
<223> OTHER INFORMATION: /note="Description of Unknown: alpha-defensin
      polypeptide"

<400> SEQUENCE: 49

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 50
<211> LENGTH: 36
<212> TYPE: PRT
<213> ORGANISM: Unknown
<220> FEATURE:
<221> NAME/KEY: source
<223> OTHER INFORMATION: /note="Description of Unknown: beta-defensin
      polypeptide"

<400> SEQUENCE: 50

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 51
<211> LENGTH: 12
<212> TYPE: PRT
<213> ORGANISM: Unknown
<220> FEATURE:
<221> NAME/KEY: source
<223> OTHER INFORMATION: /note="Description of Unknown: Bactenecin
      peptide"

<400> SEQUENCE: 51

Arg Lys Cys Arg Ile Val Val Ile Arg Val Cys Arg
1               5                   10

<210> SEQ ID NO 52
<211> LENGTH: 42
<212> TYPE: PRT
<213> ORGANISM: Unknown
<220> FEATURE:
<221> NAME/KEY: source
<223> OTHER INFORMATION: /note="Description of Unknown: PR-39
      polypeptide"
<220> FEATURE:
<221> NAME/KEY: source
<223> OTHER INFORMATION: /note="C-term NH2"
```

-continued

```
<400> SEQUENCE: 52

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
            35                  40

<210> SEQ ID NO 53
<211> LENGTH: 13
<212> TYPE: PRT
<213> ORGANISM: Unknown
<220> FEATURE:
<221> NAME/KEY: source
<223> OTHER INFORMATION: /note="Description of Unknown: Indolicidin
      peptide"
<220> FEATURE:
<221> NAME/KEY: source
<223> OTHER INFORMATION: /note="C-term NH2"

<400> SEQUENCE: 53

Ile Leu Pro Trp Lys Trp Pro Trp Trp Pro Trp Arg Arg
1               5                   10

<210> SEQ ID NO 54
<211> LENGTH: 16
<212> TYPE: PRT
<213> ORGANISM: Unknown
<220> FEATURE:
<221> NAME/KEY: source
<223> OTHER INFORMATION: /note="Description of Unknown: RFGF
      peptide"

<400> SEQUENCE: 54

Ala Ala Val Ala Leu Leu Pro Ala Val Leu Leu Ala Leu Leu Ala Pro
1               5                   10                  15

<210> SEQ ID NO 55
<211> LENGTH: 11
<212> TYPE: PRT
<213> ORGANISM: Unknown
<220> FEATURE:
<221> NAME/KEY: source
<223> OTHER INFORMATION: /note="Description of Unknown: RFGF analogue
      peptide"

<400> SEQUENCE: 55

Ala Ala Leu Leu Pro Val Leu Leu Ala Ala Pro
1               5                   10

<210> SEQ ID NO 56
<211> LENGTH: 16
<212> TYPE: PRT
<213> ORGANISM: Drosophila sp.

<400> SEQUENCE: 56

Arg Gln Ile Lys Ile Trp Phe Gln Asn Arg Arg Met Lys Trp Lys Lys
1               5                   10                  15

<210> SEQ ID NO 57
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (3)..(4)
<223> OTHER INFORMATION: 2'F modified nucleotide
<220> FEATURE:
<221> NAME/KEY: modified_base
<222> LOCATION: (6)..(9)
<223> OTHER INFORMATION: 2'F modified nucleotide
<220> FEATURE:
<221> NAME/KEY: modified_base
<222> LOCATION: (13)..(16)
<223> OTHER INFORMATION: 2'F modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (20)..(21)
<223> OTHER INFORMATION: deoxythymidine
<220> FEATURE:
<221> NAME/KEY: misc_feature
<222> LOCATION: (20)..(21)
<223> OTHER INFORMATION: /note="phosphothioate linkage"

<400> SEQUENCE: 57
ggaucaucuc aagucuuact t                                              21

<210> SEQ ID NO 58
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'F modified nucleotide
<220> FEATURE:
<221> NAME/KEY: modified_base
<222> LOCATION: (6)..(8)
<223> OTHER INFORMATION: 2'F modified nucleotide
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (16)..(18)
<223> OTHER INFORMATION: 2'F modified nucleotide
<220> FEATURE:
<221> NAME/KEY: modified_base
<222> LOCATION: (20)..(21)
<223> OTHER INFORMATION: deoxythymidine
<220> FEATURE:
<221> NAME/KEY: misc_feature
<222> LOCATION: (20)..(21)
<223> OTHER INFORMATION: /note="phosphothioate linkage"

<400> SEQUENCE: 58
guaagacuug agaugaucct t                                              21
```

-continued

```
<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(3)
<223> OTHER INFORMATION: 2'OMe modified nucleotide
<220> FEATURE:
<221> NAME/KEY: modified_base
<222> LOCATION: (5)..(5)
<223> OTHER INFORMATION: 2'OMe modified nucleotide
<220> FEATURE:
<221> NAME/KEY: modified_base
<222> LOCATION: (7)..(8)
<223> OTHER INFORMATION: 2'OMe modified nucleotide
<220> FEATURE:
<221> NAME/KEY: modified_base
<222> LOCATION: (12)..(12)
<223> OTHER INFORMATION: 2'OMe modified nucleotide
<220> FEATURE:
<221> NAME/KEY: modified_base
<222> LOCATION: (14)..(17)
<223> OTHER INFORMATION: 2'OMe modified nucleotide
<220> FEATURE:
<221> NAME/KEY: modified_base
<222> LOCATION: (20)..(21)
<223> OTHER INFORMATION: deoxythymidine
<220> FEATURE:
<221> NAME/KEY: misc_feature
<222> LOCATION: (20)..(21)
<223> OTHER INFORMATION: /note="phosphothioate linkage"

<400> SEQUENCE: 59
cuuacgcuga guacuucgat t                                              21

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: deoxythymidine
<220> FEATURE:
<221> NAME/KEY: misc_feature
<222> LOCATION: (20)..(21)
<223> OTHER INFORMATION: /note="phosphothioate linkage"

<400> SEQUENCE: 60
ucgaaguacu cagcguaagt t                                              21

<210> SEQ ID NO 61
<211> LENGTH: 27
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic probe"

<400> SEQUENCE: 61
atcaagatca ttgctcctcc tgagcgc                                              27

<210> SEQ ID NO 62
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 62
aaacaatccg gaagcgacca acgc                                                 24

<210> SEQ ID NO 63
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
cctggcaccc agcacaat                                                        18

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
gccgatccac acggagtact                                                      20

<210> SEQ ID NO 65
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
aggtcctatg attatgtccg gttatg                                               26

<210> SEQ ID NO 66
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
gaatgtagcc atccatcctt gtc                                                  23
```